US008445678B2

(12) United States Patent
Gorden et al.

(10) Patent No.: US 8,445,678 B2
(45) Date of Patent: May 21, 2013

(54) 2-QUINOXALINOL SALEN COMPOUNDS AND USES THEREOF

(75) Inventors: Anne E. V. Gorden, Auburn, AL (US); Xianghong Wu, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 13/270,782

(22) Filed: Oct. 11, 2011

(65) Prior Publication Data
US 2012/0028362 A1 Feb. 2, 2012

Related U.S. Application Data

(63) Continuation of application No. 12/429,933, filed on Apr. 24, 2009, now abandoned.

(60) Provisional application No. 61/190,239, filed on Aug. 27, 2008, provisional application No. 61/196,305, filed on Oct. 16, 2008, provisional application No. 61/125,489, filed on Apr. 25, 2008.

(51) Int. Cl.
*C07D 241/36* (2006.01)
*G01N 33/00* (2006.01)

(52) U.S. Cl.
USPC .............. 544/354; 544/353; 544/356; 436/80

(58) Field of Classification Search
USPC ..................... 544/354, 353, 356; 436/80
See application file for complete search history.

(56) References Cited

U.S. PATENT DOCUMENTS

| | | |
|---|---|---|
| 6,589,948 B1 | 7/2003 | Malfroy-Camine et al. |
| 6,689,733 B1 | 2/2004 | Bachmann et al. |
| 6,713,435 B2 | 3/2004 | Katsuki et al. |
| 6,720,434 B2 | 4/2004 | Kim et al. |
| 6,723,879 B2 | 4/2004 | Katsuki et al. |
| 6,794,526 B2 | 9/2004 | Beck |
| 6,828,293 B1 | 12/2004 | Hazenkamp et al. |
| 6,884,750 B2 | 4/2005 | Kim et al. |
| 6,903,043 B2 | 6/2005 | Kim et al. |
| 6,982,243 B2 | 1/2006 | Hazenkamp et al. |
| 7,122,537 B2 | 10/2006 | Malfroy-Camine et al. |
| 7,385,038 B2 | 6/2008 | Hohsaka et al. |
| 7,468,458 B2 | 12/2008 | Tian et al. |
| 2003/0032821 A1 | 2/2003 | Kim et al. |
| 2003/0100763 A1 | 5/2003 | Beck et al. |
| 2003/0120091 A1 | 6/2003 | Katsuki et al. |
| 2003/0139627 A1 | 7/2003 | Katsuki et al. |
| 2003/0216250 A1 | 11/2003 | Kim et al. |
| 2003/0235852 A1 | 12/2003 | Roberts et al. |
| 2004/0054201 A1 | 3/2004 | Kim et al. |
| 2004/0059107 A1 | 3/2004 | Malfroy-Camine et al. |
| 2004/0259256 A1 | 12/2004 | Monahan et al. |
| 2004/0265952 A1 | 12/2004 | Deiters et al. |
| 2005/0085401 A1 | 4/2005 | Hazenkamp et al. |
| 2005/0256000 A1 | 11/2005 | Schaper et al. |
| 2006/0234339 A1 | 10/2006 | Yokoyama et al. |
| 2006/0246509 A1 | 11/2006 | Deiters et al. |
| 2007/0123503 A1 | 5/2007 | Malfroy-Camine et al. |
| 2009/0030172 A1 | 1/2009 | Zheng et al. |
| 2009/0036525 A1 | 2/2009 | Hobbs |
| 2009/0093405 A1 | 4/2009 | Wallen, III et al. |

FOREIGN PATENT DOCUMENTS

| | | |
|---|---|---|
| EP | 0609032 | 1/1994 |
| WO | 2007017284 | 2/2007 |

OTHER PUBLICATIONS

Xianghong Wu & Anne Gordon, An Efficient Method for Solution-Phase Parallel Synthesis of 2-Quinoxalinol Salen Schiff-Base Ligands, 9 J Comb. Chem. 601 (2007).*
Xianghong Wu, et al, Regioselective Synthesis of Asymmetrically Substituted 2-Quinoxalinol Salen Ligands, 72 J Org. Chem. 8691 (2007).*
Grubbs et al., "Olefin-metathesis catalysts for the preparation of molecules and materials (Nobel Lecture)", Angew. Chem. Int. Ed., 2006, 45:3760-3765.
Harrison et al., "Oxidative cleavage of ethers", Chemical Communications, 1966, 752.
Hassaballa et al., "Formation of lanthanide and actinide oxonium ion complexes with crown ethers from a liquid clathrate medium", Inorganic Chemistry, 1998, 37:4666-4671.
Henbest et al., "Aspects of stereochemistry. Part XI. Epoxide formation in the cycloHexene and bicycloHeptene series", Aspects of Stereochemistry, 1959, 221.
Hird et al., "Catalytic enantioselective alkylations of tetrasubstituted olefins. Synthesis of all-carbon quaternary stereogenic centers through cu-catalyzed asymmetric conjugate additions of alkylzinc reagests to enones", J. Am. Chem. Soc., 2005, 127:14988-14989.
Huang et al., "New approach to 2-quinoxlinones", Organic Letters, 2008, 10(4):673-676.
Hudson et al., "The trapping and decomposition of toxic gases such as hydrogen cyanide using modified mesoporous silicates", Microporous and Mesoporous Materials, 2004, 75:121-128.
Huguenot et al., "Concise synthesis of enantiopure alpha-trifluoromethyl alanines, diamines, and amino alcohols via the strecker-type reaction", J. Org. Chem., 2006, 71:7075-7078.
Iwata et al., "Cribrarione B, a new naphthoquinone pigment from the myxomycete cribraria cancellata", J. Nat. Prod., 2003, 66:1611-1612.
Jeanneau et al., "Influence of natural organic matter on the solid-phase extraction or organic micropollutants application to the water-extract from highly contaminated river sediment", Journal of Chromotography A, 2007, 1173:1-9.
Kamata et al., "Efficient heterogeneous oxidation of alkylarenes with molecular oxygen", Organic Letters, 2004, 6 (20):3577-3580.
Kannappan et al., "Separation of actinides and lanthanides: crystal and molecular structures of N, N'-bis(3,5-di-t-butylsalicylidene)-4,5-dimethyl-1,2-phenylenediamine and its uranium complex", Polyhedron, 2004, 23:2285-2291.

(Continued)

*Primary Examiner* — Sean Basquill
(74) *Attorney, Agent, or Firm* — Andrus, Sceales, Starke & Sawall, LLP

(57) ABSTRACT

Disclosed are 2-quinoxalinol salen compounds and in particular 2-quinoxalinol salen Schiff-base ligands. The disclosed 2-quinoxalinol salen compounds may be utilized as ligands for forming complexes with cations, and further, the formed complexes may be utilized as catalysts for oxidation reactions. The disclosed 2-quinoxalinol salen compounds also may be conjugated to solid supports and utilized in methods for selective solid-phase extraction or detection of cations.

14 Claims, 11 Drawing Sheets

OTHER PUBLICATIONS

Kawano et al., "Phenylethylamine-induced generation of reactive oxygen species and ascorbate free radicals in tobacco suspension culture: mechanism for oxidative burst mediating Ca2+ influx", Plant Cell Physiol, 2000, 41 (11):1259-1266.

Kim et al., "Antibiofouling polymer-coated gold nanoparticles as a contrast agent for in vivo x-ray computed tomography imaging", J. Am. Chem. Soc., 2007, 129:12585.

Kobayashi et al., "Catalytic enantioselective addition to imines", Chem. Rev., 1999, 99:1069-1094.

Kobayashi et al., "New methodologies for the synthesis of compound libraries", Chem. Soc. Rev., 1999, 28:1-15.

Komiya et al., "Manganes catalyzed asymmetric oxidation of alkanes to optically active ketones bearing asymmetric center at the alpha-position", Tetrahedron Letters, 1998, 39:7921-7924.

Krajewska et al., "Double mode of inhibition-inducing interactions of 1,4-naphthoquinone with urease: arylation versus oxidation of enzyme thiols", Bioorganic and Medicial Chemistry, 2007, 15:4144-4151.

Kumar et al., "Application of hydrolytic kinetic resolution (HKR) in the synthesis of bioactive compounds", Tetrahedron, 2007, 63:2745-2785.

Gillis, "N-benzylidenebenzylamine from benzylamine and butyl nitrite", J. Org. Chem., 1956, 21:805.

Lee et al., "2,3-dichloro-5,6-dicyano-1,4-benzoquinone (DDQ) in aqueous acetic acid, a convenient new reagent for the synthesis of aryl ketones and aldehydes via benzylic oxidation", J. Org. Chem., 1988, 53:4587-4589.

Lee et al., "Selective oxidation of benzylic hydrocarbons to carbonyl compounds catalyzed by Mn(III) salen complexes", Tetrahedron Letters, 1998, 39:1385-1388.

Lee et al., "Direct synthesis of styker's reagent from a Cu(II) salt", Tetrahedron Letters, 2005, 46:2037-2039.

Li et al., "A convenient synthesis of alpha,beta-acetylenic ketones", J. Org. Chem., 2001, 66:4087-4090.

Li et al., "Oxidation of alkanes catalyzed by manganese(III) porphyrin in an ionic liquid at room temperature", Tetrahedron Letters, 2003, 44:9229-9232.

Liu et al., "Solution-phase synthesis of a 1,5-dialkylamino-2,4-dinitrobenzene library and the identification of novel antibacterial compounds from this library", J. Comb. Chem., 2000, 2:467-474.

Look et al., "Trimethylorthoformate: a mild and effective dehydrating reagent for solution and solid phase imine formation", Tetrahedron Letters, 1995, 36(17):2937-2940.

Love et al., "Synthesis of Sterically Hindered Imines", J. Org. Chem., 1993, 58:5556-5557.

Lu et al., "Syntheses, crystal structures, and magnetic characterization of five new dimeric manganese(III) tetradentate schiff base complexes exhibiting single-molecule-magnet behavior", Inoranic Chemistry, 2006, 45:3538-3548.

Ma et al., "Oxidation of benzylic methylene compounds to ketones with m-chloroperoxybenzoic acid and oxygen", Tetrahedron Letters, 1999, 40:8915-8917.

Markgraf et al., "Oxication of benzyl ethers via phase transfer catalysis", Sythetic Communications, 1999, 29:14:2405-2411.

Markgraf et al., "A new synthesis of N-phenyl lactams", J. Heterocyclic Chem., Jan.-Feb. 2000, 37:109.

Martinez et al., "Catalyst-free multicomponent strecker reaction in acetonitrile", Tetrahedron Letters, 2005, 46:8471-8474.

Matloka et al., "CMPO-functionalized C3-symmetric tripodal ligands in liquid/liquid extractions: efficient, selective recognition of Pu(IV) with low affinity for 3+ metal ions", Inorganic Chemistry, 2007, 46:10549-10563.

Matsugi et al., "Reverse fluorous solid-phase extraction: a new technique for rapid separation of fluorous compounds", Organic Letters, 2004, 6(16):2717-2720.

Melfi et al., "Redox behavior of cyclo[6]pyrrole in the formation of a uranyl complex", Inorganic Chemistry, 2007, 46:5143-5145.

Minisci et al., "Aerobic oxidation of N-alkylamides catalyzed by N-hydroxyphthalimide under mild conditions. Polar and enthalpic effects", J. Org. Chem., 2002, 67:2671-2676.

Mootoo et al., "N-pentenyl 2-amino-2-deoxy glycosides undergo stereoselective coupling under mild, chemospecific conditions", Tetrahedron Letters, 1989, 30(18):2363-2366.

Murahashi et al., "Ruthenium-catalysed oxidation of secondary amines to imines using t-butyl hydroperoxide", J. Chem. Soc. Chem. Commun., 1985, 613.

Murahashi et al., "Ruthenium-catalyzed oxidation of alkanes with tert-butyl hydroperoxide and peracetic acid", J. Org. Chem., 2000, 65:9186-9193.

Musteata et al., "Biocompatible solid-phase microextraction coatings based on polyacrylonitrile and solid-phase extraction phases", Anal. Chem., 2007, 79:6903-6911.

Muzart, "Chromium-catalyzed oxidations in organic synthesis", Chem. Rev., 1992, 92:113-140.

Naota et al., "Rutehnium-catalyzed reactions for organic synthesis", Chem. Rev., 1998, 98:2599-2660.

Negele et al., "Photochemical oxidation of hydrocarbons by nitropyridinium salts", J. Org. Chem., 1998, 63:1138-1143.

Nocolaou et al., "The Art and Science of Total Synthesis at the Dawn of the Twenty-First Century", Angew. Chem. Int. Ed., 20000, 39:44-122.

Pan et al., "Catalytic asymmetric three-component acyl-strecker reaction", Organic Letters, 2007, 9(6):1149-1151.

Pan et al., "Catalytic asymmetric acylcyanation of imines", Angew. Chem. Int. Ed., 2007, 46:612-614.

Paquette et al., "Electronic Control of Stereoselectivity. 5. Stereochemistry of Singlet Oxygen Capture by Cyclopentadiene Rings Fused to Norbornyl and Norbornenyl Frameworks", J. Org. Chem., 1980, 45:4907-4913.

Pohl et al., "Fractionation analysis of manganese and zinc in tea infusions by two-column solid phase extraction and flame atomic absorption spectrometry", Food Chemistry, 2007, 102:1415-1424.

Posner, "Multicomponent one-pot annulations forming three to six bonds", Chem. Rev., 1986, 86:831-844.

Yang et al., "Mesoporous bimetallic PdCl2-CuCl2 catalysts for dimethyl carbonate synthesis by vapor phase oxidative carbonylation of methanol", Applied Catalysis A: General, 2003, 241:363-373.

Yu et al., "A mild, catalytic, and highly selective method for the oxidation of alpha,beta-enones to 1,4-enediones", J. Am. Chem. Soc., 2003, 125:3232-3233.

Zhang et al., "Enantioselective Epoxidation of unfunctionalized olefins catalyzed by (salen)manganese complexes", J. Am. Chem. Soc., 1990, 112:2801-2803.

Zhang et al., "A convenient and high yield method to prepare 4-hydroxypyroglutamic acid", Tetrahedron Letters, 2001, 42:5335-5338.

Zhang et al., "Parallel approach for solutions-phase synthesis of 2-quinoxalinol analogues and their inhibition of LPS-induced TNF-alpha release on mouse macrophages in vitro", J. Comb. Chem., 2004, 6:431-436.

Zhang et al., "96-well plate-to-plate gravity fluorous solid-phase extraction (F-SPE) for solution-phase library purification", J. Comb. Chem., 2007, 9:836-843.

Zhao et al., "Synthesis of Zn(II) ion-imprinted solid-phase extraction material and its analytical application", Analytica Chimica Acta, 2007, 603:87-92.

Pui et al., "Synthesis, characterization and catalytic activity of halomethyl-bis(salicylaldehyde)ethylenediamine cobalt (II) complexes" Polyhedron, 2007, 26:3143-3152.

Rangarajan et al., "Chromic acid oxidation of indans and tetralins to 1-indanones and 1-tetralones using jones and other Cr(VI) reagents", J. Org. Chem., 1985, 50:2432-2438.

Rao et al., "Base-catalyzed autoxidation of cyclic ketones", J. Org. Chem., 1979, 44(3):456.

Rao et al., "Synthesis, structure and reactivity of trans-UO2^2+ complexes of OH-containing ligands", J. Chem. Soc., Dalton Trans., 2000, 1213-1218.

Reinoso-Garcia et al., "Metal complexation by tripodal N-acyl(thio)urea and picolin(thio)amide compounds: synthesis/extraction and potentiometric studies", Eur. J. Org. Chem., 2005, 2131-2138.

Ritleng et al., "Ru-, Rh-, and Pd-catalyzed C-C bond formation involving C-H activation and addition on unsaturated substrates: reactions and mechanistic aspects", Chem. Rev., 2002, 102:1731-1769.

Rodrigues et al., "Application of solid-phase extraction to brewed coffee caffeine and organic acid determination by UV/HPLC", Journal of Food Compositionand Analysis, 2007, 20:440-448.

Rogers et al., "f-Element/crown ether complexes. 17. Synthetic and structural survey of lanthanide chloride triethylene glycol complexes", Inorg. Chem., 1988, 27:533-542.

Rossi et al., "Regioselective hydration and deprotection of chiral, dissymmetric iminodinitriles in the scope of an asymmetric strecker strategy", eur. J. Org. Chem., 2007, 662-668.

Rudkevich et al., "UO2-salenes: neutral receptors for anions with a high selectivity for dihydrogen phosphate", J. Am. Chem. Soc., 1992, 114:9671-9673.

Rudkevich et al., "Functionalized UO2 salenes: neutral receptors for anions", J. Am. Chem. Soc., 1994, 116:4341-4351.

Salmon et al., "Uranium(IV) complexes of calix[5]arene", Eur. J. Inorg. Chem., 2006, 4289-4293.

Salmon et al., "Uranium(IV) complexes of calix[n]arenes (n=4, 6 and 8)", Chem. Commun., 2006, 856-858.

Sanvicens et al., "Determination of haloanisols in white wine by immunosorbent solid-phase extraction followed by enzyme-linked immunosorbent assay", J. Agric. Food Chem., 2006, 54:9176-9183.

Sawicki et al., "Discovery of powerful uranyl ligands from efficient synthesis and screening", Chem. Eur. J., 2005, 11:3689-3697.

Schaus et al., "Asymmetric hetero-diels-alder reactions catalyzed by chiral (salen)chromium(III) complexes", J. Org. Chem., 1998, 63:403-405.

Schelter et al., "Systematic studies of early actinide complexes: uranium(IV) fluoroketimides", Inorganic Chemistry, 2007, 46:7477-7488.

Schrock, "Multiple metal-carbon bonds for catalytic metathesis reactions (Nobel lecture)", Angew. Chem. Int. Ed., 2006, 45:3748-3759.

Schuchardt et al., "Gif chemistry: new evidence for a non-radical process", Tetrahedron, 2001, 57:2685-2688.

Seayad et al., "Catalytic asymmetric pictet—spengler reaction", J. Am. Chem. Soc., 2006, 128:1086-1087.

Sessler et al., "Hexaphyrin(1.0.1.0.0.0). A new colorimetric actinide sensor", Tetrahedron, 2004, 60:11089-11097.

Sessler et al., "Schiff base oligopyrrolic macrocycles as ligands for lanthanides and actinides", Journal of Alloys and Compounds, 2006, 418:171-177.

Shaabani et al., "Solvent free permanganate oxidations", Tetrahedron Letters, 2001, 42:5833-5836.

Sharma et al., "Regioselective oxidation of N-alkylpyrrolidines to pyrrolidin-5-ones by RuCl3/NaIO4", Tetrahedron Letters, 2004, 45:1403-1406.

Sharpless et al., "Selenium dioxide oxidation of ketones and aldehydes. Eveidence for the intermediacy of beta-ketoseleninic acids", Journal of the American Chemical Society, Jan. 7, 1976, 98(1):300.

Shinkai et al., "Molecular design of calixarene-based uranophiles which exhibit remarkably high stability and selectivity", J. Am. Chem. Soc., 1987, 109:6371-6376.

Sigman et al., "Enantioselective addition of hydrogen cyanide to imines catalyzed by a chiral (salen)Al(III) complex", J. Am. Chem. Soc., 1998, 120:5315-5316.

Smiley et al., "Single molecule studies of enzyme mechanisms", Chem. Rev., 2006, 106:3080-3094.

Sopo et al., "Aminoalkylbis(phenolate) [O,N,O] donor ligands for uranyl(VI) ion coordination: syntheses, structures, and extraction studies", Polyhedron, 2007, 26:3397-3408.

Takao et al., "Structural characterization and reactivity of UO2(salophen)L and [UO2(salophen)]2: dimerization of UO2(salophen) fragments in noncoordinating solvents (salophen = N,N'-disalicylidene-o-phenylenediaminate, L = N,N-dimethylformamide,Dimethyl sufoxide)", Inorganic Chemistry, 2007, 46:1550-1562.

Tokuyama et al., "Novel synthesis of macroporous poly(N-isopropylacrylamide) hydrogels using oil-in-water emulsions", Langmuir, 2007, 23:11246-11251.

Tsunoi et al., "remote carbonylation. The synthesis of omega-lactones from saturated alcohols and carbon monoxide", J. Am. Chem. Soc., 1994, 116:5473-5474.

Ugi et al., "Since 1995 the new chemistry of multicomponent reactions and their libraries, including their heterocyclic chemistry", J. Heterocyclic Chem., May-Jun. 2000, 37:647.

Vanloot et al., "On-line solid-phase extraction and multisyringe flow injection analysis of Al(III) and Fe(III) in drinking water", Anal Bioanal Chem, 2007, 389:1595-1602.

Vaughn et al., "Contrasting solvent and capping ligand effects directing the photochemistry of uranyl(VI) schiff base complexes", J. Am. Chem. Soc., 2006, 128:10656-10657.

Velusamy et al., "Copper(II)-catalyzed C-H oxidation of alkylbenzenes and cyclohexane with hydrogen peroxide", Tetrahedron Letters, 2003, 44:8955-8957.

Walsh et al., "A green chemistry approach to asymmetric catalysis: solvent-free and highly concentrated reactions", Che. Rev., 2007, 107:2503-2545.

Wang et al., "Galactose oxidase model complexes: catalytic reactivities", J. Am. Chem. Soc., 1996, 118:13097-13098.

Wang et al., "Solvent-controlled asymmetric strecker reaction: stereoselective synthesis of alpha-trifluoromethylated alpha-amino acids", Organic Letters, 2006, 8(7):1379-1381.

Wasserman et al., "Reaction of singlet oxygen with enamino lactones. Conversion of lactones to alpha-keto lactones", J. Org. Chem., 1978, 43(16):3238.

Wasserman et al., "Reaction of singlet oxygen with enamino carbonyl systems. A general method for the synthesis of alpha-keto derivatives of lactones, esters, amides, lactams, and ketones", J. Org. Chem., 1985, 50:3573-3580.

Wei et al., "Anti-selective and regioselective aldol addition of ketones with aldehydes using MgI2 as promoter", Tetrahedron, 2004, 60:11829-11835.

Wilson et al., "Solid-phase extraction chormatography and nuclear magnetic resonance spectrometry for the identification and isolation of drug metabolites in uring", Anal. Chem., 1987, 59:2830-2832.

Wong et al., "Multinuclear luminescent schiff-base Zn-Nd Sandwich Complexes", Inorg. Chem., 2006, 45:4340-4345.

Wu et al., "Regio- and enantioselective cyclization of epoxy alcohols catalyzed by a [CoIII(salen)] complex", Angew. Chem. Int. Ed., 1999, 38:(13/14):2012.

Wu et al., "Regioselective synthesis of asymmetrically substituted 2-quinoxalinol salen ligands", J. Org. Chem., 2007, 72:8691-8699.

Wu et al., "2-quinoxalinol salen ligands incorporated into functionlized resins for selective solid-phase extraction of copper(II)", Tetrahedron Letters, 2008, 49:5200-5203.

Wu et al., "Synthesis and characterization of 2-quinoxalinol schiff-base metal complexes", Inorganica Chimica Acta, 2009, 362:1847-1854.

Wu et al., "2-quinoxalinol salen copper complexes for oxidation of aryl methylenes", Eur. J. Org. Chem., 2009, 503-509.

Yan et al., "Asymmetric hydrocyanation of olefins catalyzed by chiral diphosphite-nickel complexes", Tetrahedron: Asymmetry, 2000, 11:845-849.

Aguiari et al, "Macrocyclic and Macroacyclic compartmental Schiff bases: synthesis, characterization, X-ray structure and interaction with metal ions", Inorganica Chimica. Acta 202,1992, 157-171.

Annis et al., "Polymer-Supported Chiral Co(Salen) Complexes: Synthetic Applications and Mechanistic Investigations in the Hydrolytic Kinetic Resoluation of Terminal Epoxides", Journal of the American Chemistry Society, 1999, 121:4147-4154.

Banti et al, "Mechanistic studies on the asymmetric alkylation of amino ester enolates using a copper (II)salen catalyst", Chem. Comm. 2005, 2707-2709.

Bloch, "Additions of Organometallic Reagents to C=N Bonds: Reactivity and Selectivity", Chemical Reviews, 1998, 98:1407-1438.

Bregman et al, "An Organometallic Inhibitor for Glycogen Synthase Kinase 3", J. Am. Chem. Soc. 2004, 126, (24), 13594-13595.

Breinbauer et al., "Cooperative Asymmetric Catalysis with Dendrimeric [Co(salen)] Complexes", Angew. Chem. Int. Ed., 2000, 39(20):3604-3607.

Burger, "Isosterism and Bioisosterism in Drug Design", Progress in Drug Research, 1991, 287-328.

Canali et al, "Utilisation of homogeneous and supported chiral metal(salen) complexes in asymmetric catalysis", Chem. Soc. Rev. 1999, 28, 85-93.

Doctrow et al, "Salen-Manganese Complexes as Catalytic Scavengers of Hydrogen Peroxide and Cytoprotective Agents: Structure-Activity Relationship Studies", J. Med. Chem. 2002, 45, 4549-4558.

Fukuda et al, "Mn-Salen Catalyzed Asymmetric Oxidation of Enol Derivatives", Tetrahedron Letters, vol. 37, 1996, 4389-4392.

Gallant et al, "Mild and Selective Reduction of Imines: Formation of an Unsymmetrical Macrocycle", J. Org. Chem. 2004, 69, 8739-8744.

Gorden et al., "Rational Design of Sequestering Agents for Plutonium and Other Actinides", Chemical Reviews, 2003, 103:4207-4282.

Gordon et al, "Dialkyl aluminum amides: new reagents for the conversion of C=O into C=NR functionalities", Chem. Comm. 2002, 2710-2711.

Hamachi et al, "Asymmetric Benzylic Oxidation Using a Mn-Salen Complex as Catalyst", Tetrahedron Letters, vol. 1996, 37, 4979-4982.

Hayton et al., "Exchange of an Imido Ligand in Bis(imido) Complexes of Uranium", Journal of the American Chemistry Society, 2006, 128:12622-12623.

Holbach et al, "A Practical One-Pot Synthesis of Enantiopure Unsymmetrical Salen Ligands", J. Org. Chem. 2006, 71, 2903-2906.

Holbach et al, "Modular Approach for the Development of Supported, Monofunctionalized, Salen Catalysts", J. Org. Chem. 2006, 71, 1825-1836.

Irie et al, "Catalytic Asymmetric Epoxidation of Unfunctionalized Olefins", Tetrahedron Letters, vol. 31, No. 50. 1990, pp. 7345-7348.

Jacobsen et al, "Enantioselective Catalytic Ring Opening of Epoxides with Carboxylic Acids", Tetrahedron Letters, vol. 38, No. 5, 1997, 773-776.

Jaung, "Synthesis and halochromism of new quinoxaline fluorescent dyes", Dyes and Pigments 71, 2006, 245-250.

Katsuki, "Mn-salen catalyst, competitor of enzymes, for asymmetric epoxidation", Journal Molecular Catalysis A: Chemical 113, 1996, 87-10.

Liu et al, "Multistep Parallel Synthesis of Substituted 5-Aminobenzimidazoles in Solution Phase", J. Comb. Chem. 2004, 6, 811-821.

Marzano et al, Synthesis, Characterization, and in Vitro Antitumor Properties of Tris(hydroxymethyl)[jps[jome Copper(I) Complexes Containing the New Bis(1,2,4-triazol-1-yl)acetate Ligand, J. Med. Chem. 2006, 49, 7317-7324.

Mellah et al., "Electropolymerized Cr-salen complexes for the heterogeneous asymmetric hetero Diels-Alder reaction", Journal of Molecular Catalysis A: Chemical, 2007, 272:20-25.

Murahashi et al, "Ruthenium-catalysed Oxidation of Secondary Amines to Imines using t-Butyl Hydroperoxide", J. Chem. Soc., Chem. Commun. 1985, 613-614.

Niimi et al, "Co(II)-salen-catalyzed highly cis- and enantioselectie cyclopropanation", Tetrahedron Letters 41, 2000, 3647-3615.

Nishikori et al, "Mn-salen catalyzed enantioselective sulfimidation", Applied Catalysis A: General 2000, 194-195, 475-477.

Patani et al., "Biosterism: A rational approach to drug design", Chem Rev, 1996, 96:3147.

Peukert et al, "Enantioselective Parallel Synthesis Using Polymer-Supported Chiral Co(salen) Complexes", Organic Letters 1999, vol. 1, No. 8, 1245-1248.

Ready et al, "Highly Active Oligomeric (salen)Co Catalysts for Asymmetric Epoxide Ring-Opening Reactions", J. Am. Chem. Soc. 2001, 123, 2687-2688.

Sasaki et al, "Rational Design of Mn-Salen Catalyst (2): Highly Enantioselective Epoxidation of Conjugated cis-olefins", Tetrahedron vol. 50, No. 41, 1994, pp. 11827-11838.

Sun et al, "Aldehyde olefination with a rutheniuim(II) salen catalyst", Applied Catalysis A: General 2005, 285, 163-168.

Taylor et al. Journal of the American Chemistry Society, 2004, 126:10558-10559.

Vachal et al., "Enantioselective Catalytic Addition of HCN to Ketoimines. Catalytic Synthesis of Quaternary Amino Acids", Organic Letters, 2000, 2(6):867-870.

Wu et al, "An Efficient Method for Solution-Phase Parallel Synthesis of 2-Quinoxalinol Salen Schiff-Base Ligands", J. Comb. Chem., 2007, 9, pp. 601-608.

Wu et al, "Solution-phase reductive cyclization of 2-quinoxalinol analogs: Systematic study of parallel synthesis", Molecular Diversity, 8: 165-174, 2004.

Wu et al, "Asymmetric Ring Opening of Meso Epoxides with Thiols: Enantiomeric Enrichment Using a Bifunctional Nucleophile", J. Org. Chem. 1998, 63, 5252-5254.

Wu et al, "Regio- and Enantioselective Cyclization of Epoxy Alcohols Catalyzed by a [CoIII(salen)] Complex", Angew. Chem., Int. Ed. 1999, 38, No. 13/14, 2012-2014.

Yoon et al, "Privileged Chiral Catalysts", Science, 00368075, 2003, Issue 5613, vol. 299, 1691-1693.

Zhang et al, "Enantioselective Epoxidation of Unfunctionalilzed Olefins Catalyzed by (Salen)manganese Complexes", J. Am. Chem. Soc. 1990, 112, 2801-2083.

Zhang et al, "Asymmetric epoxidation iof 6-cyano-2,2-dimethylchromene on Mn(salen) catalyst immobilized in mesoporous materials", Tetrahedron 2006, 62, 6640-6649.

Zhang et al, "Parallel Approach for Solution-Phase Synthesis of 2-Quinoxalinol Analogues and Their Inhibition of LPS-Induced TNF-α Release on Mouse Macrophages in Vitro", J. Comb. Chem. 2004, 6, 431-436.

Abdel-Magid et al., "Reductive Amination of Aldehydes and Ketones with Sodium Triacetoxyborohydride. Studies on Direct and Indirect Reductive Amination Procedures", J. Org. Chem, 1996, 61:3849-3862.

About-Jaudet et al., "The Effect of Ligand Variation on the Rate of Cyclododecane Oxidation Under Modified GO AGG conditions", Tetrahedron Letters, 1990, 31(12):1657-1660.

Arai et al., "Practical Asymmetric Henry Reaction Catalyzed by a Chiral Diamine-Cu(OAc)2 Complex", Organic Letters, 2007, 9(18):3595-3597.

Arend, "Asymmetric Catalytic Aminoalkylations: New Powerful Methods for the Enantioselective Synthesis of Amino Acid Derivatives, Mannich Bases, and Homoallylic Amines", Angew. Chem. Int. Ed., 1999, 38(19):2873.

Aubry et al., "Prepartive oxidation of organic compounds in microemulsions with singlet oxygen generated chemically by the sodium molybdate/hydrogen peroxide system", J. Am. Chem. Soc., 1997, 119:5286-5294.

Barboso et al., "Calix[4]arenes with CMPO functions at the narrow rim. Synthesis and extraction properties", J. Chem. Soc., Perkin Trans. 2, 1999, 719-723.

Baron et al., "Structure and mechanism of galactose oxidase", The Journal of Biological Chemistry, Oct. 7, 1994, 269(40):25095-25105.

Barton, "On the mechanism of gif reactions", Chem. Soc. Rev., 1996, 25:237-239.

Basheer et al., "Application of porous membrane-protected micro-solid-phase extraction combined with HPLC for the analysis of acidic drugs in wastewater", Anal. Chem., 2007, 79:6845-6850.

Belokon et al., "Vanadium-Catalyzed Asymmetric Cyanohydrin Synthesis", Organic Letters, 2000, 2(11):1617-1619.

Belokon et al., "Optimized catalysts for the asymmetric addition of trimethylsilyl cyanide to aldehydes and ketones", Tetrahedron, 2001, 57:771-779.

Bharara et al., "Novel dinuclear uranyl complexes with asymmetric schiff base ligands: synthesis, structural characterization, reactivity, and extraction studies", Inorg. Chem., 2007, 46:8309-8315.

Bharara et al., "Uranyl stabilized schiff base complex", Chem. Commun., 2007, 4006-4008.

Bharara et al., "Hydroxy- and alkoxy-bridged dinuclear uranyl-schiff base complexes: hydrolysis, transamination and extraction studies", Dalton Trans., 2008, 2966-2973.

Biffis et al., "Metallation of functional resins with copper acetate: control of metal speciation and catalytic activity in C-N coupling reactions", Journal of Molecular Catalysis A: Chemical, 2003, 201:213-220.

Bonvin et al., "Bismuth-catalyzed benzylic oxidations with tert-butly hydroperoxide", Organic Letters, 2005, 7 (21):4549-4552.

Brandes et al., "Synthesis of enantiopure 3-chlorostyrene oxide via an asymmetric epoxidation-hydrolytic kinetic resolution sequence", Tetrahedron: Asymmetry, 1997, 8(23):3927-3933.

Bray et al., "Structural polarity induced by cooperative hydrogen bonding and lone-pair alignment in the molecular uranyl iodate Na2[UO2(IO3)4(H2O)]", Inorganic Chemistry, 2006, 45:8251-8257.

Breslow et al., "Selective Oxidation of Unactivated Methylene Groups by Reagent-Substrate Orientation in Mixed Complexes", J. Am. Chem. Soc., 1971, 93:2331.

Butler et al., "Vanadium Peroxide Complexes", Chem. Rev., 1994, 94:625-638.

Caron et al., "Large-scale oxidations in the pharmaceutical industry", Chem. Rev., 2006, 106:2943-2989.

Casellato et al., "Uranyl(VI) complexes with [1+1] asymmetric compartmental ligands containing a schiff base and a crown ether-like chamber", Inorganica Chimica Acta, 2002, 341:118-126.

Catino et al., "Dirhodium(II) caprolactamate: An exceptional catalyst for allylic oxidation", J. Am. Chem. Soc., 2004, 126:13622-13623.

Catino et al., "Benzylic Oxidation Catalyzed by Dirhodium(II,III) Caprolactamate", Organic Letters, 2005, 7 (23):5167-5170.

Chapman et al., "Enantioselective diels—alder reaction of optically active (Buta-1,3-dien-2-yl)(salen)cobalt(III) complexes", Eur. J. Org. Chem., 2001, 2273-2282.

Chauvin, "Olefin metathesis: The early days (Nobel Lecture)", Angew. Chem. Int. Ed., 2006, 45:3741-3747.

Chen et al., "Synthesis and characterization of linear cerium(IV) schiff-base coordination polymers", Macromolecules, 1994, 27:2174-2180.

Chen et al., "Thermal, Catalytic, Regiospecific Functionalization of Alkanes", Science, Mar. 17, 2000, 287:1995.

Choppin, "Technology for nuclear reprocessing: present and future directions", Separation Science and Technology, 2006, 41:1955-1963.

Connon et al., "Recent Developments in Olefin Cross-Metathesis", Angew. Chem. Int. Ed., 2003, 42:1900-1923.

Corey et al., "Studies on the mechanism of oxidation of ketones by selenium dioxide (Part I)", J. Am. Chem. Soc., 1960, 82:918.

Cossi et al., "Energies, structures, and electronic properties of molecules in solution with the C-PCM solvation model", J. Comput. Chem., 2003, 24:669.

Cui et al., "Chemically modified silica gel with p-dimethylaminobenzaldehyde for selective solid-phase extraction and preconcentration of Cr(III), Cu(II), Ni(II), Pb(II) and Zn(II) by ICP-OES", Microchemical Journal, 2007, 87:20-26.

Curran et al., "Fluorous synthesis with fewer fluorines (light fluorous synthesis): separation of tagged from untagged products by solid-phase extraction with fluorous reverse-phase silica gel", J. Am. Chem. Soc., 1999, 121:9069-9072.

Darensbourg et al., "Making plastics from carbon dioxide: salen metal complexes as catalysts for the production of polycarbonates from epoxides and CO2", Chem. Rev., 2007, 107:2388-2410.

Denmark et al., "Catalytic Asymmetric Synthesis", Acc. Chem. Res., 2000, 33(6):324.

Diamond et al., "An ion-exchange study of possible hybridized 5f bonding in the actinides", Journal of the American Chemical Society, Mar. 30, 1954, 76(6):1461.

Dickman et al., "Peroxo and superoxo complexes of chromium, molybdenum, and tungsten", Chem. Rev., 1994, 94:569-584.

Divrikli et al., "Solid-phase extraction of Fe(III), Pb(II) and Cr(III) in environmental samples on amberlite XAD-7 and their determinations by flame atomic absorption spectrometry", Journal of Hazardous Materials, 2007, 149:331-337.

Doumaux et al., "Peroxide-metal ion oxidations. II. A convenient synthesis of imides", J. Org. Chem., 1970, 35 (7):2121.

Duhamel et al., "A method for simple titration of organolithium reagents in ethers or hydrocarbons using metalation of n-benzylidenebenzylamine as colored reaction", J. Org. Chem., 1979, 44(19):3404.

Duran et al., "Solid-phase extraction of Mn(II), Co(II), Ni(II), Cu(II), Cd(II) and Pb(II) ions from environmental samples by flame atomic absorption spectrometry (FAAS)", Journal of Hazardous Materials, 2007, 146:347-355.

Dyker, "Transition metal catalyzed coupling reactions under C-H activation", Angew. Chem. Int. Ed., 1999, 38:1698-1712.

Elder et al., "Vitamin K Contents of Meat, Dairy, and Fast Food in the U.S. Diet", J. Agric. Food Chem., 2006, 54:463-467.

Enders et al., "Asymmetric synthesis of amines by nucleophilic 1,2-addition of organometallic reagents to the CN-double bond", Tetrahedron: Asymmetry, 1997, 8(12):1895-1946.

Erkkila et al., "Iminium Catalysis", Chem. Rev., 2007, 107:5416-5470.

Errante et al., "Synthesis and evaluation of antifungal activity of naphthoquinone derivatives", European Journal of Medicinal Chemistry, 2006, 41:773-778.

Ferraz et al., "Efficient entry into medium-ring keto-lactones. The ruthenium tetraoxide-promoted oxidative cleavage of beta-hydroxyethers", Organic Letters, 2003, 5(8):1337-1339.

Graves et al., "Organometallic uranium(V)—imido halide complexes: from synthesis to electronic structure and bonding", J. Am. Chem. Soc., 2008, 130:5272-5285.

Grigoriadou et al., "Solid phase extraction in the analysis of squalene and tocopherols in olive oil", Food Chemistry, 2007, 105:675-680.

Abu-Hussen, A.A., "Synthesis and spectroscopic studies on ternary bis-Schiff-base complexes having oxygen and/or nitrogen donors", J. Coord. Chem. 2006, 59:157.

Alvaro et al., "Addition of organometallic reagents to imines bearing stereogenic N-Substituents. Stereochemical models explaining the 1,3-Asymmetric induction", Synlett, 2002, 651.

Azizov et al., "Methods for preparation of 2-Methyl-1,4-Naphthoquinone (Review)", Pharma. Chem. J., 1989, 23 (12):1017.

Borisova et al., "Metal-Free methods in the synthesis of macrocyclic Schiff bases", Chem. Rev., 2007, 107:49.

Breneman et al., "Determining atom-centered monopoles from molecular electrostatic potentials. The need for high sampling density in formamide conformational analysis", J. Comput. Chem., 1990, 11:361.

Bruno et al., "Spent nuclear fuel", Elements, 2007, 2:343.

Carlsen et al., "A greatly improved procedure for Ruthenium Tetraoxide catalyzed oxidations of organic compounds", J. Org. Chem., 1981, 46:3936.

Charushnikova, I. A., "Behavior of uranyl malonate in concentrated acetic acid under hydrothermal conditions", Radiochemistry, 2008, 50:117.

Chatchawan et al., "Synthesis of Isagarin, a tetracyclic naphthoquinone via a palladium-catalyzed cyclization", Synth. Commun., 2007, 37(9):1463.

Dey et al., "Cassette in situ enzymatic screening identifies complementary chiral scaffolds for hydrolytic kinetic resolution across a range of epoxides", Angew. Chem. Int. Ed., 2007, 46:7010.

Durbin et al., "Development of decorporation agents for the actinides", Radiat. Prot. Dosim., 1998, 79:433.

Goldman A.S., "Ruthenium route to reaction", Nature, 1993, 366:514.

Krongauz, E.S., "Mono-and Bis-α-diketones and related polymers", Russ. Chem. Rev., 1977, 46:59.

Lau et al., "Oxidation of alkanes by barium ruthenate in acetic acid: Catalysis by Lewis acids", J. Chem. Soc. Chem. Commun., 1993, 766.

Lee et al., "Rapid microwave-promoted solvent-free oxidation of α-methylene ketones to α-diketones", Tetrahedron Lett, 2003, 43:5662.

Lutfullah et al., "Optimized and validated spectrophotometric method for the determination of uranium (VI) via complexation with meloxicam", Haz. Materials, 2008, 155:261.

Mathur et al., "Actinide partitioning—A review", Solv. Extr. Ion Exch. 2001, 19:357.

Minakata et al., "Catalytic oxidation of α-Carbon of ethers utilizing binuclear copper (II) complex of 7-Azaindole", Chem. Lett., 1996, 19.

Miyamoto et al., "A new aerobic oxidation system using Pd-Cu in the presence of CO", Chem. Lett., 1994, 1149.

Moreira et al., "Catalytic oxidative ring opening of THF promoted by a carboxylate-bridged Diiron complex, triarylphosphines, and dioxygen", Inorg. Chem., 2004, 43:4427.

Nara et al., "Beef liver mitochondrial monoamine oxidase, a copper-containing protein", J. Bio. Chem., 1966, 241 (12):2774.

Nash et al., "Separations chemistry for actinide elements: Recent developments and historical perspective", Sep. Sci. and Technol., 1997, 32:255.

Notari B., "Titanium silicalites", Catal. Today, 1993, 18:163.

Prugh et al., "A simple method of protecting a secondary amine with tert Butyloxycarbonyl (BOC) in the presence of a primary amine", Synth. Commun., 1992, 22:2357.

Rothenberg et al., "Copper-catalyzed homolytic and heterolytic benzylic and allylic oxidation using tert-butyl hydroperoxide", J. Chem. Soc., Perkin Trans 2, 1998, 2429.

Szigethy et al., "Surprising coordination geometry differences in CeIV- and PuIV-Maltol complexes", Eur. J. Inorg. Chem., 2008.

Van Axel et al., "Molecular recognition of carbonyl compounds by uranyl-salophen based neutral receptors driven by Van Der Waals forces", Superamolecular Chem., 2002, 14:211.

Van Doorn et al., "Synthesis of uranyl salophene metallomacrocycles with additional functional groups", Synthesis, 1992, 119.

Wang et al., "Palladium-catalyzed amination of 2,3-Dichloro-1,4-naphthoquinone with Nitroarylamines", Synlett., 2006, 6:942.

Weber et al., "Discovery of new multi component reactions with combinatorial methods", Synlett, 1999, 366.

Wu et al., "Solution-phase reductive cyclization of 2-Quinoxalinol analogs: systematic study of parallel synthesis", Mol. Diver., 2004, 8:165.

Wu et al., "An efficient method for solution-phase parallel synthesis of 2-Quinoxalinol salen Schiff-base ligands", J. Comb. Chem., 2007, 9:601.

* cited by examiner

M = Cu (1), Mn (2), Ni (3), Co (4), UO$_2$ (5).   Regular Salph Cu Complex (6)   Regular Salen Mn Complex (7)

2-QUINOXALINOL SALEN COMPOUNDS AND USES THEREOF

CROSS-REFERENCE TO RELATED APPLICATIONS

The present application is a continuation of U.S. application Ser. No. 12/429,933, filed on Apr. 24, 2009, which application claims the benefit of priority under 35 U.S.C. §119(e) to U.S. provisional application No. 61/125,489, filed on Apr. 25, 2008; U.S. provisional application No. 61/190,239, filed on Aug. 27, 2008; and U.S. provisional application No. 61/196,305, filed on Oct. 16, 2008; the contents of which are incorporated herein by reference in their entireties.

BACKGROUND

The present subject matter relates to 2-quinoxalinol salen compounds and in particular 2-quinoxalinol salen Schiff-base compounds. In particular, the disclosed 2-quinoxalinol salen compounds may be utilized as ligands for forming complexes with cations.

Salen ligands have been of interest to a wide variety of chemists. In particular, these have been investigated in a variety of applications because of their ease of preparation and ability to form stable complexes. For example, copper (I) salen complexes have been investigated as antitumor agents and protein kinase inhibitors. Salen ligands and their complexes also have been applied as catalysts in a variety of processes including as catalytic scavengers of hydrogen peroxide and cytoprotective agents, in the catalytic oxidation of secondary amines, in enantioselective catalysts for asymmetric epoxidation of unfunctionalized olefins or as catalysts for ring-opening metathesis. As catalysts, these complexes have proven quite useful, in particular after incorporation into solid supports and for chiral or stereoselective reaction catalysis. Therefore, new salen ligands are desirable.

Salen ligands are the product of a salicylic aldehyde compound and an ethylene diamine compound, hence the name "salen" is derived. Therefore, under suitable reaction conditions new ethylene diamine compounds may be utilized to create new salen ligands. 2-quinoxalinol is an ethylene diamine compound that previously has not been utilized for forming salen ligands. Derivatives of 2-quinoxalinols are key intermediates as bioactive agents in agriculture, have been used in dyes, and have been key pharmaceutical or medicinal intermediates. Synthetic methods for the parallel synthesis of 2-quinoxalinols have been previously reported. These factors have served to peak interest in utilizing 2-quinoxalinols for the preparation of a new series of 2-quinoxalinol salen framework ligands based on a Schiff base synthesis. The development of preparative methods using solution-phase parallel synthesis is not only feasible, but also desirable in the development of a new series of metal complexing agents that could be screened for bioactivity, or used in the development of new catalysts or metal selective sensors or sensing materials, through the incorporation of a unique coordination site and a quinoxaline that should have high UV and fluorescent activity. Taking advantage of a solution-phase combinatorial approach allows for the preparation of a series of ligands with a variety of substitution patterns. Here, it also is demonstrated that 2-quinoxalinols exhibit regioselectivity in Schiff base synthesis of salen ligands, which permits formation of asymmetrically substituted 2-quinoxalinol salen ligands.

SUMMARY

Disclosed are 2-quinoxalinol salen compounds and in particular 2-quinoxalinol salen Schiff-base ligands. The disclosed 2-quinoxalinol salen compounds may be utilized as ligands for forming complexes with cations. The formed complexes may be utilized as catalysts for oxidation reactions. Further, the disclosed 2-quinoxalinol salen compounds may be conjugated to solid supports and utilized in methods for selective solid-phase extraction or detection of cations.

In some embodiments, the disclosed compounds have a formula:

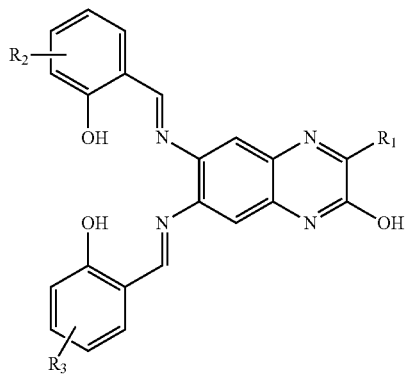

where $R_1$ is an amino acid side chain moiety and $R_2$ and $R_3$ are hydrogen, hydroxyl, $C_{1-6}$alkyl which may be straight chain or branched (e.g., 3-tert-butyl or 3,5-Di-tert butyl), $C_{1-6}$alkoxy which may be straight chain or branched, ether, or amine. The substituents $R_2$ and $R_3$ may be the same or different. In some embodiments, at least one of $R_2$ and $R_3$ is 3-OH or at least one of $R_2$ and $R_3$ is 5-OH. Salt forms of the disclosed compounds also are contemplated, for example salts of the dioxoanion are contemplated:

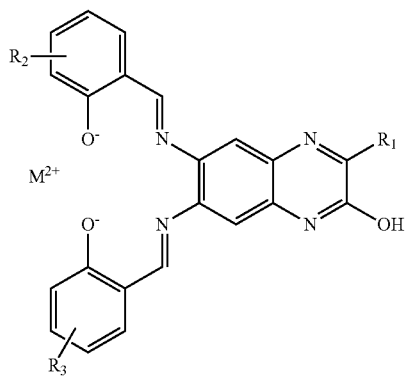

where $M^{2+}$ is a divalent metal cation. Typically, the disclosed compounds are fluorescent.

The substituent $R_1$ is an amino acid side chain moiety, which may be a side chain moiety of a naturally occurring amino acid or a non-naturally occurring amino acid. In some embodiments, $R_1$ is selected from:

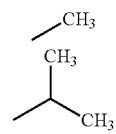

-continued

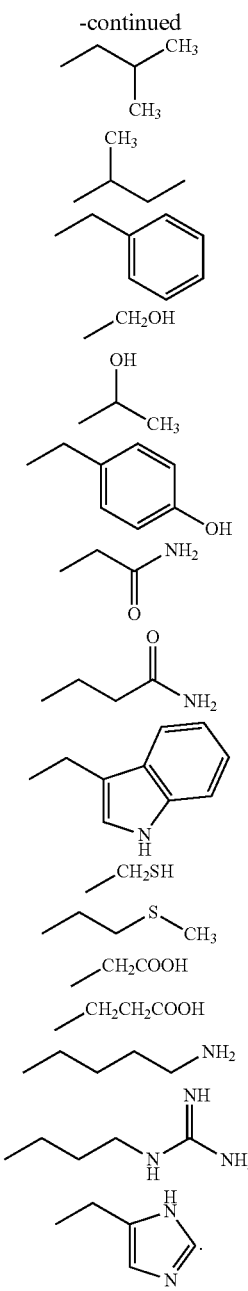

In other embodiments, $R_1$ may be selected from:

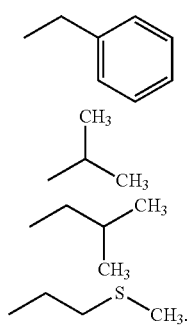

Preferably, $R_1$ is a side chain that increases the UV-Visible extinction coefficient of the compounds or that increases fluorescence of the compounds.

The disclosed compounds may form complexes with metal cations. In some embodiments, the disclosed compounds are complexed to a divalent cation, which may include, but is not limited to $Cu^{2+}$, $Mn^{2+}$, $Co^{2+}$, $Ni^{2+}$, $UO_2^{2+}$, $Fe^{2+}$, $Pd^{2+}$, $Ag^{2+}$, and $Sn^{2+}$, or mixtures thereof. In some embodiments, the complexes may be formed by first forming the salen compound and subsequently reacting the compound with a divalent cation. Alternatively, the compound may be formed in a reaction mixture that comprises the divalent cation.

The disclosed compounds and complexes may be conjugated to a solid support. Suitable solid supports may include functionalized resins, which may include, but are not limited to functionalized polystyrene and polyethylene resins. Suitable functionalized polystyrene resins include, but are not limited to, aminomethyl polystyrene resin, 2-chlorotrityl chloride resin, DHP HM resin, HMPA-AM resin, Knorr resin, Knorr-2-chlorotrityl resin, MBHA resin, Merrifield resin, oxime resin, PAM resin, Rink amide-AM resin, Rink amide-MBHA resin, Sieber resin, Wang resin, Weinreb AM resin, Boc-Ser-Merrifield resin, and Boc-Gly-Merrifield resin. Optionally, the disclosed compounds may be conjugated to the solid support via a linker compound such as an acylating linker compound. Suitable acylating linker compounds may include, but are not limited to, anhydride compounds such as acid anhydrides.

The disclosed compounds and complexes typically are fluorescent. In some embodiments, the disclosed compounds and complexes may be conjugated to additional fluorophores. The additional fluorophores optionally may be functionalized prior to conjugation with the disclosed compounds and complexes.

Also disclosed are methods for making the disclosed compounds. In some embodiments, the methods include reacting a reaction mixture comprising a 2-quinoxalinol compound, analog, or derivative having a formula:

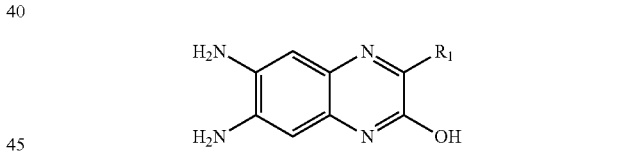

where $R_1$ is an amino acid side chain moiety; and a salicylic aldehyde, compound, analog, or derivative having a formula:

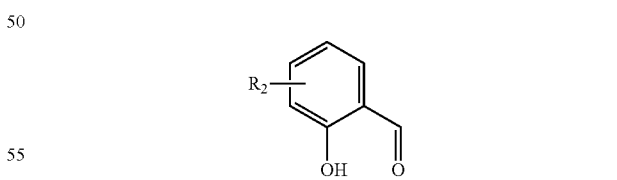

where $R_2$ is hydrogen, hydroxyl, $C_{1-6}$alkyl which may be straight chain or branched (e.g., 3-tert-butyl or 3,5-Di-tert butyl), $C_{1-6}$alkoxy which may be straight chain or branched, ether, or amine, thereby obtaining the salen compound. The 2-quinoxalinol compound, analog, or derivative and salicylic aldehyde compound, analog, or derivative may be present in the reaction mixture at a suitable ratio. For example, in some embodiments the reaction mixture comprises about equal molar amounts of the 2-quinoxalinol compound, analog, or derivative and the salicylic aldehyde compound, analog, or derivative. In other embodiments, the reaction mixture comprises an excess amount of the salicylic aldehyde compound, analog, or derivative as compared to the 2-quinoxalinol compound, analog, or derivative.

In some embodiments, the methods may include obtaining or isolating an intermediate compound having a formula:

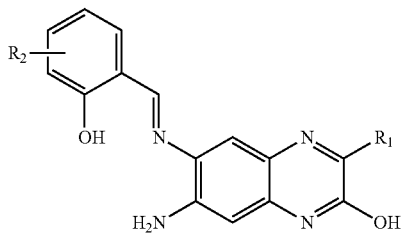

and reacting the intermediate in a reaction mixture with a salicylic aldehyde analog or derivative having a formula:

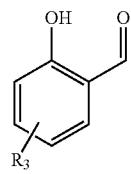

where $R_2$ and $R_3$ are hydrogen, hydroxyl, $C_{1-6}$alkyl which may be straight chain or branched (e.g., 3-tert-butyl or 3,5-Di-tert butyl), $C_{1-6}$alkoxy which may be straight chain or brandied, ether, or amine, thereby obtaining the salen compound. The substituents $R_2$ and $R_3$ may be the same or different in order to obtain a symmetrically substituted or asymmetrically substituted salen compound, respectively. Optionally, the reaction mixtures include an alcohol (e.g., MeOH) and reacting includes heating the reaction mixture.

Also disclosed are methods for utilizing the disclosed compounds. In some embodiments, the compounds may be utilized for removing a cation from a solution. Suitable cations for the removal methods may include divalent cations such as $Cu^{2+}$, $Mn^{2+}$, $Co^{2+}$, $Ni^{2+}$, $UO_2^{2+}$, $Fe^{2+}$, $Pd^{2+}$, $Ag^{2+}$, and $Sn^{2+}$, and mixtures thereof. Optionally, the compounds may be conjugated to a solid support prior to their use in the removal methods.

Also disclosed are methods for detecting a cation in a solution, which methods may include detecting divalent cations. The method may include: (a) contacting the solution with a salen compound, which optionally may be conjugated to a solid support or a fluorophore, where if the solution comprises the cation, the compound forms a complex with the cation; and (b) detecting the complex in the solution. The complex may be detected by methods which may include, but are not limited to, detecting a change in an absorption maximum for the solution, detecting a change in fluorescence of the compound (or detecting a change in fluorescence of an optionally conjugated fluorophore), or detecting a change in electrochemical properties of the solution.

In other embodiments, the methods for detecting a cation in a solution may include: (a) contacting the solution with complex comprising a complexed cation as disclosed herein, which complex optionally may be conjugated to a solid support or a fluorophore, where if the solution comprises the cation, the solution cation displaces the complexed cation from the compound and forms a new complex with the compound; and (b) detecting the new complex or detecting the displaced cation. In the methods, the new complex and displaced cation may be detected by steps which may include, but are not limited to, detecting a change in an absorption maximum for the solution, detecting a change in fluorescence of the compound (or detecting a change in fluorescence of an optionally conjugated fluorophore), or detecting a change in electrochemical properties of the solution.

In some embodiments, the formed complexes may be utilized as catalysts in chemical reactions. For example, the formed complexes may be utilized in oxidation reactions, which may include but are not limited to, oxidation reactions of methylenes (e.g., aryl, allyl, vinyl, or any other $\alpha,\beta$-unsaturated methylene), asymmetric epoxidation reactions, ring-opening reactions of epoxides, and oxidation reactions of amines. In some embodiments, methods for oxidizing compounds include reacting a methylene compound, an oxidizing agent, and a 2-quinoxalinol salen complex.

DETAILED DESCRIPTION

Figure 1:
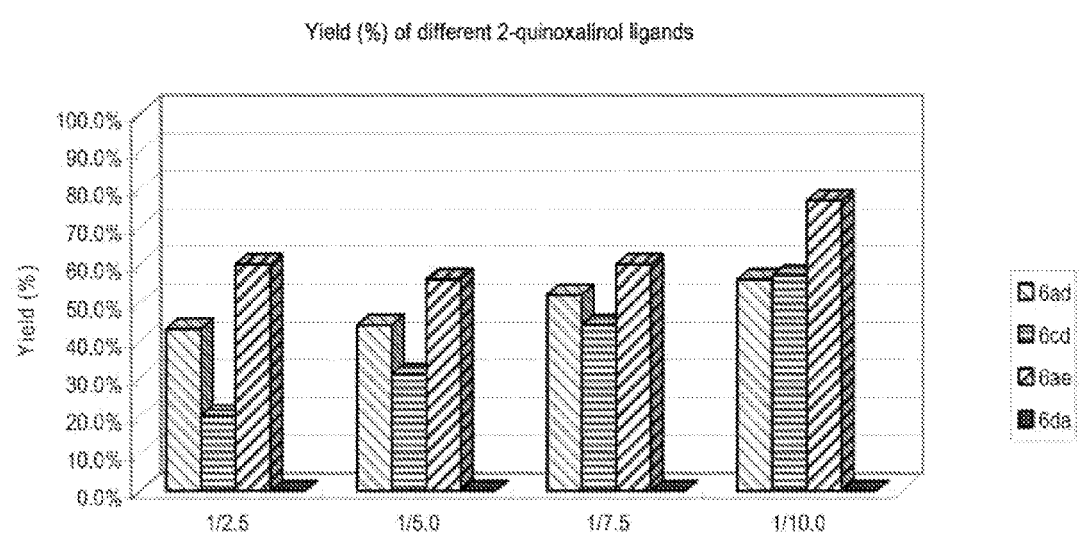
FIG. 1. illustrates the yield (%) for different salen compounds using various ratios of 2-quinoxalinol compounds and salicylic aldehyde compounds.

The disclosed subject matter is further described below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≦10% of the particular term and "substantially" and "significantly" will mean plus or minus >10% of the particular term.

As used herein, the terms "include" and "including" have the same meaning as the terms "comprise" and "comprising."

Disclosed herein are salen compounds. As used herein, a "salen" refers to a compound formed from a salicylic aldehyde compound (which may include salicylic aldehyde analogs or derivative) and an ethylene diamine compound (which may include ethylene diamine analogs or derivatives). As disclosed herein, salicylic aldehyde analogs or derivatives may include compounds having a formula:

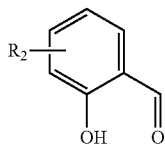

where $R_2$ is hydrogen, hydroxyl, $C_{1-6}$alkyl which may be straight chain or branched (e.g., 3-tert-butyl or 3,5-Di-tert butyl), $C_{1-6}$alkoxy which may be straight chain or branched, ether, or amine. As disclosed herein, an ethylene diamine analog or derivative may include 2-quinoxalinol or an analog or derivative thereof such as a compound having a formula:

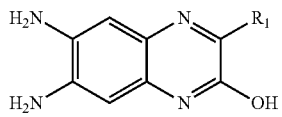

where $R_1$ is an amino acid side chain side chain moiety. Analogs of 2-quinoxalinol and methods for making and using such analogs are known in the art. (See, e.g., Zhang et al., J. Comb. Chem. 2004, 6, 431-436; and Wu et al., Molec. Diversity, 8: 165-174, 2004; the contents of which are incorporated herein by reference in their entireties including their disclosure related to analogs of analogs of 2-quinoxalinol and methods for making and using such analogs). Salen compounds and the use thereof (e.g., as ligands) also are known in the art. (See, e.g., U.S. Pat. Nos. 7,122,537; 6,982,243; 6,903,043; 6,884,750; 6,828,293; 6,794,526; 6,723,879; 6,720,434; 6,713,435; 6,689,733; and 6,589,948; and U.S. Published Application Nos. 2009-0030172; 2007-0123503; 2005-0085401; 2004-0059107; 2004-0054201; 2003-0216250; 2003-0139627; 2003-0120091; 2003-0100763; and 2003-0032821; the contents of which are incorporated by reference in their entireties including their disclosure related to salen compounds and their use as ligands for metal cations).

Salt forms of the disclosed salen compounds also are contemplated. For example, salt forms may include deprotonated forms of the salen compounds having a formula:

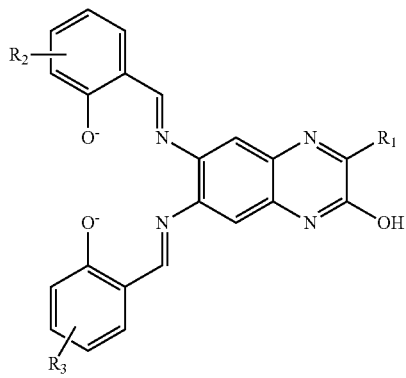

(i.e., the dioxoanion form), which optionally is bound conically to a cation, $M^{2+}$, which optionally is a divalent metal cation. Salt forms may be prepared by methods that include lithiation in order to form a lithium salt of the disclosed salon compound, for example, a compound having a formula:

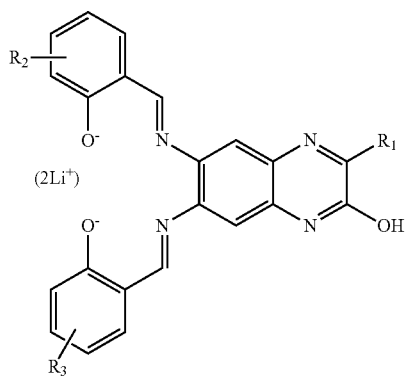

The lithium salt of the disclosed salen compound further may be reacted with a metal chloride salt $MCl_2$ to form a metal salt of the salen compound having a formula:

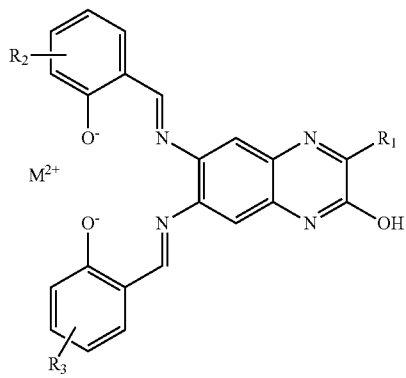

In some embodiments, $M^{2+}$ is a lanthanide metal such as gadolinium. These metal salts of the disclosed salen compounds may be utilized as catalysts in reactions that require C—H activation or in polymerization reactions.

Typically, the disclosed salen compounds are fluorescent. For example, when stimulating by light having a wavelength of 365 nm, 385 nm, 405 nm, 415 nm, or 546 nm, the compounds emit light having a wavelength within a range of 300-900 nm. In particular, two emission bands may be observed at 395 nm and 480 nm.

The disclosed salen compounds may be prepared from 2-quinoxalinol compounds, analogs, or derivatives reacted with salicylic aldehyde compounds, analogs, or derivatives. The 2-quinoxalinol compound, analogs, or derivatives may be prepared from natural or non-naturally amino acids. (See, e.g., Zhang et al., J. Comb. Chem. 2004, 6, 431-436; and Wu et al., Molec. Diversity, 8: 165-174, 2004; the contents of which are incorporated herein by reference in their entireties including their disclosure related to analogs or derivative of 2-quinoxalinol and methods for making and using such analogs.) Accordingly, the disclosed salen compounds may include a subsistent $R_1$ which is a side chain moiety of an amino acid. As disclosed herein, an "amino acid" refers to any naturally occurring or non-naturally occurring amino acid. Naturally occurring amino acids include the twenty (20) common amino acids (i.e., glycine, alanine, leucine, isoleucine, valine, phenylalanine, serine, threonine, cysteine, methionine, tyrosine, asparagine, glutamine, aspartic acid, glutamic acid, tryptophan, histidine, lysine, arginine, and proline), and pyrolysine and selenocysteine. In some embodiments, the disclosed salen compounds may include a substituent $R_1$ selected from:

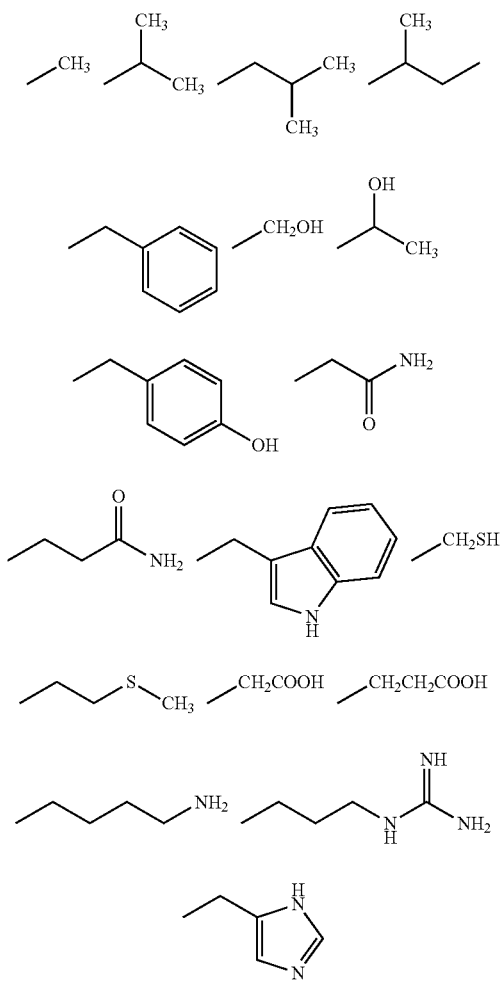

Preferably, $R_1$ is a side chain moiety that increases the UV-Visible extinction coefficient of the salen compounds or that increases fluorescence of the salen compounds. For example, $R_1$ may be an aromatic amino acid side chain moiety. Suitable, aromatic amino acid side chain moieties may comprise at least one 5- or 6-membered carbocyclic or heterocyclic ring, where the heterocyclic ring may be substituted with heteroatoms that include, but are not limited to, N, O, and S. In some embodiments, $R_1$ is a side chain moiety of a non-naturally occurring amino acid that increases the UV-Visible extinction coefficient of the salen compounds or that increases fluorescence of the salen compounds. For example, in some embodiments, $R_1$ may comprise naphthalene, anthracene, quinoline, quinoxaline, acridine, pyrimidine, pyridine, quinazoline, pyridazine, imidazole, indazole, indole, acenaphthylene, fluorine, phenanthrene, chrysene, pyrene, quinine, or anthraquinone.

Non-naturally occurring amino acids may be prepared by derivatizing a naturally occurring amino acid. In some embodiments, a non-naturally occurring amino acid may be derivatizing by conjugating to the side chain moiety of a naturally occurring amino acid a compound selected from naphthalene, anthracene, quinoline, quinoxaline, acridine, pyrimidine, pyridine, quinazoline, pyridazine, imidazole, indazole, indole, acenaphthylene, fluorine, phenanthrene, chrysene, pyrene, quinine, or anthraquinone. The non-naturally occurring amino acid thereby obtained may be utilized in the methods disclosed herein for synthesizing 2-quinoxalinol analogs. (See, e.g., Zhang et al., J. Comb. Chem. 2004, 6, 431-436; and Wu et al., Molec. Diversity, 8: 165-174, 2004; the contents of which are incorporated herein by reference in their entireties including their disclosure related to analogs or derivative of 2-quinoxalinol and methods for making and using such analogs). For example, the non-naturally occurring amino acid thereby obtained having a formula:

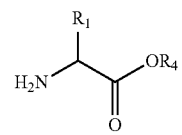

where $R_1$ is defined as above and $R_4$ is hydrogen or $C_{1-6}$alkyl which may be straight chain or branched (e.g., Me or Et) may be reacted with 1,5-difluoro-2,4-dinitrobenzene having a formula:

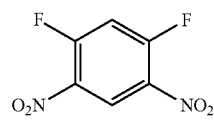

to obtain a compound having a formula:

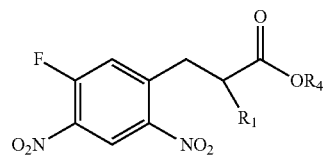

This compound further may be reacted with ammonia to obtain a compound having a formula:

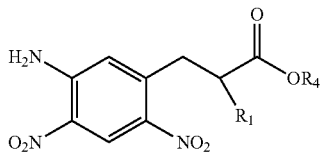

This compound further may be reduced and cyclized to obtain a 2-quinoxalinol compound, analog, or derivative having a formula:

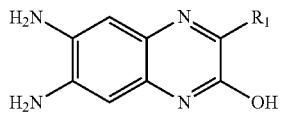

The 2-quinoxalinol compound, analog, or derivative thereby obtained may be utilized to prepare the presently disclosed salen compounds. Non-naturally occurring amino acids for use in preparing the disclosed 2-quinoxalinol compounds, analogs, and derivatives are known in the art and are described, e.g., in U.S. Pat. Nos. 7,468,458 and 7,385,038; and in U.S. Published Application Nos. 2009-0093405, 2009-0036525, 2006-0246509, 2006-0234339, 2004-0265952, 2004-0259256, and 2003-0235852, the contents of which are incorporated by reference herein in their entireties including their disclosure related to non-naturally occurring amino acids. Amino acids that are suitable for preparing the disclosed 2-quinoxalinol compounds, analogs, or derivatives may include natural or synthetic L-amino acids and D-amino acids. Derivatives of naturally occurring amino acids for preparing 2-quinoxalinol compounds, analogs, or derivatives also are available commercially. (See, e.g., Sigma-Aldrich® Catalog, the content of which is incorporated by reference in its entirety including disclosure related to amino acid derivatives).

Derivatives of alanine for preparing the disclosed 2-quinoxalinol compounds, analogs, or derivatives may include, but are not limited to (R)-(+)-α-Allylalanine, (S)-(−)-α-Allylalanine, D-2-Aminobutyric acid, L-2-Aminobutyric acid, 2-Aminoisobutyric acid, (S)-(+)-2-Amino-4-phenylbutyric acid, Boc-Abu-OH, Boc-D-Abu-OH, Boc-Aib-OH, Boc-β-(9-anthryl)-Ala-OH, Boc-β-(3-benzothienyl)-Ala-OH, Boc-β-(3-benzothienyl)-D-Ala-OH, Boc-Cha-OH, Boc-D-Cha-OH, Boc-Cha-OH, Boc-Cha-OMe, Boc-β-(2-furyl)-Ala-OH, Boc-β-(2-furyl)-D-Ala-OH, Boc-β-iodo-Ala-OBzl, Boc-β-iodo-D-Ala-OBzl, Boc-3-iodo-D-Ala-OMe, Boc-β-iodo-Ala-OMe, Boc-1-Nal-OH, Boc-D-1-Nal-OH, Boc-2-Nal-OH, Boc-D-2-Nal-OH, (R)-Boc-3-(2-naphthyl)-β-Ala-OH, (S)-Boc-3-(2-naphthyl)-β-Ala-OH, Boc-β-phenyl-Phe-OH, Boc-3-(1-pyrazolyl)-Ala-OH, Boc-3-(2-pyridyl)-β-Ala-OH, Boc-3-(3-pyridyl)-Ala-OH, (S)-Boc-3-(3-pyridyl)-β-Ala-OH, Boc-3-(3-pyridyl)-D-Ala-OH, Boc-3-(4-pyridyl)-Ala-OH, Boc-3-(4-pyridyl)-D-Ala-OH, Boc-β-2-quinolyl)-Ala-OH, Boc-3-(2-quinolyl)-DL-Ala-OH, Boc-3-(3-quinolyl)-DL-Ala-OH, Boc-3-(4-quinolyl)-DL-Ala-OH, Boc-3-(2-quinoxalyl)-DL-Ala-OH, Boc-β-styryl-Ala-OH, Boc-β-styryl-D-Ala-OH, Boc-β-(4-thiazolyl)-Ala-OH, Boc-β-(2-thienyl)-Ala-OH, Boc-β-(2-thienyl)-D-Ala-OH, Boc-β-(3-thienyl)-Ala-OH, Boc-β-(3-thienyl)-D-Ala-OH, Boc-3-(1,2,4-triazol-1-yl)-Ala-OH, 3-(5-Carboxy-2H-benzotriazol-2-yl)-L-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N—[(S)-(+)-1-(Ethoxycarbonyl)-3-phenylpropyl]-L-alanine, N-[1-(S)-(+)-Ethoxycarbonyl-3-phenylpropyl]-L-alanyl, Fmoc-Abu-OH, Fmoc-3-(9-anthryl)-Ala-OH, Fmoc-β-(3-benzothienyl)-Ala-OH, Fmoc-β-(3-benzothienyl)-D-Ala-OH, Fmoc-Cha-OH, Fmoc-D-Cha-OH, Fmoc-3-cyclopentyl-DL-Ala-OH, Fmoc-β-(2-furyl)-Ala-OH, Fmoc-β-(2-furyl)-D-Ala-OH, Fmoc-α-Me-Ala-OH, Fmoc-1-Nal-OH, Fmoc-D-1-Nal-OH, Fmoc-2-Nal-OH, Fmoc-D-2-Nal-OH, Fmoc-β-phenyl-Phe-OH, Fmoc-3-(1-pyrazolyl)-Ala-OH, Fmoc-β-(2-pyridyl)-Ala-OH, Fmoc-β-(2-pyridyl)-D-Ala-OH, Fmoc-β-(3-pyridyl)-Ala-OH, Fmoc-β-(3-pyridyl)-D-Ala-OH, Fmoc-β-(4-pyridyl)-Ala-OH, Fmoc-β-(4-pyridyl)-D-Ala-OH, Fmoc-β-(2-quinolyl)-DL-Ala-OH, Fmoc-β-styryl-Ala-OH, Fmoc-β-styryl-D-Ala-OH, Fmoc-β-(4-thiazolyl)-Ala-OH, Fmoc-β-(2-thienyl)-Ala-OH, Fmoc-β-(3-thienyl)-Ala-OH, Fmoc-β-(3-thienyl)-D-Ala-OH, Fmoc-3-(1,2,4-triazol-1-yl)-Ala-OH, N-(3-Indolylacetyl)-L-alanine, 3-(2-Naphthyl)-D-alanine, 3-(2-Oxo-1,2-dihydro-4-quinolinyl)alanine, 3-(1-Pyrazolyl)-L-alanine, 3-(2-Pyridyl)-D-alanine, 3-(2-Pyridyl)-L-alanine, 3-(3-Pyridyl)-D-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, 3-(2-Tetrazolyl)-L-alanine, 3-(2-Thienyl)-L-alanine, 3-(2-Thienyl)-DL-alanine, L-Thyroxine, 3-(1,2,4-Triazol-1-yl)-L-alanine, 3,3,3-Trifluoro-DL-alanine, and 3-Ureidopropionic acid. The 2-quinoxalinol compounds, analogs, or derivatives thereby obtained may be utilized to prepare the presently disclosed salen compounds.

Derivatives of arginine for preparing the disclosed 2-quinoxalinol compounds, analogs, or derivatives may include, but are not limited to, L-2-Amino-3-guanidinopropionic acid hydrochloride, 4-Guanidinobutyric acid, and NωNitro-L-arginine benzyl ester p-toluenesulfonate salt. The 2-quinoxalinol compounds, analogs, or derivatives thereby obtained may be utilized to prepare the presently disclosed salen compounds.

Derivatives of asparagine for preparing the disclosed 2-quinoxalinol compounds, analogs, or derivatives may include, but are not limited to, Boe-Asn(Xan)-OH. The 2-quinoxalinol compounds, analogs, or derivatives thereby obtained may be utilized to prepare the presently disclosed salen compounds.

Derivatives of aspartic acid for preparing the disclosed 2-quinoxalinol compounds, analogs, or derivatives may include, but are not limited to, N-Z-L-aspartic acid. The 2-quinoxalinol compounds, analogs, or derivatives thereby obtained may be utilized to prepare the presently disclosed salen compounds.

Derivatives of cysteine for preparing the disclosed 2-quinoxalinol compounds, analogs, or derivatives may include, but are not limited to, L-Cystathionine, L-Cysteic acid, L-Cysteinesulfinic acid, Se-Methyl-seleno-L-cysteine, Seleno-L-cystine, S-(2-Thiazolyl)-L-cysteine, S-(2-Thienyl)-L-cysteine, and S-(4-Tolyl)-L-cysteine. The 2-quinoxalinol compounds, analogs, or derivatives thereby obtained may be utilized to prepare the presently disclosed salen compounds.

Derivatives of glutamic acid for preparing the disclosed 2-quinoxalinol compounds, analogs, or derivatives may include, but are not limited to, D-2-Aminoadipic acid, γ-Carboxy-DL-glutamic acid, and 4-Fluoro-DL-glutamic acid. The 2-quinoxalinol compounds, analogs, or derivatives thereby obtained may be utilized to prepare the presently disclosed salen compounds.

Derivatives of glutamine for preparing the disclosed 2-quinoxalinol compounds, analogs, or derivatives may include, but are not limited to, Boc-Cit-OH, Boc-D-Cit-OH, D-Citrulline, Fmoc-Cit-OH, and Thio-L-citrulline. The 2-quinoxalinol compounds, analogs, or derivatives thereby obtained may be utilized to prepare the presently disclosed salen compounds.

Derivatives of histidine for preparing the disclosed 2-quinoxalinol compounds, analogs, or derivatives may include, but are not limited to, N-Boc-3-(3-methyl-4-nitrobenzyl)-L-histidine methyl ester. The 2-quinoxalinol compounds, analogs, or derivatives thereby obtained may be utilized to prepare the presently disclosed salen compounds.

Derivatives of isoleucine for preparing the disclosed 2-quinoxalinol compounds, analogs, or derivatives may include, but are not limited to, Boc-allo-Ile-OH, D-allo-Isoleucine, and DL-allo-Isoleucine. The 2-quinoxalinol compounds, analogs, or derivatives thereby obtained may be utilized to prepare the presently disclosed salen compounds, Derivatives of leucine for preparing the disclosed 2-quinoxalinol compounds, analogs, or derivatives may include, but are not limited to, N-[(2S,3R)-3-Amino-2-hydroxy-4-phenylbutyryl]-L-leucine, Boc-4,5-dehydro-Leu-OH (dicyclohexylammonium) salt, Boc-Ile-OSu, N-(3,5-Dinitrobenzoyl)-DL-leucine, Fmoc-tBu-Gly-OH, N-(3-Indolylacetyl)-L-isoleucine, D-tert-Leucine, L-tert-Leucine, DL-tert-Leucine, L-tert-Leucine methyl ester, and 5,5,5-Trifluoro-DL-leucine. The 2-quitioxalinol compounds, analogs, or derivatives thereby obtained may be utilized to prepare the presently disclosed salen compounds.

Derivatives of lysine for preparing the disclosed 2-quinoxalinol compounds, analogs, or derivatives may include, but are not limited to, DL-5-Hydroxylysine, and (5R)-5-Hydroxy-L-lysine. The 2-quinoxalinol compounds, analogs, or derivatives thereby obtained may be utilized to prepare the presently disclosed salen compounds.

Derivatives of phenylalanine for preparing the disclosed 2-quinoxalinol compounds, analogs, or derivatives may include, but are not limited to, 4-Amino-L-phenylalanine, Boc-Bpa-OH, Boc-D-Bpa-OH, Boc-4-tert-butyl-Phe-OH, Boc-4-tert-butyl-D-Phe-OH, Boc-4-(Fmoc-amino)-L-phenylalanine, (S)-Boc-4-methoxy-β-Phe-OH, Boc-pentafluoro-D-phenylalanine, Boc-pentafluoro-L-phenylalanine, Boc-Phe(4-Br)—OH, Boc-D-Phe(4-Br)—OH, Boc-Phe(2-CF3)-OH, Boc-D-Phe(2-CF3)-OH, Boc-Phe(3-CF3)-OH, Boc-D-Phe(3-CF3)-OH, Boc-Phe(4-CF3)-OH, Boc-D-Phe(4-CF3)-OH, Boc-Phe(2-Cl)—OH, Boc-D-Phe(2-Cl)—OH, Boc-Phe(2,4-Cl2)-OH, Boc-D-Phe(2,4-Cl2)-OH, Boc-D-Phe(3-Cl)—OH, Boc-Phe(3,4-Cl2)-OH, Boc-D-Phe(3,4-Cl2)-OH, Boc-Phe(4-Cl)-OH, Boc-D-Phe(4-Cl)—OH, Boc-Phe(2-CN)—OH, Boc-D-Phe(2-CN)—OH, Boc-Phe(3-CN)—OH, Boc-D-Phe(3-CN)—OH, Boc-Phe(4-CN)—OH, Boc-D-Phe(4-CN)—OH, Boc-Phe(2-Me)—OH, Boc-D-Phe(2-Me)—OH, Boc-Phe(3-Me)—OH, Boc-D-Phe(3-Me)—OH, Boc-Phe(4-Me)—OH, Boc-D-Phe(4-Me)—OH, Boc-Phe(4-NH2)-OH, Boc-Phe(4-NO2)-OH, Boc-D-Phe(4-NO2)-OH, Boc-Phe(2-F)—OH, Boc-D-Phe(2-F)—OH, Boc-Phe(3-F)—OH, Boc-D-Phe(3-F)—OH, Boc-Phe(3,4-F2)-OH, Boc-D-Phe(3,4-F2)-OH, Boc-Phe(3,5-F2)-OH, Boc-Phe(4-F)—OH, Boc-D-Phe(4-F)—OH, Boc-Phe(4-I)—OH, Boc-D-Phe(4-I)—OH, 4-Borono-D-phenylalanine, 4-Borono-L-phenylalanine, 4-Borono-DL-phenylalanine, 4-Borono-DL-phenylalanine, p-Bromo-DL-phenylalanine, 4-Bromo-L-phenylalanine, N-(tert-Butoxycarbonyl)-β-phenyl-D-phenylalanine, 4-Chloro-L-phenylalanine, DL-3,5-Difluorophenylalanine, 3,4-Dihydroxy-L-phenylalanine, 3,4-Dihydroxy-L-phenylalanine, 3,4-Dihydroxy-DL-phenylalanine, 3-(3,4-Dimethoxyphenyl)-L-alanine, o-Fluoro-D-phenylalanine, o-Fluoro-L-phenylalanine, o-Fluoro-DL-phenylalanine, m-Fluoro-L-phenylalanine, m-Fluoro-DL-phenylalanine, m-Fluoro-DL-phenylalanine, p-Fluoro-D-phenylalanine, p-Fluoro-D-phenylalanine, p-Fluoro-L-phenylalanine, p-Fluoro-L-phenylalanine, p-Fluoro-DL-phenylalanine, p-Fluoro-DL-phenylalanine, D-4-Fluorophenylalanine, L-4-Fluorophenylalanine, Fmoc-Bpa-OH, Fmoc-D-Bpa-OH, Fmoc-pentafluoro-L-phenylalanine, Fmoc-Phe(4-Boc2-guanidino)-OH, Fmoc-Phe(4-Br)—OH, Fmoc-Phe(2-CF3)-OH, Fmoc-D-Phe(2-CF3)-OH, Fmoc-Phe(3-CF3)-OH, Fmoc-D-Phe(3-CF3)-OH, Fmoc-Phe(4-CF3)-OH, Fmoc-D-Phe(4-CF3)-OH, Fmoc-Phe(2-Cl)—CF3)-OH, Fmoc-D-Phe(2-Cl)—OH, Fmoc-Phe(2,4-Cl2)-OH, Fmoc-D-Phe(2,4-Cl2)-OH, Fmoc-Phe(3,4-Cl2)-OH, Fmoc-D-Phe(3,4-Cl2)-OH, Fmoc-Phe(4-Cl)—OH, Fmoc-D-Phe(4-Cl)—OH, Fmoc-Phe(2-CN)—OH, Fmoc-D-Phe(2-CN)—OH, Fmoc-Phe(3-CN)—OH, Fmoc-D-Phe(3-CN)—OH, Fmoc-Phe(4-CN)—OH, Fmoc-Phe(2-Me)—OH, Fmoc-D-Phe(2-Me)—OH, Fmoc-Phe(3-Me)—OH, Fmoc-D-Phe(3-Me)—OH, Fmoc-Phe(4-Me)—OH, Fmoc-D-Phe(4-Me)—OH, Fmoc-Phe(4-NO2)-OH, Fmoc-Phe(2-F)—OH, Fmoc-D-Phe(2-F)—OH, Fmoc-Phe(3-F)—OH, Fmoc-D-Phe(3-F)—OH, Fmoc-Phe(3,4-F2)-OH, Fmoc-D-Phe(3,4-F2)-OH, Fmoc-Phe(3,5-F2)-OH, Fmoc-Phe(4-F)—OH, Fmoc-D-Phe(4-F)—OH, Fmoc-Phe(4-I)—OH, Fmoc-D-Phe(4-I)—OH, Fmoc-4-(phosphonomethyl)-Phe-OH, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, β-Methyl-DL-phenylalanine, α-Methyl-DL-phenylalanine, 4-Nitro-D-phenylalanine, 4-Nitro-DL-phenylalanine, 4-Nitro-L-phenylalanine, 4-Nitro-L-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 4-(Trifluoromethyl)-L-phenylalanine, and 3,3',5-Triiodo-L-thyronine. The 2-quinoxalinol compounds, analogs, or derivatives thereby obtained may be utilized to prepare the presently disclosed salen compounds.

Derivatives of serine for preparing the disclosed 2-quinoxalinol compounds, analogs, or derivatives may include, but are not limited to, N-Benzoyl-(2R,3S)-3-phenylisoserine, L-Isoserine, DL-Isoserine, DL-Isoserine, and DL-3-Phenylserine. The 2-quinoxalinol compounds, analogs, or derivatives thereby obtained may be utilized to prepare the presently disclosed salen compounds.

Derivatives of threonine for preparing the disclosed 2-quinoxalinol compounds, analogs, or derivatives may include, but are not limited to, D-allo-Threonine, and L-allo-Threonine. The 2-quinoxalinol compounds, analogs, or derivatives thereby obtained may be utilized to prepare the presently disclosed salen compounds.

Derivatives of tryptophan for preparing the disclosed 2-quinoxalinol compounds, analogs, or derivatives may include, but are not limited to, 5-Fluoro-L-tryptophan, 5-Fluoro-DL-tryptophan, 5-Hydroxy-L-tryptophan, 5-Methoxy-DL-tryptophan, 5-Methyl-DL-tryptophan, 5-Methyl-DL-tryptophan, and 6-Methyl-DL-tryptophan. The 2-quinoxalinol compounds, analogs, or derivatives thereby obtained may be utilized to prepare the presently disclosed salen compounds.

Derivatives of tyrosine for preparing the disclosed 2-quinoxalinol compounds, analogs, or derivatives may include, but are not limited to, 3-Amino-L-tyrosine, Boc-Tyr(3,5-I2)-OSu, 3-Chloro-L-tyrosine, 3,5-Diiodo-L-tyrosine, Fmoc-Tyr(3-NO2)-OH, Fmoc-Tyr(3,5-I2)-OH, α-Methyl-DL-tyrosine, α-Methyl-DL-tyrosine methyl ester, 3-Nitro-L-tyrosine, 3-Nitro-L-tyrosine ethyl ester, DL-o-Tyrosine, and DL-m-Tyrosine. The 2-quinoxalinol compounds, analogs, or derivatives thereby obtained may be utilized to prepare the presently disclosed salen compounds.

Derivatives of valine for preparing the disclosed 2-quinoxalinol compounds, analogs, or derivatives may include, but are not limited to, 3-Fluoro-DL-valine, (R)-(+)-α-Methylvaline, and (S)-(-)-α-Methylvaline. The 2-quinoxalinol compounds, analogs, or derivatives thereby obtained may be utilized to prepare the presently disclosed salen compounds.

Other suitable amino acids for preparing the disclosed 2-quinoxalinol compounds, analogs, or derivatives may include, but are not limited to, 2,4-Diaminobutyric Acid, 2,3-Diaminopropionic Acid, Norleucine, Norvaline, Ornithine, and Pyroglutamine, or analogs or derivatives thereof. The 2-quinoxalinol compounds, analogs, or derivatives thereby obtained may be utilized to prepare the presently disclosed salen compounds.

The disclosed salen compounds may function as ligands for cations such as divalent metal cations. Divalent metal cations may include, but are not limited to $Cu^{2+}$, $Mn^{2+}$, $Co^{2+}$, $Ni^{2+}$, $UO_2^{2+}$, $Fe^{2+}$, $Pd^{2+}$, $Ag^{2+}$, and $Sn^{2+}$, and $Sn^{2+}$, and mixtures thereof. In some embodiments, the complexes may be formed by first forming the salen compound and subsequently reacting the salen compound with a divalent cation (i.e., in a two-step synthesis method). Alternatively, the complex may be formed in a reaction mixture that comprises the components for forming the salen compounds and the divalent cation (i.e., in a one-step synthesis method). (See Example 4 below.)

The disclosed salen compounds and complexes may be conjugated to a solid support. Suitable solid supports may include resins, which may be incorporated into filter cartridges or utilized in batch methods. In some embodiments, suitable resins may include polystyrene resins or polyethylene resins. The resins typically are functionalized (e.g., with one or more of an aminomethyl group, a 2-chlorotrityl group, an oxime group, an amide group, or the like). Suitable functionalized polystyrene resins may include, but are not limited to, aminomethyl polystyrene resin, 2-chlorotrityl chloride resin, DHP HM resin, HMPA-AM resin, Knorr resin, Knorr-2-chlorotrityl resin, MBHA resin, Merrifield resin, oxime resin, PAM resin, Rink amide-AM resin, Rink amide-MBHA resin, Sieber resin, Wang resin, Weinreb AM resin, Boc-Ser-Merrifield resin, and Boc-Gly-Merrifield resin.

The disclosed salen compounds and complexes typically are fluorescent. However, the disclosed salen compounds and complexes may be conjugated to additional fluorophores as known in the art. Suitable additional fluorophores may include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxytetramethylrhodamine (5-TAMRA); 5-FAM (5-Carboxyfluorescein); 5-HAT (Hydroxy Tryptamine); 5-Hydroxy Tryptamine (HAT); 5-ROX (carboxy-X-rhodamine); 5-TAMIA (5-carboxytetramethylrhodamine); 6-Carboxyrhodamine 6G; 6-CR 6G; 6-JOE; 7-Amino-4-methylcoumarin; 7-Aminoactinomycin D (7-AAD); 7-Hydroxy-4-methylcoumarin; 9-Amino-6-chloro-2-methoxyacridine; ABQ; Acid Fuchsin; ACMA (9-Amino-6-chloro-2-methoxyacridine); Acridine Orange; Acridine Red; Acridine Yellow; Acriflavin; Acriflavin Feulgen SITSA; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexion; Alizarin Red; Allophycocyanin (APC); AMC; AMCA-S; AMCA (Aminomethylcoumarin); AMCA-X; Aminoactinomycin D; Aminocoumarin; Atninomethylcournarin (AMCA); Anilin Blue; Anthrocyl stearate; APC (Allophycocyanin); APC-Cy7; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); Berberine Sulphate; Beta Lactamase; BFP blue shifted GFP (Y66H); Blue Fluorescent Protein; BFP/GFP FRET; Bimane; Bisbenzamide; Bisbenzimide (Hoechst); Blancophor FFG; Blancophor SV; BOBO™-1; BOBO™-3; Bodipy 492/515; Bodipy 493/503; Bodipy 500/510; Bodipy 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy FL; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PROTK-3; Brilliant Suiphoflavin FF; Calcein; Calcein Blue; Calcium Crimson™; Calcium Green; Calcium Orange; Calcofluor White; Carboxy-X-rhodamine (5-ROX); Cascade Blue™; Cascade Yellow; Catecholamine; CCF2 (GeneBlazer); CFDA; CFP-Cyan Fluorescent Protein; CFP/YFP FRET; Chlorophyll; Chromornycin A; CL-NERF (Ratio Dye, pH); CMFDA; Coelenterazine f; Coelenterazine fcp; Coelenterazine Coelenterazine hcp; Coelenterazine ip; Coelenterazine n; Coelenterazine O; Coumarin Phalloidin; C-phycocyanine; CPM Methylcoumarin; CTC; CTC Formazan; Cy2™; Cy3.1 8; Cy3.5™; Cy3™; Cy5.1 8; Cy5.5™; Cy5™; Cy7™; Cyan OFF; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3; DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di-16-ASP); Dichlorodihydrofluorescein Diacetate (DCFH); DiD-Lipophilic Tracer; DID (DTIC 18(5)); DIDS; Dihydrorhodamine 123 (DHR); DiI (DiICl8(3)); Dinitrophenol; DiO (DiOCl8(3)); DiR; DiR (DiICl8(7)); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (III) chloride; EYFP; Fast Blue; FDA; Feulgen (Pararosaniline); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™; Fura Red™/Fluo-3; Fura-2; Fura-2/BCECF; Genacryl Brilliant Red B; Genacryl Brilliant Yellow 100F; Genacryl Pink 3G; Genacryl Yellow 50F; GeneBlazer (CCF2); GFP(S65T); GFP red shifted (rsGFP); GFP wild type, non-UV excitation (wtGFP); GFP wild type, WV excitation (wtGFP); GFPuv; Gloxalic Acid; Granular Blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1; Indodicarbocyanine (DiD); Indotricarbocyanine (DiR); Intrawhite Cf; JC-1; JO-JO-i; JO-PRO-1; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; Maxilon Brilliant Flavin 10 GFF; Maxilon Brilliant Flavin 8 OFF; Merocyanin; Methoxycournarin; Mitotracker Green FM; Mitotracker Orange; Mitotracker Red; Mitramycin; Monobromobimane; Monobromobimane (mBBr-GSH); Monochlorobirnane; MPS (Methyl Green. Pyridine Stilbene); NBD; NBD Amine; Nile Red; Nitrobenzoxadidole; Noradrenaline; Nuclear Fast Red; Nuclear Yellow; Nylosan Brilliant lavin E8G; Oregon Green; Oregon Green 488-X; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed [Red 613]; Phloxin B (Magdala Red); Phorwite AR; Phorwite BKL; Phorwite Rev; Phorwite RPA; Phosphine 3R; Phycoerythrin B [PE]; Phycoerythrin R [PE]; PKH26

(Sigma); PKH67; PMIA; Pontochrome Blue Black; POPO-1; POPO-3; PO-PRO-1; PO-PRO-3; Primuline; Procion Yellow; Propidium Iodid (PI); PyMPO; Pyrene; Pyronine; Pyronine B; Pyrozal Brilliant Flavin 7GF; QSY 7; Quinacrine Mustard; Red 613 [PE-TexasRed]; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BO; Rhodamine Green; Rhodamine Phalticidine; Rhodamine Phalloidine; Rhodamine Red; Rhodamine WT; Rose Bengal; R-phycocyanine; R-phycoerythrin (PE); RsGFP; S6SA; S65C; S65L; S65T; Sapphire GFP; SBFI; Serotonin; Sevron Brilliant Red 2B; Sevron Brilliant Red 4G; Sevron Brilliant Red B; Sevron Orange; Sevron Yellow L; SgBFP™; SgBFP™ (super glow BFP); SgGFP™; SgGFP™ (super glow GFP); SITS; SITS (Primuline); SITS (Stilbene Isothiosulphonic Acid); SNAFL calcein; SNAFL-1; SNAFL-2; SNARF calcein; SNARFI; Sodium Green; SpectrumAqua; SpectrumGreen; SpectrumOrange; Spectrum Red; SPQ (6-methoxy-N-(3-sulfopropyl)quinolinium); Stilbene; Sulphorhodamine B can C; Sulphorhodamine G Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TCN; Thiolyte; Thiozole Orange; Tinopol CBS (Calcofluor White); TMR; TO-PRO-1; TO-PRO-3; TO-PRO-5; TOTO-1; TOTO-3; TriColor (PE-Cy5); TRITC Tetramethyl Rodaminelso Thio Cyanate; True Blue; TruRed; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO-3; YOYO-1; and YOYO-3. As used herein, a "fluorophore" may include a salt of the fluorophore or a functionalized form of the fluorophore (e.g., where the fluorophore may include one or more of an amino group, a 2-chlorotrityl group, an oxime group, an amide group, or the like).

The disclosed salen compounds may be conjugated directly to the solid supports or fluorophores disclosed herein (which optionally may be functionalized) or may be conjugated via a linker compound. Suitable linker compounds may include acylating compounds such as anhydride compounds, and in particular acid anhydrides (e.g., glutaric anhydride).

The disclosed salen compounds may be prepared by reacting a reaction mixture comprising a 2-quinoxalinol compound, analog, or derivative having a formula:

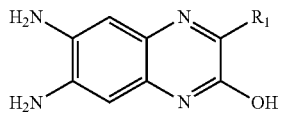

where $R_1$ is an amino acid side chain moiety; and a salicylic aldehyde analog or derivative having a formula:

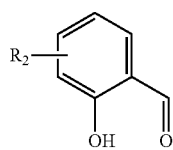

where $R_2$ is hydrogen, hydroxyl, $C_{1-6}$alkyl which may be straight chain or branched (e.g., 3-tert-butyl or 3,5-Di-tert butyl), $C_{1-6}$alkoxy which may be straight chain or branched, ether, or amine, thereby obtaining the salen compound. For example, in some embodiments the reaction mixture comprises about equal molar amounts of 2-quinoxalinol compound, analog, or derivative and salicylic aldehyde compound, analog, or derivative. In other embodiments, the reaction mixture comprises an excess amount of salicylic aldehyde compound, analog, or derivative (e.g., at least 2.5×, 5×, 7.5×, or 10× as much salicylic aldehyde compound, analog, or derivative as compared to 2-quinoxalinol compound, analog, or derivative.)

The reaction mixture further comprises a solvent. Suitable solvents may include alcohols (e.g., MeOH). The reaction mixture further may include an additional solvent such as dimethylformamide (DMF). The method may include applying heat to the reaction mixture (e.g., heating to at least about 60° C., 70° C. or 80° C., for at least about 6, 8, 10, or 12 hours).

The methods may include obtaining or isolating an intermediate compound having a formula:

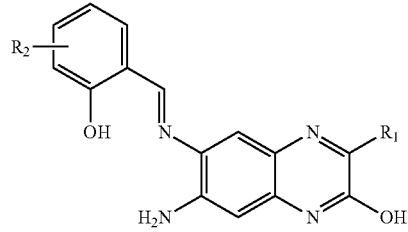

and reacting the intermediate in a reaction mixture with a salicylic aldehyde analog or derivative having a formula:

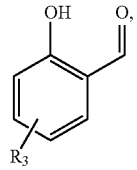

where $R_2$ and $R_3$ are hydrogen, hydroxyl, $C_{1-6}$alkyl which may be straight chain or branched (e.g., 3-tert-butyl or 3,5-Di-tert butyl), $C_{1-6}$alkoxy which may be straight chain or branched, ether, or amine. The substituents $R_2$ and $R_3$ may be the same or different, thereby obtaining a symmetrically or asymmetrically substituted salen compound, respectively. The reaction mixture further comprises a solvent. Suitable solvents may include alcohols (e.g., MeOH). The reaction mixture further may include an additional solvent such as dimethylformamide (DMF). The method may include applying heat to the reaction mixture (e.g., heating to at least about 60° C., 70° C. or 80° C., for at least about 6, 8, 10, or 12 hours).

Also disclosed are methods for detecting a cation in a solution, which may include detecting divalent metal cations such as $UO_2^{2+}$. The method may include (a) contacting the solution with a salen compound, which optionally may be conjugated to a solid support or a fluorophore, where if the solution comprises the cation, the compound forms a complex with the cation; and (b) detecting the complex in the solution.

In other embodiments, the methods for detecting a cation in a solution may include: (a) contacting the solution with complex comprising a complexed cation as disclosed herein, which complex optionally may be conjugated to a solid support or a fluorophore, where if the solution comprises the cation, the solution cation displaces the complexed cation from the compound and forms a new complex with the compound; and (b) detecting the new complex or detecting the displaced cation.

Detection methods for the complex (or new complex) or the displaced cation may include detecting a change in an absorption maximum for the solution via UV-Vis spectra analysis (e.g., where the uncomplexed compound exhibits a first absorption maximum and the complexed compound exhibits a second different absorption maximum). Detection methods for the complex (or new complex) or the displaced cation also may include detecting a change in fluorescence from the compound, complex, or optionally conjugated fluorophore (e.g., detecting a change in wavelength of absorbed or emitted light from the compound, complex, or optionally conjugated fluorophore when the complex is formed). Detection methods for the complex (or new complex) or the displaced cation also may include detecting a change in electrochemical properties of the solution (e.g., detecting a change in voltage of the solution if a complex is formed or if a complexed cation is displaced by a cation in solution).

In some embodiments, the formed complexes may be utilized as catalysts in chemical reactions. For example, the formed complexes may be utilized in oxidation reactions, which may include but are not limited to, oxidation reactions of methylenes aryl, allyl, vinyl, or any other α,β-unsaturated methylene), asymmetric epoxidation reactions, ring-opening reactions of epoxicles, oxidation reactions of amines, hydrolytic kinetic resolution (HKR), Hetero Diels-Alder reactions, Pictet-Spengler reactions, and hydrocyanation reactions. In some embodiments, methods for oxidizing compounds include reacting a methylene compound, an oxidizing agent, and a 2-quinoxalinol salen complex. As used herein, an "oxidizing agent" is any compound or material which is capable of removing an electron from a compound being oxidized. Suitable oxidizing agents include, but are not limited to, hydrogen peroxide, alkyl peroxides, peroxy acids, oxygen, and ozone. Optionally, the methylene compound to be oxidized may be may be substituted with one or more heteroatoms (e.g., N or O), or with one or more substituents (e.g., carbonyl, amino, formyl, ester, and nitro). Suitable methylene compounds may include, but are not limited to aryl methylene compounds.

EXAMPLES

The following EXAMPLES are illustrative and are not intended to limit the scope of the claimed subject matter.

Example 1

Reference is made to Wu et al., "An Efficient Method for Solution-Phase Parallel Synthesis of 2-Quinoxalinol Salen Schiff-base. Ligands," J. Comb. Chem., 2007, 9 (4), pp. 601-608, the content of which is incorporated herein by reference in its entirety.

Abstract and Introduction

A solution-phase parallel method for the synthesis of 2-quinoxalinol salen ligands was designed and optimized. The synthesis began with commercially available 1,5-difluoro-2,4-dinitrobenzene (DFDNB) and employed a sequence of five reaction steps. Laboratory techniques with low sensitivity to water or air for solution-phase parallel reactions were coupled with workup and purification procedures to give high-purity and yield a small ligand library of 20 compounds. The final step, a Schiff-base condensation of an aldehyde with the diaminoquinoxaline results in a new category of ligands for use in metal coordination or for use as potential bioagents, based on the skeleton 2,2'-(1E,1'E)-(quinoxaline-6,7-diyibis(azan-1-yl-1-ylidene))bis(methan-1-yl-1-ylidene)diphenol. The approach described here is adaptable for parallel synthesis of a larger size library. A solution-phase parallel method of synthesizing a 2-quinoxalinol salen ligands and a preparative library for a series of these ligands was demonstrated.

Results and Discussion

Synthesis began with the preparation of a 2-quinoxalinol precursor. (See, e.g., Zhang et al., J. Comb. Chem. 2004, 6, 431-436; and Wu et al., Molec. Diversity, 8: 165-174, 2004. Based on this previous work, the method for synthesizing diamino-2-quinoxalinols was further optimized. Here, scavenger resins as used in the previous investigations were replaced by the use of 2 equivalents of DIPEA (diisopropylethylamine) to remove the produced HF and HCl on the amino acid methyl group in the first step (Scheme 1).

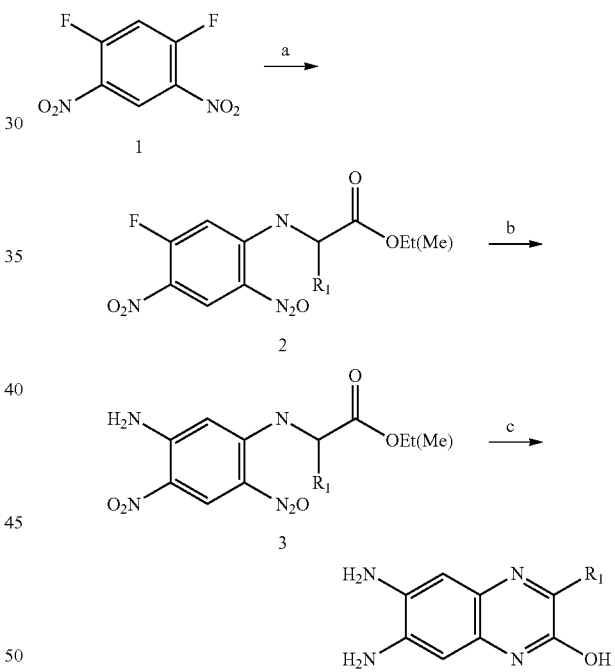

Scheme 1. Reaction route for synthesis of diamino-2-quinoxalinol a. THF, Amino acid, 1 eq, DIEPA, b. $NH_3 \cdot H_2O$, THF, c. PdC, $HCOONH_4$, EtOH 95%, $N_2$ Ammonium hydroxide in water (3 equiv.) was employed in the substitution of the second fluorine (Step 2, Scheme 1). In this way, the intermediate (3) does not require additional purification after substitution of the two fluorine atoms, because the remaining unreacted ammonium hydroxide and water can be removed using high vacuum. This serves both to simplify the process of parallel solution methods and reduce the costs of materials. After reduction by wet Pd on carbon, the target intermediates, diamino-2-quinoxalinols (4), were recrystallized from 95% ethanol. The purity and yield of each aim intermediate were very high (Table 1).

TABLE 1

Synthesis results of diamino-2-quinoxalinols.

| No. | Compound | R₁ | Purity (%)[‡] | $R_r$ (min) | Yield (%)[*] | mp (° C.) |
|---|---|---|---|---|---|---|
| 1 | 4a | 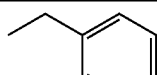 | 99 | 3.46 | 97 | 261.4~263.5 |
| 2 | 4b |  | 99 | 3.53 | 90 | 234.5~244.5 |
| 3 | 4c |  | 99 | 3.18 | 99 | 249.5~250.3 |
| 4 | 4d | 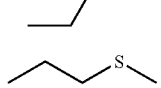 | 99 | 3.47 | 68 | >300 |

[‡]Identified by HPLC; $R_r$ is retention time.
[*]One step yield of Pd—C reduction.

Four different kinds of methyl amino acids were selected as the building blocks, including phenylalanine with an aromatic group, methionine containing a hetero atom (sulfur), and valine and leucine with alkyl groups at $R_1$. The yield of intermediate 4d (made from the methionine starting material) was lower than others. The aldehydes chosen included hydrophilic salicylaldehydes (di-hydroxide, 5a and 5b) and hydrophobic salicylaldehyde (mono- and di-tert-butyl, 5c and 5d) to build the library. The selected salicylic aldehydes provided a variety of compounds of varying solubility and coordination properties for the salen product in metal coordination chemistry or applications. (See Scheme 2.)

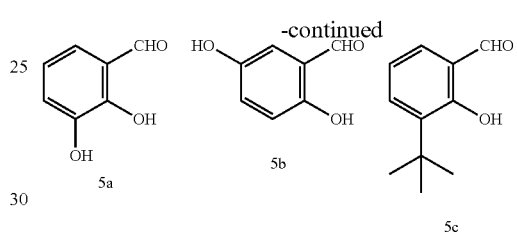

Condition: MeOH, $R_2$CHO (10 eqv), Refluxing, 48 hours.

Scheme 2. Reaction for synthesis of library of 2-quinoxalinol ligands.

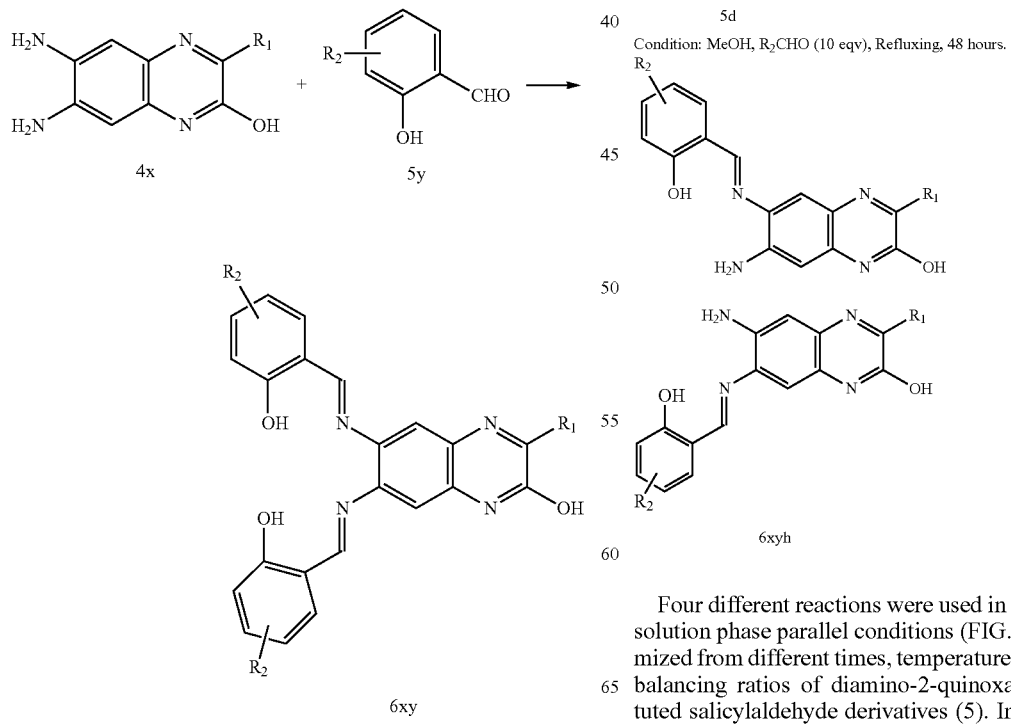

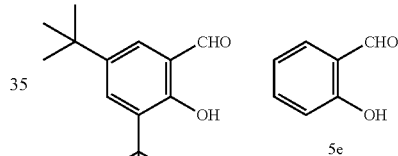

Four different reactions were used in order to optimize the solution phase parallel conditions (FIG. 1). These were optimized from different times, temperatures, solvents, as well as balancing ratios of diamino-2-quinoxalinols (4) to substituted salicylaldehyde derivatives (5). In some cases, microwave heating or sonication was applied for difficult reactions.

According to previously preparations of Schiff base compounds in the literature, methanol was selected as solvent, with a ratio of 1:2.5 of diamino-2-quinoxalinol (4) to salicylaldehyde derivative (5) at room temperature allowed to react for 48 hours. Under these conditions the desired products were not obtained. Upon heating from room temperature to reflux temperature the major product is the half-unit ligand 6cdh which has two possible structures and a small amount of the full unit targeted compound 6cd; small amounts of products Gad and with a high yield only of 6ae. Whichever of the potential isomeric products 6cdh is, there is another amino group which needs to be reacted with the salicylaldehyde derivative. Hence, the exact structure was not determined. The prolonging of reaction time from 48 hours to 72 hours did not result in additional full unit products nor did increasing the reaction temperature benefit the reaction progress. Changing the solvent from methanol to higher boiling point solvents (e.g., toluene, DMF and benzene) allowed for increasing the refluxing temperature, but did not produce the desired product. Both microwave and ultrasonic methods also were tried, but without success.

Finally, on increasing the ratio of salicylaldehyde derivative from 1:2.5 to 1:5 (FIG. 1), the yield of full unit target product went up from 20% to 31% for 6cd. The yields of 6ad and 6ae do not change dramatically. On increasing the ratio of to 1:7.5, the yields of target products increased to 52% for 6ad, 44% for 6cd and 60% for 6ae. The final products precipitated from methanol solution. This is useful for solution phase parallel synthesis and allows for the use of parallel filtration. When the ratio was increased from 1:7.5 to 1:10, the yield of 6cd and 6ae increased to 57% and 77% but the yields for 6ad did not change significantly. Continuing to increase the ratio did lead to better yields. The products were filtered directly resulting in yellow solids. These were washed with 95% ethanol and cold acetone 5 times each. It was determined that there was no final product in the filtered solution using TLC, and the yellow solids were pure full-unit ligand products. These were characterized by $^1$H-NMR, $^{13}$C-NMR, MS and HRMS. The purity of 6ad, 6cd and 6ae identified by $^1$H-NMR was no less than 99%. For 6da, at the ratio of 1:10 of 4d to 5a, the aim product 6da was not obtained, but when the reaction concentration was increased by reducing the volume of solvent of methanol, under the ratio of 1:10, a relatively high yields of 6da (65%) was obtained.

The final tested condition was a ratio of 1:10 (diamino-2-quinoxalinol to salicylaldehyde derivative) which was reacted for 48 hours at reflux temperature in a solution of methanol. When this was synthesized as a 4×5 library, the procedure was found to be suitable for the solution phase parallel synthesis of 2-quinoxalinol Schiff base ligands. The results are shown on Table 2, which illustrates that all of the twenty targeted products were synthesized by parallel methods with high yield and purity.

TABLE 2

Synthesis results of 2-quinoxalinol Schiff base ligands library.

| No. | Product | $R_1$ | $R_2$ | Purity (%)[†] | Yield (%)[¶] | mp (° C.) |
|---|---|---|---|---|---|---|
| 1 | 6aa | 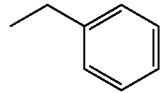 | 3-OH | >90 | 50 | 251.0* |
| 2 | 6ab | 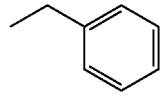 | 5-OH | >95 | 41 | 246.0* |
| 3 | 6ac | 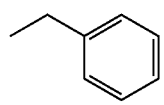 | 3-tert-butyl | >95 | 55 | 271.0-273.5 |
| 4 | 6ad | 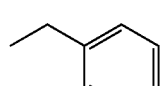 | 3,5-Di-tert-butyl | >99 | 56 | 279.1-280.1 |
| 5 | 6ae | 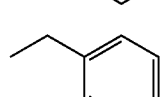 | H | >99 | 77 | 264.1-266.1 |
| 6 | 6ba |  | 3-OH | >90 | 64 | >300.0 |
| 7 | 6bb |  | 5-OH | >95 | 44 | 221.5* |
| 8 | 6bc |  | 3-tert-butyl | >99 | 56 | 285.1-286.1 |

TABLE 2-continued

Synthesis results of 2-quinoxalinol Schiff base ligands library.

| No. | Product | $R_1$ | $R_2$ | Purity (%)[†] | Yield (%)[¶] | mp (° C.) |
|---|---|---|---|---|---|---|
| 9 | 6bd |  | 3,5-Di-tert-butyl | >99 | 55 | 280.0-281.0 |
| 10 | 6be |  | H | >90 | 70 | 288.5-289.3 |
| 11 | 6ca |  | 3-OH | >95 | 50 | 260.0-261.5 |
| 12 | 6cb |  | 5-OH | >90 | 67 | 290.5* |
| 13 | 6cc |  | 3-tert-butyl | >95 | 52 | 285.1-286.7 |
| 14 | 6cd |  | 3,5-Di-tert-butyl | >99 | 57 | 287.8-288.8 |
| 15 | 6ce |  | H | >99 | 86 | 286.5-288.5 |
| 16 | 6da |  | 3-OH | >90 | 65 | >300.0 |
| 17 | 6db | 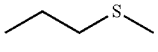 | 5-OH | >90 | 57 | >300.0 |
| 18 | 6dc | 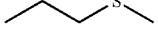 | 3-tert-butyl | >95 | 46 | 262.0* |
| 19 | 6dd | 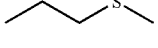 | 3,5-Di-tert-butyl | >99 | 56 | 286.0-287.5 |
| 20 | 6de | 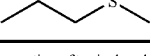 | H | >95 | 81 | 270.5* |

[†]Identified by the proportion of typical peak areas of $^1$H-NMR, assuming the half unit Schiff base ligand is the only major byproduct. HPLC can not identify the exact percentage of this major impurity because the large difference of absorbance of their UV (254 or 214 nm).
[¶]Indicates a one-step yield from diamino-2-qunioxalinol 4 to final product 6.
*At this temperature, these compounds were found to decompose.

Conclusion

A 2-quinoxalinol salen (or Schiff-base) ligand library was prepared by an efficient solution phase parallel method. It was found that these organic ligands are stable at high temperature (<200° C.) and not sensitive to oxygen, water, alkaline conditions or most solvents. In the process, the synthetic method for the key intermediate quinoxaline was further optimized from methods used in previous reports.

From the resulting yields under the optimized conditions, some trends are clear. With each quinoxaline, the yield of the product with aldehyde 5e was significantly higher most likely due to limited steric hindrance, but yields were quite good with using aldehyde 5d, which should be the most sterically hindered aldehyde. This is also the aldehyde with the best solubility and products from this aldehyde are soluble in chlorinated solvents, whereas some of the compounds synthesized from aldehyde 5a and 5b are soluble only in DMSO. The most likely causes of the inhibition of product formation in reactions with aldehyde 5b are hydrogen bonding or an unfavorable transition state.

Experimental

All amino acid methyl esters, DFDNB, HCl (37%) and aldehydes were purchased from Acros Organics Co. Ammonium hydroxide (5.0 N), palladium on carbon (wet, 5%) were purchased from Sigma-Aldrich Co. Starting materials were used as received. All organic solvents were obtained from Thermo Fisher Scientific Co. and were directly used for synthesis. HPLC analysis was performed on a Shimadzu™ apparatus equipped with a SPD-10A VP detector. Solutions for HPLC were eluted as 50/50 acetonitrile/$H_2O$ with a buffer consisting of 0.05% TFA over 10 min at 1 mL/min with detection by UV at 254 nm. The column employed was a water $C^{18}$ column (w33471F, 3.9×300 mm) from DIKMA Co. All melting points were recorded on a MeI-temp 11 melting point apparatus, and the values were uncorrected. $^1$H and $^{13}$C NMR spectra were recorded on Bruker™ AC 250 spectrometer (operated at 250 and 62.5 MHz, respectively) or Bruker™ AV 400 spectrometer (operated at 400 and 100 MHz, respectively). Chemical shifts are reported as δ (ppm). Some $^1$H-NMR data were collected using DMSO-d$^6$ and CDCl$_3$ to dissolve samples because they were not completely soluble only in DMSO-d$^6$; however, if just CDCl$_3$ is used, the active protons do not appear in D$_2$O/water exchange experiments. The solvents used are indicted in the experimental details. Reaction progress was monitored by thin-layer chromatography (TLC) using 0.25 mm Whatman™ Aluminum silica gel 60-F254 precoated plates with visualization by irradiation with a Mineralight™ UVGL-25 lamp. The parallel synthesis was carried out on a Corning™ parallel synthesizer. Electrospray ionization mass spectrometry was performed on a Micromass QTOF™ mass spectrometer (Waters Corp, Milford Mass.). Direct probe samples were on a VG-70S mass spectrometer (Waters Corp, Milford Mass.). All UV data was collected using a Cary 50 UV-Vis spectrophotometer with a xenon lamp and an equipment range from 200 to 1250 nm. IR spectroscopic data was collected using a Shimsdzu™ IR, Prestige-21 Fourier Transform Infrared Spectrophotometer and KBr solid samples. Samples for melting point, IR, and UV, were purified by recrystallization or—flash column chromatography of the final 2-quinoxalinol products.

General Procedure

To a stirring solution of 150 mL of THF, 1.0 equivalent (10.0 mmol) of 1,5-difluoro-2,4-dinitrobenzene (DFDNB), 2.2 equivalents (22 mmol) of diisopropylethylamine (DIPEA), and 1.0 equivalent methyl amino acid (10 mmol) were added. The reaction mixture was stirred continuously for 12 hours at room temperature. After it was confirmed by TLC that the starting materials (DFDNB) had been consumed, 3 equiv (30 mmol) of ammonium hydroxide in water was added as 5.0N in aqueous solution to the reaction mixture. The reaction solution was stirred at room temperature for an additional 5 hours until the reaction was complete and this was confirmed by TLC. The reaction solution was concentrated to dryness using a rotary evaporator resulting in a yellow oil or oily solid. The resultant yellow oil was dissolved in 100 mL of ethanol (95%) with stirring. To this, HCOONH$_4$, 20 equiv., (0.2 mol) and 5% wet Pd—C (3.1 g, 7.0 g for containing sulfur, catalytic) were added under a protective N$_2$ atmosphere. The reaction mixture was heated to reflux temperature for 15-30 minutes. During this time, the reaction mixture changed the initial yellow to red and then to fluorescent yellow. After this time, the catalyst Pd—C and unreacted HCOONH$_4$ were filtered from the solution. The filtrate was put into freezer (0° C.) for 48-72 hours until yellow crystals form. If there is no solids precipitate from the solution, sonication using an ultrasonic bath can help precipitate the diamino-2-quinoxalinols intermediate as a solid, Filtration of the solid from the reaction solution results in highly pure diamino-2-quinoxalinols intermediate. The synthetic yield from starting material of 4a, 4b, 4c and 4d were 60%, 59%, 58% and 41%, respectively. After drying on high vacuum, HPLC, $^1$H-NMR and $^{13}$C-NMR show the purity of each of these are not less than 98%.

To 1.0 equiv (0.1 mmol) of the diamino-2-quinoxalinol intermediate dissolved in 4 mL methanol, a solution of 10.0 equiv (1 mmol) aldehyde derivatives in 6 mL methanol was added. The two were combined with stirring, and after heating to reflux temperature for hour, the reaction mixture becomes deep yellow or dark. After continued heating at reflux temperature for 48 hours, product forms and precipitates as either dark yellow or red solids. The precipitate was filtered directly and washed with 95% ethanol and cold acetone 5 times each to obtain the 2-quinoxalinols Schiff base ligands as the final product. The yield of final products ranges from 40% to 80% with the purity of them ranging from 90.0% to 99.0%. All of the final products were identified and characterized by $^1$H-NMR, $^{13}$C-NMR, MS, HRMS, UV-Vis and IR.

For synthesis of 6aa, 6ea and 6db, 1.0 equiv (0.1 mmol) of diamino-2-quinoxalinols intermediates was dissolved into 4 mL methanol and 10.0 equiv (1 mmol) aldehyde derivates was dissolved into 2 mL methanol. Under stirring, mixer solution becomes red after refluxing 40 min. After refluxing for 48 hours, a red precipitate formed. This was filtered directly and washed with 95% ethanol and cold acetone 5 times each to obtain product.

4a $^1$H-NMR (400 MHz DMSO-d$^6$): δ 3.99 (s, 2H), 4.66 (bs, 2H), 5.47 (bs, 2H), 6.37 (s, 1H), 6.80 (s, 1H), 7.16-7.31 (m, 5H), 11.86 (bs, 1H). $^{13}$C-NMR (100 MHz, DMSO-d$^6$): δ 155.1, 152.2, 140.5, 139.4, 133.0, 129.4, 128.6, 126.4, 125.8, 111.0, 96.8, 38.8. Formula: C$_{15}$H$_{14}$N$_4$O. MS (M+H): 267.0. HRMS: found (267.1256), calc (267.1240). IR: 3172.9 cm$^{-1}$ (bs), 3381.2 cm$^{-1}$(bs), 3182.6 cm$^{-1}$(bs), 3005.2 cm$^{-1}$, 1645.3 cm$^{-1}$, 1510.3 cm$^{-1}$, 1402.3 cm$^{-1}$, 1278.8 cm$^{-1}$. UV: 402.9 nm (bs).

4b $^1$H-NMR (400 MHz DMSO-d$^6$): δ 1.13 (d, J=6.8, 6H), 3.33 (sept, 1H), 4.66 (bs, 2H), 5.36 (bs, 2H), 6.33 (s, 1H), 6.78 (s, 1H), 11.73 (bs, 1H). $^{13}$C-NMR (100 MHz, DMSO-d$^6$): δ 157.7, 154.7, 140.1, 132.8, 125.9, 125.5, 111.3, 96.9, 29.7, 21.0. Formula: C$_{11}$H$_{14}$N$_4$O. MS (M+H): 219.0. HRMS: found (219.1248), calc (219.1246). IR: 3381.2 cm$^{-1}$ (bs), 3365.1 cm$^{-1}$(bs), 2962.7 cm$^{-1}$, 2929.9 cm$^{-1}$, 1656.9 cm$^{-1}$, 1512.2 cm$^{-1}$, 1406.1 cm$^{-1}$, 1273.0 cm$^{-1}$. UV: 394.0 nm (bs).

4c $^1$H-NMR (250 MHz DMSO-d$^6$): δ 0.90 (d, J=6.7, 6H), 2.15 (m, 1H), 2.50 (d, 2H), 4.62 (bs, 2H), 5.39 (bs, 2H), 6.35 (s, 1H), 6.79 (s, 1H), 11.98 (bs, 1H). $^{13}$C-NMR (62.5 MHz, DMSO-d$^6$): δ155.4, 153.2, 140.1, 132.8, 126.0, 125.8, 111.2, 96.9, 41.7, 26.9, 23.0. Formula: C$_{12}$H$_{16}$H$_4$O. MS (M+H): 233.0. HRMS: found (233.1410), calc (233.1402). IR: 3352.3 cm$^{-1}$(bs), 32771 cm$^{-1}$(bs), 2949.2 cm$^{-1}$, 2868.2 cm$^{-1}$, 2818.0 cm$^{-1}$, 1653.0 cm$^{-1}$, 1512.2 cm$^{-1}$, 1419.6 cm$^{-1}$, 1402.3 cm$^{-1}$, 1271.1 cm$^{-1}$. UV: 410.6 nm (bs), 299.1 (wbs).

4d $^1$H-NMR (400 MHz DMSO-d$^6$): δ 2.09 (s, 3H), 2.83 (t, 2H), 2.95 (t, 2H), 5.19 (bs, 2H), 5.65 (bs, 2H), 6.39 (s, 1H), 6.82 (s, 1H), 11.99 (bs, 1H), $^{13}$C-NMR (100 MHz, DMSO-d$^6$): δ 155.2, 151.8, 140.4, 132.9, 126.2, 125.8, 111.1, 96.9, 32.9, 31.1, 15.1. Formula: C$_{11}$H$_{14}$N$_4$OS. MS (M+H): 251.0. HRMS: found (251.0966), calc (251.0963). IR: 3321.4 cm$^{-1}$ (bs), 3219.2 cm$^{-1}$(bs), 2920.2 cm$^{-1}$, 2879.7 cm$^{-1}$, 1643.4 cm$^{-1}$, 1510.3 cm$^{-1}$, 1402.3 cm$^{-1}$, 1273.0 cm$^{-1}$. UV: 391.0 nm (bs).

6aa $^1$H-NMR (400 MHz DMSO-d$^6$): δ 4.14 (s, 2H), 6.77-7.34 (m, 12H), 7.87 (s, 1H), 8.83 (s, 1H), 9.04 (s, 1H), 9.22 (bs, 1H, D$_2$O exchangeable), 9.41 (bs, 1H, D$_2$O exchangeable), 12.18 (bs, 1H, D$_2$O exchangeable), 12.53 (bs, 1H, D$_2$O exchangeable), 12.99 (bs, 1H, D$_2$O exchangeable). $^{13}$C-NMR (100 MHz, DMSO-d$^6$): δ 165.6, 164.8, 160.7, 154.9, 150.0, 1493, 146.2, 146.1, 145.7, 138.2, 137.9, 132.1, 129.7, 128.8, 126.9, 123.4, 122.9, 120.3, 120.2, 119.8, 119.6, 118.4, 106.0, 40.0. Formula: C$_{29}$H$_{22}$N$_4$O$_5$. MS: 507.0. HRMS: found (507.1666), calc (507.1668). IR: 3392.8 cm$^{-1}$(bs), 3005.2 cm$^{-1}$, 1656.8 cm$^{-1}$, 1616.3 cm$^{-1}$, 1467.8 cm$^{-1}$, 1271.1 cm$^{-1}$, 1234.4 cm$^{-1}$. UV: 383.0 nm (bs).

6ab $^1$H-NMR (400 MHz DMSO-d$^6$): δ 4.14 (s, 2H), 6.74-7.35 (m, 12H), 7.87 (s, 1H), 834 (s, 1H), 8.97 (s, 1H), 9.08 (bs, M, D$_2$O exchangeable), 9.12 (bs, 1H, D$_2$O exchangeable), 11.43 (bs, 1H, D$_2$O exchangeable), 12.31 (bs, 1H, D$_2$O exchangeable), 12.50 (bs, 1H, D$_2$O exchangeable). $^{13}$C-NMR (100 MHz, DMSO-d$^6$): δ 164.3, 163.8, 160.6, 155.0, 153.8, 153.5, 150.2, 150.0, 146.5, 138.0, 137.9, 132.1, 131.1, 129.7, 128.9, 126.9, 122.4, 121.7, 120.2, 119.9, 118.1, 117.9, 117.7, 117.5, 116.5, 105.9, 40.0. Formula: $C_{29}H_{22}N_4O_5$. MS (M+H): 507.0. HRMS: found (507.1667), calc (507.1668), IR: 3387.0 cm$^{-1}$(bs), 3005.0 cm$^{-1}$, 1662.6 cm$^{-1}$, 1616.4 cm$^{-1}$, 1573.9 cm$^{-1}$, 1487.1 cm$^{-1}$, 1282.7 cm$^{-1}$, 1153.4 cm$^{-1}$. UV: 378.0 nm (bs).

6ac $^1$H-NMR (400 MHz DMSO-d$^6$): δ 1.31 (s, 9H), 1.34 (s, 9H), 4.15 (s, 2H), 6.77-7.44 (m, 12H), 7.62 (s, 1H), 8.58 (s, 1H), 8.70 (s, 1H), 12.26 (bs, 1H), 13.42 (bs, 1H), 13.60 (bs, 1H). $^{13}$C-NMR (100 MHz, DMSO-d$^6$): δ 165.4, 163.7, 160.6, 160.4, 155.1, 144.6, 138.4, 137.7, 137.4, 137.0, 133.9, 131.9, 1313, 130.7, 129.3, 128.2, 126.4, 126.1, 119.2, 118.9, 118.7, 118.2, 117.9, 105.5, 34.7, 29.2. Formula: $C_{37}H_{48}N_4O_3$. MS (M+H): 587.0. HRMS: found (587.3028), calc (587.3022). IR: 3437.2 cm$^{-1}$(bs), 3417.9 cm$^{-1}$(bs), 2953.0 cm$^{-1}$, 2912.5 cm$^{-1}$, 1672.3 cm$^{-1}$, 1606.7 cm$^{-1}$, 1500.6 cm$^{-1}$, 1431.2 cm$^{-1}$, 1394.5 cm$^{-1}$, 1197.8 cm$^{-1}$, 1143.8 cm$^{-1}$. UV: 285.7 nm (bs), 387.9 nm (bs).

6ad $^1$H-NMR (250 MHz DMSO-d$^6$ and CDCl$_3$): δ 1.23 (s, 18H), 1.32 (s, 9H), 1.34 (s, 9H), 4.14 (s, 2H), 7.01 (s, 1H), 7.12-7.41 (m, 9H), 7.59 (s, 1H), 8.58 (s, 1H), 8.68 (s, 1H), 12.22 (bs, 1H), 13.25 (bs, 1H), 13.36 (bs, 1H). $^{13}$C-NMR (62.5 MHz, DMSO-d$^6$ and CDCl$_3$): δ 165.9, 1643, 160.2, 158.6, 158.3, 155.3, 144.9, 140.6, 140.5, 138.9, 137.2, 137.1, 136.9, 131.7, 131.5, 129.5, 128.7, 128.4, 128.2, 1272, 127.0, 126.5, 118.4, 118.1, 118.1, 105.6, 35.1, 34.1, 31.5, 29.4. Formula: $C_{45}H_{54}N_4O_3$, MS (M+H): 699.0. HRMS: found (699.4276), calc (699.4274). IR: 3435.2 cm$^{-1}$(bs), 3415.9 cm$^{-1}$(bs), 2956.9 cm$^{-1}$, 2910.6 cm$^{-1}$, 2873.9 cm$^{-1}$, 1656.9 cm$^{-1}$, 1612.5 cm$^{-1}$, 1529.6 cm$^{-1}$, 1477.5 cm$^{-1}$, 1442.8 cm$^{-1}$, 1261.5 cm$^{-1}$, 1168.9 cm$^{-1}$. UV: 299.1 nm (bs), 390.9 nm (bs).

6ae $^1$H-NMR (400 MHz DMSO-d$^6$): δ 4.17 (s, 2H), 6.95-7.03 (m, 2H), 7.11 (s, 1H), 7.25-7.49 (m, 7H), 7.66 (d, 1H), 7.79 (d, 1H), 7.94 (5, 1H), 8.90 (s, 1H), 9.13 (s, 1H), 12.28 (bs, 1H), 12.57 (bs, 1H), 13.13 (bs, 1H). $^{13}$C-NMR (100 MHz, DMSO-d$^6$): δ 164.6, 164.0, 160.9, 160.8, 160.6, 155.0, 146.0, 138.1, 137.9, 134.5, 133.8, 133.1, 132.3, 132.2, 131.2, 129.8, 128.9, 126.9, 120.2, 120.0, 119.9, 119.6, 118.1, 117.2, 117.1, 105.8, 40.0. Formula: $C_{29}H_{22}N_4O_3$. MS (M+H): 475.0. HRMS: found (475.1762), calc (475.1770). IR: 3448.7 cm$^{-1}$ (bs), 3427.5 cm$^{-1}$(bs), 3055.2 cm$^{-1}$, 3030.2 cm$^{-1}$, 1654.9 cm$^{-1}$, 1610.6 cm$^{-1}$, 1570.1 cm$^{-1}$, 1481.3 cm$^{-1}$, 1276.9 cm$^{-1}$, 1197.8 cm$^{-1}$. UV: 305.6 nm (wbs), 335.9 nm (wbs), 390.5 nm (bs).

6ba $^1$H-NMR (400 MHz DMSO-d$^6$): δ 1.26 (d, J=6.8 Hz, 6H), 3.50 (sept, 1H), 6.80 (t, 1H), 6.84 (t, 1H), 6.94 (d, 1H), 6.99 (d, 1H), 7.01 (s, 1H), 7.14 (d, 1H), 7.22 (d, 1H), 7.92 (s, 1H), 8.87 (s, 1H), 9.11 (s, 1H), 9.24 (bs, 1H), 9.43 (bs, 1H), 12.24 (bs, 1H), 12.48 (bs, 1H), 13.06 (bs, 1H). $^{13}$C-NMR (100 MHz, DMSO-d$^6$): δ 166.0, 165.6, 164.8, 154.6, 150.0, 149.7, 146.2, 146.1, 145.4, 138.1, 131.8, 131.1, 123.5, 122.9, 120.3, 120.2, 120.0, 119.6, 119.2, 118.3, 106.0, 30.4, 20.6. Formula: $C_{25}H_{22}N_4O_5$. MS (M+11): 459.0. HRMS: found (459.1675), calc (459.1668). IR: 3421.7 cm$^{-1}$(bs), 3059.1 cm$^{-1}$, 2966.5 cm$^{-1}$, 2926.0 cm$^{-1}$, 1656.9 cm$^{-1}$, 1616.4 cm$^{-1}$, 1556.6 cm$^{-1}$, 1465.9 cm$^{-1}$, 1373.3 cm$^{-1}$, 1273.0 cm$^{-1}$, 1230.6 cm$^{-1}$. UV: 306.5 nm (bs), 389.6 nm (bs).

6bb $^1$H-NMR (400 MHz DMSO-d$^6$): δ 1.23 (d, J=6.8 Hz, 6H), 3.48 (sept, 1H), 6.74-7.1.2 (m, 7H), 7.88 (s, 1H), 8.74 (s, 1H), 9.01 (s, 1H), 9.08 (bs, 114, D$_2$O exchangeable), 9.13 (bs, 1H, D$_2$O exchangeable), 11.46 (bs, 1H, D$_2$O exchangeable), 12.36 (bs, 1H, D$_2$O exchangeable), 12.42 (bs, 1H, D$_2$O exchangeable). $^{13}$C-NMR (100 MHz, DMSO-d$^6$): δ 165.9, 164.3, 163.8, 154.6, 153.8, 153.5, 150.2, 150.0, 146.2, 138.2, 131.8, 130.9, 122.3, 121.7, 120.2, 120.0, 118.0, 117.9, 117.6, 116.5, 105.8, 30.4, 20.6. Formula: $C_{25}H_{22}N_4O_5$. MS (M+H): 458.0. HRMS: found (459.1665), colt (4591668). IR: 3400.5 cm$^{-1}$(bs), 2962.7 cm$^{-1}$, 2926.0 cm$^{-1}$, 1656.9 cm$^{-1}$, 1627.9 cm$^{-1}$, 1579.7 cm$^{-1}$, 1490.8 cm$^{-1}$, 1400.0 cm$^{-1}$, 1273.0 cm$^{-1}$, 1219.0 cm$^{-1}$. UV: 299.1 nm (bs), 387.0 nm (bs).

6bc $^1$H-NMR (400 MHz DMSO-d$^6$): δ 1.27 (d, J=6.8 Hz, 6H), 1.37 (s, 9H), 1.42 (s, 9H), 3.52 (sept, 1H), 6.93 (t, 1H), 6.95 (t, 1H), 7.20 (s, 1H), 7.38 (d, 1H), 7.44 (d, 1H), 7.54-7.58 (1, 2H), 8.00 (s, 1H), 8.94 (s, 1H), 9.19 (s, 1H), 12.51 (bs, 1H), 13.73 (bs, 1H), 14.04 (bs, 1H). $^{13}$C-NMR (100 MHz, DMSO-d$^6$): δ 167.1, 166.3, 165.5, 160.5, 160.4, 154.6, 144.5, 137.9, 137.6, 137.1, 137.0, 132.2, 132.0, 131.4, 131.3, 130.8, 119.7, 119.4, 119.1, 118.9, 118.3, 105.9, 34.9, 30.4, 29.7, 20.6. Formula: $C_{33}H_{38}N_4O_3$, MS (M+H): 539.0. HRMS: found (539.3024), calc (539.3022). IR: 3429.4 cm$^{-1}$(bs), 2956.9 cm$^{-1}$, 2872.0 cm$^{-1}$, 1660.7 cm$^{-1}$, 1606.7 cm$^{-1}$, 1467.8 cm$^{-1}$, 1431.2 cm$^{-1}$, 1388.8 cm$^{-1}$, 1270.0 cm$^{-1}$, 1199.7 cm$^{-1}$. UV: 302.2 nm (bs), 386.2 nm (bs).

6bd $^1$H-NMR (400 MHz DMSO-d$^6$ and CDCl$_3$): δ 1.20 (s, 9H), 1.21 (s, 9H), 1.21 (d, J=6.8 Hz, 6H), 1.29 (s, 9H), 1.32 (s, 9H), 3.52 (sept, 1H), 6.99 (s, 1H), 7.17 (s, 2H), 7.34 (s, 1H), 7.37 (s, 1H), 7.62 (s, 1H), 8.59 (s, 1H), 8.72 (s, 1H), 12.12 (bs, 1H), 13.28 (bs, 1H), 13.39 (bs, 1H). $^{13}$C-NMR (100 MHz, DMSO-d$^6$ and CDCl$_3$): 165.9, 165.7, 1641, 158.5, 158.3, 155.1, 144.5, 140.5, 140.4, 138.8, 137.1, 136.9, 131.5, 131.2, 128.6, 128.1, 127.1, 126.8, 118.3, 118.1, 118.0, 105.4, 35.0, 34.1, 31.4, 30.3, 29.3, 20.1. Formula: $C_{41}H_{54}N_4O_3$. MS (M+H): 651.0. HRMS: found (651.4274), calc (651.4268). IR: 3423.7 cm$^{-1}$(bs), 2958.8 cm$^{-1}$, 2910.6 cm$^{-1}$, 2870.1 cm$^{-1}$, 1653.0 cm$^{-1}$, 1614.4 cm$^{-1}$, 1581.6 cm$^{-1}$, 1469.8 cm$^{-1}$, 1437.0 cm$^{-1}$, 1390.7 cm$^{-1}$, 1363.7 cm$^{-1}$, 1253.7 cm$^{-1}$, 1203.6 cm$^{-1}$. UV: 299.6 nm (bs), 387.9 nm (bs).

6be $^1$H-NMR (400 MHz DMSO-d$^6$): δ 1.23 (d, J=6.8 Hz, 6H), 3.47 (sept, 6.91-7.00 (m, 4H), 7.08 (s, 1H), 7.39 (t, 1H), 7.44 (t, 1H), 7.66 (d, 1H), 7.76 (d, 1H), 7.93 (s, 1H), 8.87 (s, 1H), 9.15 (s, 1H), 12.28 (bs, 1H), 12.46 (bs, 1H), 13.14 (bs, $^{13}$C-NMR (100 MHz, DMSO-d$^6$): δ 166.1, 164.6, 163.9, 160.9, 160.6, 154.6, 145.7, 137.9, 134.4, 133.8, 133.1, 132.4, 132.0, 131.1, 120.2, 119.8, 119.5, 118.1, 117.2, 117.1, 105.7, 30.4, 20.6. Formula: $C_{25}H_{22}N_4O_3$. MS (M+H): 427M. HRMS: found (427.1764), calc (427.1770). IR: 3441.0 cm$^{-1}$ (bs), 2964.6 cm$^{-1}$, 2924.1 cm$^{-1}$, 1658.8 cm$^{-1}$, 1616.4 cm$^{-1}$, 1570.1 cm$^{-1}$, 1479.4 cm$^{-1}$, 1452.0 cm$^{-1}$, 1278.8 cm$^{-1}$, 1203.6 cm$^{-1}$. UV: 335.9 nm (bs), 387.9 nm (bs).

6ca $^1$H-NMR (400 MHz DMSO-d$^6$): δ 1.23 (d, J=6.6 Hz, 6H), 2.27 (m, 1H), 2.71 (d, J=7.0, 2H), 6.80 (t, 1H), 6.83 (t, 1H), 6.95 (d, 1H), 7.00 (d, 1H), 7.09 (s, 1H), 7.14 (t, 2H), 7.22 (1, 2H), 7.92 (s, 1H), 8.87 (s, 1H), 9.08 (s, 1H), 9.24 (bs, 1H, D$_2$O exchangeable), 9.42 (bs, 1H, D$_2$O exchangeable), 12.25 (bs, 1H, D$_2$O exchangeable), 12.47 (bs, 1H, D$_2$O exchangeable), 13.04 (bs, 1H, D$_2$O exchangeable). $^{13}$C-NMR (100 MHz, DMSO-d$^6$): δ 165.6, 164.7, 161.7, 155.2, 150.0, 149.7, 146.2, 146.1, 145.4, 138.1, 131.9, 131.2, 123.4, 122.9, 120.3, 120.2, 120.0, 119.6, 119.2, 118.3, 106.0, 42.1, 26.6, 23.1. Formula: $C_{26}H_{24}N_4O_5$, MS (M+H): 473.0. HRMS: found (473.1818), calc (473.1825). IR: 3419.8 cm$^{-1}$(bs), 2949.2 cm$^{-1}$, 2866.2 cm$^{-1}$, 1656.9 cm$^{-1}$, 1618.3 cm$^{-1}$, 1579.7 cm$^{-1}$, 1465.9 cm$^{-1}$, 1373.3 cm$^{-1}$, 1271.1 cm$^{-1}$, 1232.5 cm$^{-1}$. UV: 301.3 nm (bs), 381.0 nm (bs).

6cb $^1$H-NMR (400 MHz DMSO-d$^6$): δ 0.98 (d, J=6.6 Hz, 6H), 2.27 (m, 1H), 2.71 (d, J=7.0, 2H), 6.77-6.91 (m, 4H), 7.06 (s, 2H), 7.14 (s, 1H), 7.92 (s, 1H), 8.77 (s, 1H), 9.01 (s, 1H), 9.12 (bs, 1H), 9.15 (bs, 1H), 11.49 (bs, 1H), 12.36 (bs, 1H), 12.45 (bs, 1H). $^{13}$C-NMR (100 MHz, DMSO-d$^6$): δ 164.4, 163.7, 161.5, 155.2, 153.8, 153.5, 150.2, 150.0, 146.2, 138.2, 131.9, 131.1, 120.2, 119.9, 117.6, 117.5, 116.5, 105.8, 42.1, 26.7, 23.1. Formula: $C_{26}H_{24}N_4O_5$. MS (M+H): 473.0. HRMS: found (473.1832), calc (473.1825). IR: 3427.5 cm$^{-1}$ (bs), 3412.1 cm$^{-1}$(bs), 2956.9 cm$^{-1}$, 2924.1 cm$^{-1}$, 1658.8 cm$^{-1}$, 1618.3 cm$^{-1}$, 1577.8 cm$^{-1}$, 1483.3 cm$^{-1}$, 1379.1 cm$^{-1}$, 1286.5 cm$^{-1}$, 1213.2 cm$^-$. UV: 303.9 nm (bs), 395.7 nm (bs).

6cc $^1$H-NMR (400 MHz DMSO-d$^6$): δ 0.99 (d, J=6.6 Hz, 61H), 13.7 (s, 9H), 1.42 (s, 9H), 2.29 (m, 1H), 2.72 (d, 2H), 6.93 (t, 1H), 6.95 (t, 1H), 7.20 (s, 1H), 7.38 (d, 1H), 7.44 (d, 1H), 7.53-7.58 (m, 2H), 8.01 (s, 1H), 8.93 (s, 1H), 9.16 (s, 1H), 12.51 (bs, 1H), 13.73 (bs, 1H), 14.03 (bs, 1H). $^{13}$C-NMR (100 MHz, DMSO-d$^6$): δ 167.1, 165.5, 161.9, 160.5, 160.4, 1552, 144.5, 137.9, 137.2, 137.0, 132.2, 132.0, 131.9, 131.4, 130.8, 119.7, 119.4, 119.1, 118.9, 118.2, 105.9, 42.1, 34.9, 29.7, 26.6, 211. Formula: $C_{34}H_{40}N_4O_3$. MS (M+H): 553.0, HRMS: found (553.3177), cab (553.3178). IR: 3423.7 cm$^{-1}$ (bs), 2955.0 cm$^{-1}$, 2918.3 cm$^{-1}$, 2870.1 cm$^{-1}$, 1662.6 cm$^{-1}$, 1604.8 cm$^{-1}$, 1573.9 cm$^{-1}$, 1496.8 cm$^{-1}$, 1469.8 cm$^{-1}$, 1431.2 cm$^{-1}$, 1396.5 cm$^{-1}$, 1273.0 cm$^{-1}$, 1199.7 cm$^{-1}$. UV: 299.6 nm (bs), 382.7 nm (bs).

6cd $^1$H-NMR (250 MHz DMSO-d$^6$ and CDCl$_3$): δ 0.82 (d, J=6.6 Hz, 6H), 1.10 (s, 9H), 1.11 (s, 9H), 1.19 (s, 9H), 1.22 (s, 9H), 2.13 (m, 1H), 2.57 (d, J 7.1, 21), 6.88 (s, 1H), 7.04-7.06 (dd, 2H), 7.21 (d, 2H), 7.23 (d, 2H), 7.47 (s, 1H), 8.47 (s, 1H), 8.58 (s, 1H), 12.08 (bs, 1H), 13.15 (bs, 1H), 13.25 (bs, 1H). $^{13}$C-NMR (62.5 MHz, DMSO-d$^6$ and CDCl$_3$): δ 166.6, 164.1, 161.4, 158.4, 158.1, 155.6, 144.4, 140.4, 138.7, 136.9, 136.8, 131.3, 128.5, 128.0, 127.0, 126.8, 118.2, 118.0, 117.8, 105.4, 42.0, 34.9, 34.0, 31.3, 29.3, 26.5, 22.6. Formula: $C_{42}H_{56}N_4O_3$. MS (M+14): 665.0, HRMS: found (665.4431), calc (665.4430). TR: 3423.7 cm$^{-1}$(bs), 2956.9 cm$^{-1}$, 2920.1 cm$^{-1}$, 2880.1 cm$^{-1}$, 1656.9 cm$^{-1}$, 1616.4 cm$^{-1}$, 1583.6 cm$^{-1}$1469.8 cm$^{-1}$, 1437.0 cm$^{-1}$, 1386.8 cm$^{-1}$, 1367.5 cm$^{-1}$, 1255.7 cm$^{-1}$, 1207.4 cm$^{-1}$. UV: 301.3 nm (bs), 389.6 nm (bs).

6ce $^1$H-NMR (250 MHz DMSO-d$^6$): δ 0.98 (d, J=6.5 Hz, 6H), 2.27 (m, 1H), 2.70 (d, J=6.9, 2H), 6.94-7.11 (m, 4H), 7.38 (s, 1H), 7.41-7.46 (m, 2H), 7.68 (d, 1H), 7.79 (d, 1H), 7.96 (s, 1H), 8.89 (s, 1H), 9.14 (s, 1H), 12.34 (bs, 2H), 13.14 (bs, 1H). $^{13}$C-NMR (62.5 MHz, DMSO-d$^6$): δ 164.6, 163.9, 161.7, 160.9, 160.6, 155.2, 145.6, 138.0, 134.4, 133.8, 131.1, 132.4, 132.0, 131.2, 120.2, 120.0, 119.8, 119.5, 118.0, 117.2, 105.8, 42.1, 26.6, 23.1. Formula: $C_{26}H_{24}N_4O_3$. MS (M+H): 441.0. HRMS: found (441.1922), calc (441.1926). IR: 3441.0 cm$^{-1}$(bs), 3425.6 cm$^{-1}$(bs), 2955.0 cm$^{-1}$, 2922/cm$^{-1}$, 2864.3 cm$^{-1}$, 1658.8 cm$^{-1}$, 1616.4 cm$^{-1}$, 1572.0 cm$^{-1}$, 1485.2 cm$^{-1}$, 1384.9 cm$^{-1}$, 1278.8 cm$^{-1}$, 1203.6 cm$^{-1}$. UV: 383.6 nm (bs).

6da $^1$H-NMR (400 MHz DMSO-d$^6$): δ 2.14 (s, 3H), 2.95 (t, 2H), 3.13 (t, 2H), 6.81 (t, 1H), 6.84 (t, 1H), 6.95 (d, 1H), 7.00 (d, 1H), 7.11 (s, 1H), 7.15 (d, 1H), 7.23 (d, 1H), 7.92 (s, 1H), 8.88 (s, 1H), 9.08 (s, 1H), 9.25 (bs, 1H, D$_2$O exchangeable), 9.43 (bs, 1H, D$_2$O exchangeable), 12.23 (bs, 1H, D$_2$O exchangeable), 12.53 (bs, 1H, D$_2$O exchangeable), 13.02 (bs, 1H, D$_2$O exchangeable). $^{13}$C-NMR (100 MHz, DMSO-d$^6$): δ 165.7, 164.8, 160.6, 155.0, 149.9, 149.7, 146.2, 146.1, 145.6, 138.2, 132.0, 131.1, 123.4, 122.9, 120.3, 120.2, 120.0, 119.6, 119.2, 118.3, 106.1, 33.2, 30.5, 15.0. Formula: $C_{25}H_{22}N_4O_5S$, MS (M+H): 491.0, HRMS: found (491.1389), calc (491.1389). IR: 3415.9 cm$^{-1}$(bs), 2920.2 cm$^{-1}$, 2852.7 cm$^{-1}$, 1656.9 cm$^{-1}$, 1616.4 cm$^{-1}$, 1467.8 cm$^{-1}$, 1373.3 cm$^{-1}$, 1271.1 cm$^{-1}$, 1230.6 cm$^1$. UV: 307.4 nm (bs), 390.5 nm (bs).

6 db $^1$H-NMR (400 MHz DMSO-d$^6$): δ 2.14 (s, 3H), 2.94 (t, 2H), 3.12 (t, 2H), 6.77-6.93 (m, 4H), 7.06 (s, 2H), 7.14 (s, 1H), 7.92 (s, 1H), 8.78 (s, 1H), 8.80 (s, 1H), 9.12 (bs, 1H), 9.16 (bs, 1H), 11.48 (bs, 1H), 12.34 (bs, 1H), 12.49 (bs, 1H). $^{13}$C-NMR (100 MHz, DMSO-d$^6$): δ 164.4, 163.8, 153.8, 153.5, 150.2, 150.0, 132.0, 121.7, 120.2, 119.9, 118.1, 117.9, 117.7, 116.5, 105.9; 33.1, 30.1, 15.2. Formula: $C_{25}H_{22}N_4O_5S$, MS (M+H): 491.0. HRMS: found (491.1384), calc (491.1389). IR: 3439.1 cm$^{-1}$(bs), 2972.3 cm$^{-1}$, 2924.1 cm$^{-1}$, 1654.9 cm$^{-1}$, 1624.1 cm$^{-1}$, 1575.8 cm$^{-1}$, 1477.5 cm$^{-1}$, 1388.8 cm$^{-1}$, 1282.7 cm$^{-1}$, 1220.9 UV: 302.2 nm (wbs), 391.4 nm (bs).

6dc $^1$H-NMR (250 MHz DMSO-d$^6$): δ 1.36 (s, 9H), 1.40 (s, 9H), 2.14 (s, 3H), 2.94 (t, 2H), 3.11 (t, 2H), 6.93-6.98 (m, 2H), 7.20 (s, 1H), 7.39 (d, 1H), 7.41 (d, 1H), 7.54 (t, 2H), 8.00 (s, 1H), 8.93 (s, 1H), 9.14 (s, 1H), 12.56 (bs, 1H), 13.72 (bs, 1H), 14.01 (bs, 1H). $^{13}$C-NMR (62.5 MHz, DMSO-d$^6$): δ 166.9, 165.2, 160.6, 160.4, 154.9, 144.6, 138.1, 137.2, 137.0, 132.1, 131.8, 131.3, 130.6, 119.6, 119.3, 118.9, 118.7, 118.2, 105.9, 349, 33.2, 30.5, 29.6, 15.3, Formula: $C_{33}H_{38}N_4O_3S$, MS (M+H): 571.0. HRMS: found (571.2738), calc (571.2743). IR: 3433.3 cm$^{-1}$(bs), 3417.9 cm$^{-1}$(bs), 2953.0 cm$^{-1}$, 2920.2 cm$^{-1}$, 2872.0 cm$^{-1}$, 1666.5 cm$^{-1}$, 1654.9 cm$^{-1}$, 1606.7 cm$^{-1}$, 1489.1 cm$^{-1}$, 1427.3 cm$^{-1}$, 1388.8 cm$^{-1}$, 1311.6 cm$^{-1}$, 1267.2 cm$^{-1}$. UV: 305.6 nm (bs), 389.6 nm (bs).

6dd $^1$H-NMR (400 MHz DMSO-d$^6$ and CDCl$_3$): δ1.20 (s, 9H), 1.21 (s, 9H), 1.29 (s, 9H), 1.32 (s, 9H), 2.15 (s, 3H), 2.90 (t, 2H), 3.12 (t, 2H), 6.97 (s, 1H), 7.14 (s, 2H), 7.31 (d, 1H), 7.34 (d, 1H), 7.56 (s, 1H), 8.55 (s, 1H), 8.65 (s, 1H), 12.20 (bs, 1H), 13.21 (bs, 1H), 13.32 (bs, 1H). $^{13}$C-NMR (100 MHz, DMSO-d$^6$ and CDCl$_3$): δ 165.8, 164.3, 159.8, 158.6, 158.3, 155.4, 144.9, 140.5, 140.4, 139.0, 137.1, 137.0, 131.4, 131.3, 128.7, 1281, 127.1, 126.9, 118.3, 118.1, 118.0, 105.6, 35.0, 34.1., 33.1, 31.4, 30.6, 29.3, 15.5. Formula: $C_{41}H_{54}N_4O_3S$ MS (M+H): 683.0. HRMS: found (683.4005), calc (683.3995). IR: 3441.0 cm$^{-1}$ (bs), 3425.6 cm$^{-1}$(bs), 2956.9 cm$^{-1}$, 2914.4 cm$^{-1}$, 2870.1 cm$^{-1}$, 1656.9 cm$^{-1}$, 1616.4 cm$^{-1}$, 1583.6 cm$^{-1}$, 1469.8 cm$^{-1}$, 1433.1 cm$^{-1}$, 1386.8 cm$^{-1}$, 1269.2 cm$^{-1}$, 1259.5 cm$^{-1}$. UV: 302.2 nm (bs), 391.4 nm (bs).

6de $^1$H-NMR (400 MHz DMSO-d$^6$): δ2.14 (s, 3H), 2.95 (t, 2H), 3.13 (t, 2H), 6.95-7.04 (m, 4H), 7.12 (s, 1H), 7.42 (t, 1H), 7.47 (t, 1H), 7.70 (d, 1H), 7.79 (d, 1H), 7.96 (s, 1H), 8.91 (s, 1H), 9.14 (s, 1H), 12.30 (bs, 1H), 12.54 (bs, 1H), 13.12 (bs, 1H). $^{13}$C-NMR (100 MHz, DMSO-d$^6$): δ164.7, 164.0, 160.9, 160.6, 155.0, 145.8, 138.1, 134.5, 133.8, 133.1, 120.2, 120.0, 119.9, 118.1, 117.2, 117.1, 105.8, 33.2, 30.5, 15.2. Formula: $C_{25}H_{22}N_4O_3S$. MS (M+H): 459.0. HRMS: found (459.1489), calc (459.1491). IR: 3441.0 cm$^{-1}$(bs), 3423.6 cm$^{-1}$ (bs), 2916.4 cm$^{-1}$, 2841.2 cm$^{-1}$, 2796.8 cm$^{-1}$, 1660.7 cm$^{-1}$, 1614.4 cm$^{-1}$, 1570.1 cm$^{-1}$, 1479.4 cm$^{-1}$, 1398.4 cm$^{-1}$, 1276.9 cm$^{-1}$, 1201.6 cm$^{-1}$. UV: 335.9 nm (bs), 387.0 nm (bs).

Example 1

References

1. Marzano, C.; Pellei, M.; Colavito, D.; Alidori, S.; Lobbia, G. G.; Gandin, V.; Tisato, F.; Santini, C., *J. Med. Chem.* 2006, 49, 7317-7324.
2. Bregman, H.; Williams, D. S.; Atilia, G. E.; Carroll, P. J.; Meggers, E., *J. Am. Chem. Soc.* 2004, 126, (24), 13594-13595.
3. Doctrow, S. R.; Huffman, K.; Marcus, C. B.; Tocco, G.; Malfroy, E.; Adinolti, C. A.; Kruk, H.; Baker, K.; Lazarowych, N.; Mascarenhas, J.; Malfroy, B., *J. Med. Chem.* 2002, 45, 4549-4558.
4. Murahashi, S.; Naota, T.; Taki, H., *J. Chem. Soc., Chem. Commun.* 1985, 613-614.
5. Irie, R.; Noda, K.; Ito, Y.; Matsumoto, N.; Katsuki, T., *Tetrahedron Lett.* 1990, 31, 7345-7348.
6. Zhang, W.; Loebach, J. L.; Wilson, S. R.; Jacobsen, E. N., *J. Am. Chem. Soc.* 1990, 112, 2801-2083.
7. Jacobsen, E. N.; Kakiuchi, F.; Konsler, R. G.; Larrow, J. F.; Tokunaga, M., *Tetrahedron Lett.* 1997, 38, 773-776.

8. Wu, M. H.; Jacobsen, E. N., *J. Org. Chem.* 1998, 63, 5252-5254.
9. Wu, M. H.; Hansen, K. B.; Jacobsen, E. N., *Angew. Chem. Int. Ed.* 1999, 38, 2012-2014.
10. Holbach, M.; Weck, M., *J. Org. Chem.* 2006, 71, 1825-1836.
11. Peukert, F.; Jacobsen, E. N., *Org. Lett.* 1999, 1(8), 1245-1248.
12. Yoon, T. P.; Jacobsen, E. N., *Science* 2003, 299.1691-1693.
13. Canali, L.; Sherrington., D. C., *Chem. Soc. Rev.* 1999, 28, 85-93.
14. Zhang, H.; Li, C., *Tetrahedron* 2006, 62, 6640-6649.
15. Banti, D.; Belokon, Y. N.; Fu, W. L.; Groaz, E.; North, M., *Chem. Comm.* 2005, 2707-2709.
16. Sasaki, H.; Irie, R.; Hamada, T.; Suzuki, K.; Katsuki, T., *Tetrahedron* 1994, 50 11827-11838.
17. Fukuda, T.; Katsuki, T., *Tetrahedron Lett* 1996, 37, 4389-4392.
18. Hamachi, K.; Irie, R.; Katsuki, T., *Tetrahedron Lett* 1996, 37, 4979-4982.
19. Katsuki, T., *Journal Mot. Catal. A: Chemical* 1996, 113, 87-107.
20. Nishikori, H.; Katsuki, T., *Applied Catalysis A: General* 2000, 194-195, 475-477.
21. Niimi, T.; Uchida, T.; Me, R.; Katsuki, T., *Tetrahedron Lett.* 2000, 41, 3647-3615.
22. Ready, J. M.; Jacobsen, E. N., *J. Am. Chem. Soc.* 2001, 123, 2687-2688.
23. Sun, W.; Kuhn, F. E., *Applied Catalysis A: General* 2005, 285, 163-168.
24. Schaper, W. W.; Lothar, R. C.; Erwin, H.; Eckhard, R.; Dirk, S.; U.S. Pat. Appl. Publ. 2005, US2005256000 A1 20051117 CAN 143:454394 AN 2005:1224419, 97.
25. Jaung, J. Y., *Dyes and Pigments* 2006, 71, (3), 245-250.
26. Zhang, L.; Liu, G.; Zhang, S. D.; Yang, H. Z.; Li, L.; Wu, X. H.; Yu, J. L.; Kou, B. B.; Xu, S.; Li, J.; Sun, G. C.; Ji, Y. F.; Cheng, G. F.; *J. Comb. Chem.* 2004, 6, 431-436.
27. Li, L.; Liu, G.; Wang, Z. G.; Yuan, Y. Y.; Zhang, C. X.; Tian, H. Y.; Wu, X. H.; Zhang, J., *J. Comb. Chem.* 2004, 6, (5), 811-821.
28. Wu, X. H; Liu, G.; Zhang, J.; Wang, Z. G.; Xu, S.; Zhang, S. D.; Zhang, L.; Wang, L., *Mol. Diversity.* 2004, 8, 165-174.
29. Aguiari, A.; Bullita, E.; Casellao, U.; Guerriero, P.; Tamburini, S.; Vigato, P. A., *Inorg. Chinn. Acta* 1992, 202, 157-171.
30. Holbach, M.; Zheng, X. L.; Surd, C.; Jones, C. W.; Weck, M., *J. Org. Chem.* 2006, 71, 2903-2906.
31. Gallant, A. J.; Patrick, B. O., *J. Org. Chem.* 2004, 69, 8739-8744,
32. Gordon, J. C.; Shukla, P.; Cowley, A. H.; Jones, J. H.; Keogh, D. W.; Scott, B. L., *Chem. Comm.* 2002, 2710-2711
33. Liu, G.; Fan, Y. M., Calson, J. R.; and Lam, K. S., *J. Comb. Chem.* 2000.2, (5), 467-474.

Example 2

Reference is made to Wu et al., "Regioselective Synthesis of Asymmetrically Substituted 2-Quinoxalinol Salen Ligands,"*J. Org. Chem., November* 9; 72(23):8691-9. Epub 2007 Oct. 16., the content of which is incorporated herein by reference in its entirety.

Abstract and Introduction

Diamino-2-quinoxalinols were reacted with salicylaldehyde derivatives to produce 2-quinoxalinol imines regioselectively as one isomer in good yield. Regioselectivity was characterized through the use of isotopic $^{15}$N labeling experiments. The 2-quinoxalinol imines thereby obtained may further be reacted without purification with additional salicylaldehyde derivatives to yield asymmetrically substituted 2-quinoxalinol salens.

The synthesis of 2-quinoxalinol imines is challenging, because they are often unstable, particularly when using bulky imines. The synthesis of the key intermediate, the 2-quinoxalinol imine (3a) from diamino-2-quinoxalinol (1) is a unique challenge, because of the difficulty in obtaining one isomer as the final product. If the reaction can be controlled such that only one amine is reacted with an aldehyde, this would provide a method to develop asymmetrically substituted 2-quinoxalinol salens. Here, a side product determined to be the half unit salen ligand, that is, a single product, a 2-quinoxalinol imine (3) was successfully synthesized and isolated. The use of this side product as a starting material for asymmetrically substituted ligands provides a means to overcome the difficulty of synthesis in producing regioselective or bulky 2-quinoxalinol imine compounds. In addition, these 2-quinoxalinol imines are stable in atmospheric conditions.

Scheme 3 illustrates that identifying the exact structure of the 2-quinoxalinol imines is difficult because two isomers [(3a) or (3b)] are possible.

Scheme 3 Route to 2-Quinoxalinol Imines 3a and asymmetrically substituted salen 4.

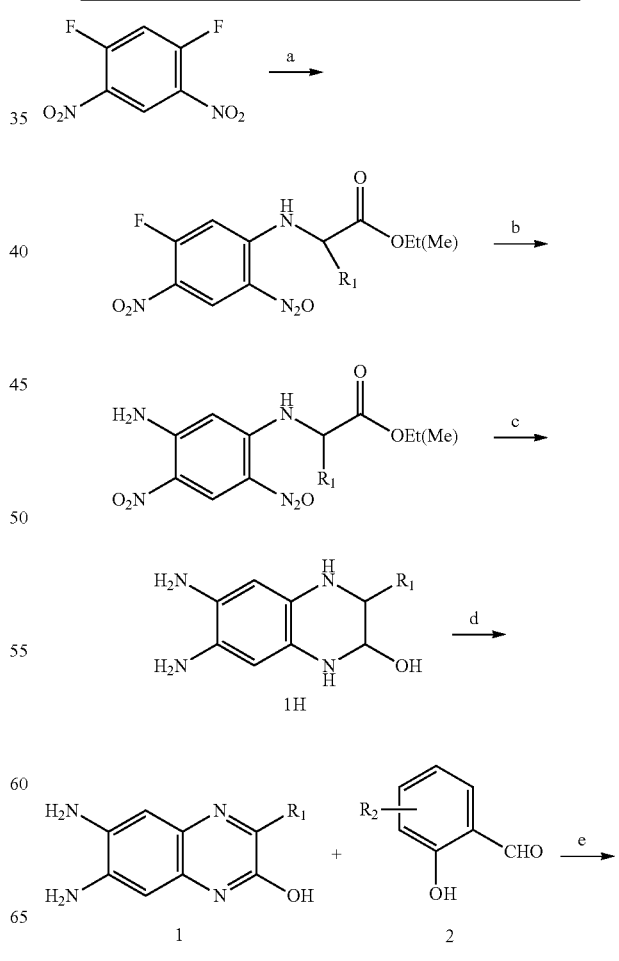

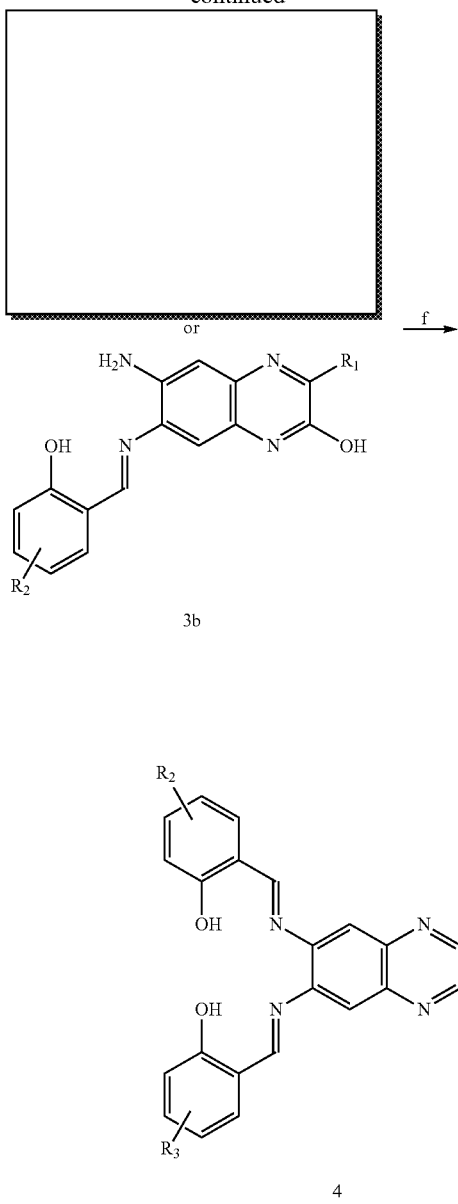

a. THF, Amino acid, 1 equiv, DIEPA, b. NH$_3$•H$_2$O, THF, c. Pd—C, HCOONH$_4$, 95% EtOH, N$_2$, d. air or O$_2$, e. MeOH 80° C. f. MeOH, salicylaldehyde 2′, 80° C.

Here, the exact structure of these 2-quinoxalinol imine was determined using isotope $^{15}$N labeled compounds and NMR technology. The reaction was found to be regioselective. Based on these observations, several 2-quinoxalinol imine intermediates were synthesized and used as synthetic building blocks in the preparation of asymmetrically substituted salen-based ligands.

Results and Discussion

The general synthetic route for the formation of the 2-quinoxalinol salen ligands has been reported previously, and it was previously shown that the ratio of the starting materials used (diamino-2-quinoxalinol (1) to salicylaldehyde derivatives (2)) is important for optimization of the reaction. When the ratio is 1:1.2, a 2-quinoxalinol imine is the major product with high regioselectivity. If the ratio of reactants is increased, the yield of symmetric 2-quinoxalinol salens increases. As the ratio of reactants reaches 1:10, the yield of the symmetric 2-quinoxolinol salen is much higher.

The identification of 2-quinoxalinol imine intermediates in the reaction is important to determine the utility of these compounds in asymmetric syntheses, because two configurations [(3a) or (3b)] are possible. In order to identify the exact structure, the two amino groups of the diamino-2-quinoxalinol intermediate (1) were differentiated by replacing ammonium hydroxide with $^{15}$N labeled ammonium hydroxide during the secondary substitution of the 1,5-difluoro-2,4-dinitrobenzene (DFDNB). Because of the heteronuclear coupling of $^{15}$N, $^1$H-NMR can be used to demonstrate a difference between the two amino groups of intermediate (1). Thus, in the 2-quinoxalinol imine intermediate, the position of the imine formation (whether on the $^{15}$N or $^{14}$N of intermediate (1)) can be identified. The $^1$H-NMR spectra with intermediate (1a), 2-quinoxalinol imine (3ae) and the $^{15}$N labeled intermediate (1a), 2-quinoxalinol imine (3ae) are shown in FIG. 2.

Figure 2:
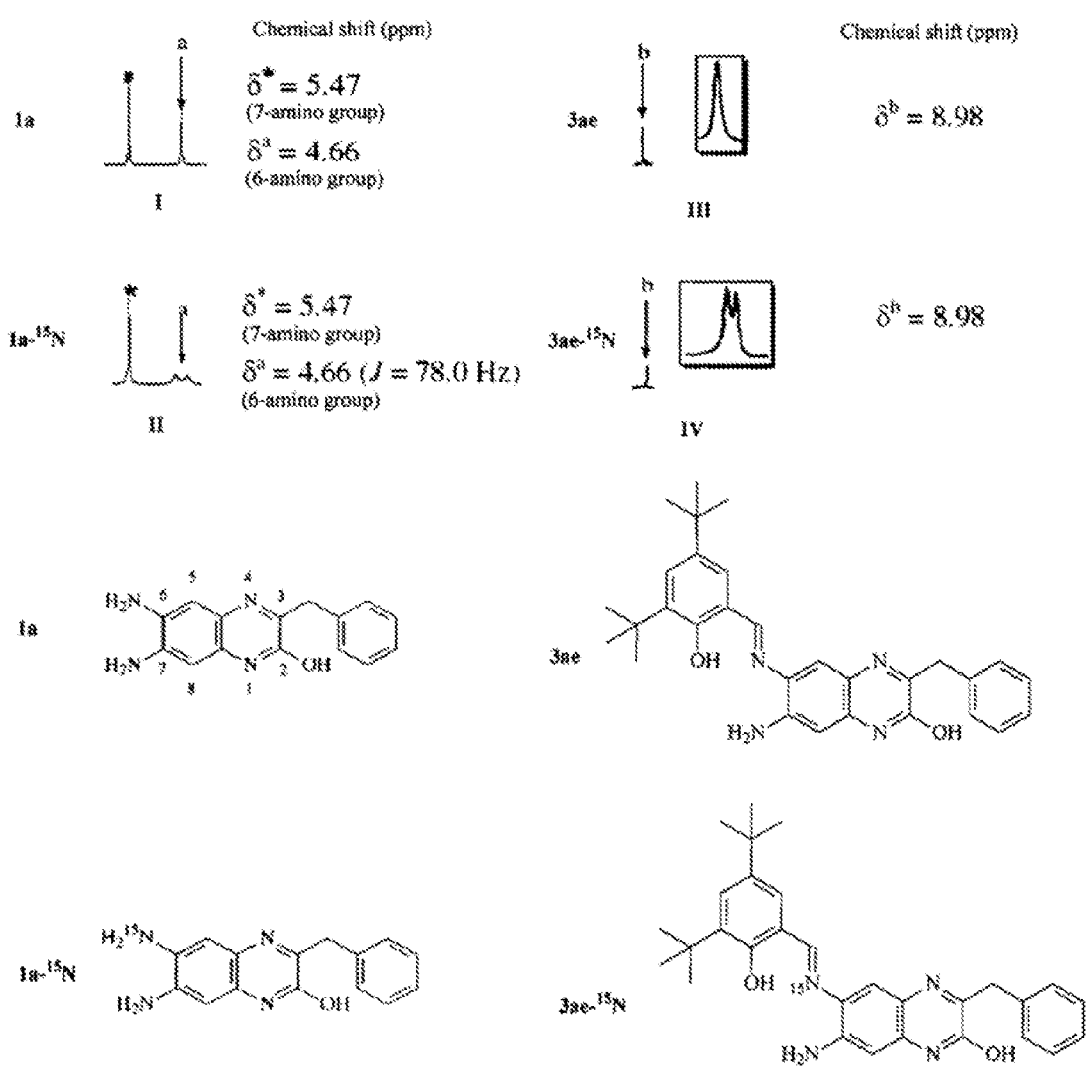
FIG. 2. provides H-NMR results from Example 2 of intermediate (1a) and 2-quinoxalinol imines (3ae). For intermediate (1a), $^1$H-NMR of hydrogen of two amino groups is shown. For 2-quinoxalinol imine (3ae), only the hydrogen on the carbon of imine group is shown.

In FIG. 2, for intermediate (1a), the "a" labeled peaks corresponding to the two protons of the $^{14}$N and $^{15}$N amino groups are different in spectra I and II. Spectra I has a broad single peak, while in spectra II, with heteronuclear coupling, the protons are split (J=78.0 Hz). For the $^{13}$N labeling 2-quinoxalinol imines (3ae-$^{15}$N), the peak marked "b" corresponding to the proton on the carbon of imine group are split by $^{15}$N (J=3.0) (spectra IV), whereas it is still a single peak in spectra III. At the same time, in the spectra III and IV, the peak (δ=4.66 ppm) disappear. Therefore, the final structure of 2-quinoxalinol imines is 3ae.

The higher reactivity of the 6-amino group versus the 7-amino group may be explained based on either a kinetic or a thermodynamic argument. In the kinetic explanation, the 2-quinoxalinol ring is an aromatic system, and the 2-hydroxyl group is an electron-donor group which increases electron density of the carbon contacting 6-amino group and so making 6-amino group more reactive than the 7-amino group (an α-nucleophile effect). This effect is evident in the $^1$H-NMR of intermediate 1 (FIG. 2). There is a substantial difference between the chemical shift of hydrogen on 6 and 7 amino groups (Δδ=0.81 ppm, as identified in the labeling study). The two amino groups are in the same benzene ring, the up-field hydrogen of the 6-amino group must have more electron density and, therefore, the 6-amino group is more reactive than the 7-amino group downfield.

This can be confirmed by computational results. The density functional theory method B3LYP/6-31G(d) was used to characterize intermediate (1) and 2-quinoxalinol imines (3a) and ground states in vacuum using Gaussian 03. Calculations using B3LYP/6-31G(d) were used for geometry optimizations and the calculation of vibrational frequencies, which confirmed all stationary points as minima and provided thermodynamic corrections. The effect of methanol was approximated by subsequent single-point calculations using the conductor-like polarizable continuum model (CPCM). The default Gaussian 03 dielectric constant of 32.63 was used for methanol. Partial charges for the intermediate (1) and 2-quinoxalinol imines (3a) were obtained using CHELPG method. The calculation results show that the 6-nitrogen in each case has more negative charge than the 7-nitrogen, and the 6-amino group of 2-qunioxilinol should be more reactive that 7-amino group. (See Table 3.)

TABLE 3

Calculation results of intermediate 1.

| Intermediate | $R_1$ | Charge of 6-nitrogen ($\delta_6$) | Charge of 7-nitrogen ($\delta_7$) | $\geq \delta_{6-7}$ |
|---|---|---|---|---|
| 1a | benzyl | −0.857 | −0.831 | 0.026 |
| 1b | isopropyl | −0.856 | −0.831 | 0.025 |
| 1c | sec-butyl | −0.861 | −0.839 | 0.022 |
| 1d | −CH$_2$CH$_2$SCH$_3$ | −0.848 | −0.817 | 0.039 |
| 1e | H | −0.852 | −0.823 | 0.029 |

Finally, based on thermodynamics the minimized energy of three pair of 2-quinoxalinol imines isomers (3ad and 3bd, 3af and 3bf and 3ai and 3bi) was calculated with the same method (vida supra) using a model of gas and methanol. The minimized energy of 3ad, 3af and 3ai are 0.869, 0.931 and 0.954 lower in the gas model; and 0.800, 0.889 and 1.061 kcal/mol lower in the MeOH model than their respective isomers (3bd, 3bf and 3bi). Therefore, from the thermodynamic view, 3ad, 3af and 3ai are more stable than their isomers.

The synthetic method for the preparation of 2-quinoxalinol imines (3a) began with the addition of 1.0 equiv. of the intermediate (1) dissolved in 4 mL methanol to a solution of 1.2 equiv substituted salicylaldehyde (2) in 6 mL methanol. The two were combined with stirring, and after heating at refluxing temperature for 1 hour, the reaction mixture becomes deep yellow or red. Stirring at refluxing temperature was continued for 14 hours, and monitored by TLC. Once it was observed that the reaction mixture no longer contains starting material (1), the reaction was stopped by allowing the mixture to cool to room temperature. Pure 2-quinoxalinol imines (3a) were obtained by flash column chromatography using hexane:ethyl acetate, 3:1 as eluent. According to this method, eight different 2-quinoxalinol imines (3aa-3ah) were prepared (Table 4).

TABLE 4

Formation of 2-Quinoxalinol Imines (3ax).

| Product | $R_1$ | $R_2$ | Yield (%) |
|---|---|---|---|
| 3aa | benzyl | 3-tert-butyl | 93.8* |
| 3ab | isopropyl | 3-tert-butyl | 70.2* |
| 3ac | sec-butyl | 3-tert-butyl | 71.5* |
| 3ad | −CH$_2$CH$_2$SCH$_3$ | 3-tert-butyl | 65.5* |
| 3ae | benzyl | 3,5-Di-tert-butyl | 76.7* |
| 3af | isopropyl | 3,5-Di-tert-butyl | 66.0* |
| 3ag | sec-butyl | 3,5-Di-tert-butyl | 89.2* |
| 3ah | −CH$_2$CH$_2$SCH$_3$ | 3,5-Di-tert-butyl | 80.0* |
| 3ai | benzyl | 3-OH | 68.5* |
| 3aj | H | 3-tert-butyl | —¶ |
| 3ak | H | 3,5-Di-tert-butyl | —¶ |

*One-step yield purified by column separation.

The yield of final products ranges from 65% to 94%. When $R_1$ was a hydrogen atom, the diamino-2-quinoxalinol (1e) was not stable and was found to decompose on exposure to air. Because of this, it was directly used for the following reaction with 12 equiv salicylaldehyde under nitrogen gas protection without purification after the reduction reaction. The undehydrogenating diamino-2-quinoxalinol 1H reacts with the salicylaldehyde derivative. The major byproducts were 3aj-1 (11.0%) and 3ak-1 (10.0%) and the expected products 3aj and 3ak was not obtained. For sample 3ai, a modified procedure was used. After heating to reflux temperature for 4 hours, a red precipitate (3ai) forms. The red solid was filtered off and washed with 95% ethanol followed by acetone resulting in the pure final 2-quinoxalinol imine (3ai). Unlike the previous reactions, prolonging the reaction time did not increase the yield of product (3ai). Other salicylaldehyde derivatives with different functional groups in the 3 position were tried, but the expected final 2-quinoxalinol imines (e.g., 3a) were not obtained. In contrast, in some cases, low yields of the symmetric 2-quirioxalinol salens were obtained. When the 3 position had bulky group such as tert-butyl group, the 2-quinoxalinol imines (3a) were formed as the major products. The compound 3ai is a special case, but when another intermediate (1) with different group $R_1$ reacted with 2,3-dihydroxy salicylaldehyde, the expected products were not formed. These results demonstrate that the 2-quinoxalinol aromatic system and 3 position bulky group of salicylaldehyde are necessary to the regioselective effect. All of the final products were identified and characterized by H-NMR, $^{13}$C-NMR, MS, HR-MS, and IR. In all cases, the $R_1$ groups are electron-donor groups or are neutral (H). In the case of reactions with an electron-withdrawing group on $R_1$, such as with a trifluoromethyl group, the resultant diamino-2-quinoxalinol was unstable, and its 2-quinoxalinol imine was not obtained.

Based on these experiments, nine 2-quinoxalinol imines (3aa-3ai), and twelve asymmetrically substituted 2-quinoxalinol salens (4a-4l) were obtained (Table 5).

TABLE 5

Formation of Asymmetrically Substituted 2-Quinoxalinol Salen Ligands (4).

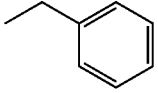

| Product | $R_1$ | $R_2$ | $R_3$ | Yield (%)* |
|---|---|---|---|---|
| 4a | 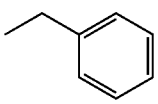 | 3-tert-butyl | 3,5-Di-tert-butyl | 49.1 |
| 4b | 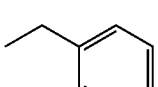 | 3-tert-butyl | H | 60.5 |
| 4c | 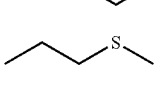 | 3,5-Di-tert-butyl | 3-tert-butyl | 41.0 |
| 4d | 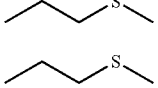 | 3-tert-butyl | 3,5-Di-tert-butyl | 54.2 |
| 4e |  | 3-tert-butyl | H | 63.0 |
| 4f | 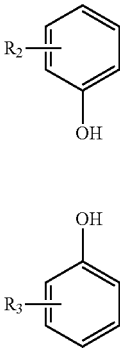 | 3,5-Di-tert-butyl | 3-tert-butyl | 44.7 |

TABLE 5-continued

Formation of Asymmetrically Substituted 2-Quinoxalinol Salen Ligands (4).

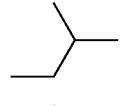

| Product | $R_1$ | $R_2$ | $R_3$ | Yield (%)* |
|---|---|---|---|---|
| 4g | 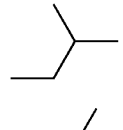 | 3-tert-butyl | 3,5-Di-tert-butyl | 50.0 |
| 4h | 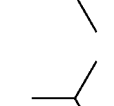 | 3-tert-butyl | H | 68.5 |
| 4i | 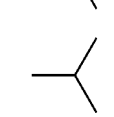 | 3,5-Di-tert-butyl | 3-tert-butyl | 38.5 |
| 4j |  | 3-tert-butyl | 3,5-Di-tert-butyl | 50.5 |
| 4k | | 3-tert-butyl | H | 66.4 |
| 4l | | 3,5-Di-tert-butyl | 3-tert-butyl | 43.7 |

*Yield is a two step yield (i.e., the yield from starting material 1 to final product 4).

The procedure for the synthesis of these asymmetrically substituted 2-quinoxalinol salens is unique and can be done in, one pot. According to the general procedure of synthesis of 2-quinoxalinol imines 3a, when the imines are formed, without additional purification, a second substituted salicylaldehyde 2' was directly added into the methanol reaction solution. The reaction mixture was allowed to heat to reflux temperature for another 14 hours, and in the end, a precipitate forms. The end product can be filtered and washed with 95% ethanol and acetone 5 times each. The precipitates were directly identified by NMR and MS. The purities of them are very high. All of synthesized salens (4a-4l) are of low solubility in water, hexane, methanol, or ethanol. When $R_3$ is H, these ligands are very soluble in DMSO or DMF, but not in DCM or CHCl$_3$, whereas other salens are, in contrast, soluble in DCM or CHCl$_3$, but of low solubility in DMSO.

Combinations of different $R_1$, $R_2$ and $R_3$ groups were tested. Altering the $R_1$ group does not appear to affect the reactivity of 6,7-amino group. When intermediate 3a was reacted with the first salicylaldehyde 2 containing the $R_2$ group being 3-tert-butyl, $R_3$ of the second salicylaldehyde 2' added could be H or 3,5-di-tert-butyl and the yield of these asymmetrically substituted 2-quinoxalinol salens (4a, 4b, 4d, 4e, 4g, 4h, 4j and 4k) were 50.0%-70.0%, whereas when $R_3$ was a hydroxyl group, there is no expected product; however, when $R_2$ is 3,5-di-tert-butyl, there is only one combination which has a good yield of the asymmetrically substituted 2-quinoxalinol salens, that is, $R_1$ is 3-tert-butyl, the yield is a bit lower (~45%).

Conclusion

The exact structure of 2-quinoxalinol imines was identified using isotope $^{15}N$ labeled compounds. Based on this, a series of new compounds, the 2-quinoxalinol imines were prepared and used to generate a series of asymmetrically substituted 2-quinoxalinol salens. Using the imine functional group in these compounds, further asymmetrically salen ligand may be generated using 2-quinoxalinol derivative prepared from natural or artificial amino acids and labeled peptides, as well as secondary amine products for screening for bioactivity. These asymmetrical 2-quinoxalinol salen ligands further may be used to prepare metal complexes in order to identify their chiral character and develop complexes as potential new chiral catalysts.

Experimental Section

All amino acid methyl esters, DFDNB (1,5-difluoro-2,4-dinitrobenzene), HCl (37%), Ammonium hydroxide (5.0 N), palladium on carbon. (wet, 5%) were purchased and used as received, 15N labeled ammonium hydroxide was purchased from Cambridge Isotope laboratories, Inc. All melting points were recorded, and the values were uncorrected. 1H and 13C NMR spectra were recorded on a 250 MHz NMR spectrometer (operated at 250 and 62.5 MHz, respectively) or 400 MHz spectrometer (operated at 400 and 100 MHz, respectively). Which instrument was used and when is indicated in the data provided. Chemical shifts are reported as 5 values (ppm). NMR data were collected by using DMSO-d6. D2O/water exchange experiments were run in some experiments. The solvents used are indicted in the experimental details. Reaction progress was monitored by thin-layer chromatography (TLC) using 0.25 mm silica gel precoated plates with visualization by irradiation with a UV lamp. HRMS data was collected using Electrospray ionization mass spectrometry or direct probe ionization. IR spectroscopic data was collected using KBr solid samples. Samples for melting point, IR and NMR were purified by flash column chromatography. Calculations were run using Gaussian 03.

General Procedure

3aa-3ai The synthesis of 2-quinoxalinol imine (3a) began with the addition of 1.0 equiv of the intermediate 2-quinoxalinol (1) dissolved in 4 mL methanol to a solution of 1.2 equiv. substituted salicylaldehyde derivatives (2) in 6 mL methanol. The two were combined with stirring for 14 hours, monitored by TLC. Once starting material (1) can no longer be seen by TLC, the reaction was considered complete. Pure 2-quinoxalinol imines (3a) were obtained by purification using flash column chromatography with a solution of hexane:ethyl acetate, 3:1 as eluent. For sample (380, a modified procedure was used. The product began to form as a red solid (3M) after heating at refluxing temperature for 4 hours. The red solid was filtered off and washed with 95% ethanol followed by acetone to obtain pure final 2-quinoxalinol imines (3ai).

4a-4i This procedure is the same as that for preparing the 2-quinoxalinol imine (1); however, when the starting material (1) can no longer be observed using TLC, a second salicylaldehyde derivative 2' can be added directly to the reaction mixture. The mixture was then allowed to heat at refluxing temperature for an additional 14 hours resulting in a large quantity of precipitates. These precipitates were isolated by filtering, and then washed with 95% ethanol and acetone 5 times each. The pure products were identified and characterized by NMR, IR, MS and HRMS.

Experimental Data

3aa $^1$H-NMR (400 MHz DMSO-d$^6$): δ 1.44 (s, 9H), 4.04 (s, 2H), 5.84 (bs, 2H), 6.59 (s, 1H), 6.80 (s, 1H), 6.59-7.74 (m, 9H), 8.98 (s, 1H), 12.15 (bs, 1H), 13.58 (bs, 1H). $^{13}$C-NMR (100 MHz, DMSO-d$^6$): δ 167.4, 164.0, 159.8, 155.5, 154.2, 145.6, 138.8, 136.8, 133.4, 132.3, 132.2, 132.0, 131.8, 130.4, 129.5, 129.2, 128.7, 126.6, 125.0, 120.0, 119.0, 117.1, 97.7, 40.0, 35.0, 30.0. Formula: $C_{26}H_{26}N_4O_2$. MS (M+H): 426.0. HRMS: found (426.2051), calc 026.2056). IR: 3470.0 cm$^{-1}$ (bs), 3375.4 cm$^{-1}$(bs), 3182.6 cm$^{-1}$, 2956.9 cm$^{-1}$, 2927.9 cm$^{-1}$, 2870.1 cm$^{-1}$, 1728.2 cm$^{-1}$, 1656.9 cm$^{-1}$, 1624.1 cm$^{-1}$, 1271.1 cm$^{-1}$. Melting point: 196.0-199.0° C.

3ab $^1$H-NMR (400 MHz DMSO-d$^6$): δ 1.20 (d, J=6.8, 6H), 1.44 (s, 3.61 (sept, 1H), 5.77 (bs, 2H), 6.60 (s, 1H), 6.94 (t, 1H), 7.38 (d, 1H), 7.53 (d, 1H), 7.55 (s, 1H), 9.03 (s, 1H), 12.07 (bs, 1H), 13.64 (bs, 1H). $^{13}$C-NMR (100 MHz, DMSO-d$^6$): δ 170.8, 163.8, 159.8, 159.6, 155.1, 145.3, 136.8, 133.1, 132.1, 131.8, 130.4, 124.8, 120.1, 119.0, 117.7, 97.8, 35.0, 29.9, 20.8, 14.6. Formula: $C_{22}H_{26}N_4O_2$. MS (M+H): 378.0. HRMS: found (378.2052), calc (378.2056). IR: 3442.9 cm$^{-1}$ (bs), 3402.4 cm$^{-1}$(bs), 2958.8 cm$^{-1}$, 2872.0 cm$^{-1}$, 1710.9 cm$^{-1}$, 1651.1 cm$^{-1}$, 1626.0 cm$^{-1}$, 1502.6 cm$^{-1}$, 1234.4 cm$^{-1}$. Melting point: 250.0-253.0° C. (Color changed).

3ac $^1$H-NMR (250 MHz DMSO-d$^6$): δ 0.93 (d, 7=6.6, 6H), 1.43 (s, 9H), 2.19 (m, 1H), 2.58 (d, 2H), 5.77 (bs, 2H), 6.59 (s, 1H), 6.93 (t, 1H), 7.37 (d, 1H), 7.52 (d, 1H), 7.55 (s, 1H), 8.99 (s, 1H), 12.06 (bs, 1H), 13.62 (bs, 1H). $^{13}$C-NMR (62.5 MHz, DMSO-d$^6$): δ 163.8, 159.8, 155.8, 155.2, 145.3, 136.8, 133.2, 132.1, 131.7, 130.4, 125.0, 120.3, 119.0, 117.6, 97.8, 41.7, 34.9, 29.7, 26.8, 23.1. Formula: $C_{23}H_{28}N_4O_2$. MS (M+H): 392.0. HRMS: found (392.2206), calc (392.2212). IR: 3392.8 cm$^{-1}$(bs), 2954.9 cm$^{-1}$, 2924.1 cm$^{-1}$, 2866.2 cm$^{-1}$, 1710.0 cm$^{-1}$, 1626.0 cm$^{-1}$, 1600.9 cm$^{-1}$, 1371.4 cm$^{-1}$, 1232.5 cm$^{-1}$. Melting point: >300.0° C.

3ad $^1$H-NMR (250 MHz DMSO-d$^6$): δ1.43 (s, 9H), 2.09 (s, 3H), 2.86 (t, 2H), 2.97 (t, 2H), 5.82 (bs, 2H), 6.59 (s, 1H), 6.93 (t, 1H), 7.37 (d, 1H) 7.51 (d, 1H), 7.53 (s, 1H), 12.11 (bs, 1H), 13.59 (bs, 1H). $^{13}$C-NMR (62.5 MHz, DMSO-d$^6$): δ 163.9, 159.8, 155.5, 153.9, 145.5, 136.8, 133.3, 132.3, 131.8, 130.4, 125.0, 120.0, 119.0, 117.6, 97.8, 34.9, 32.8, 30.9, 29.7, 15.2. Formula: $C_{22}H_{26}N_4O_2S$. MS (M+H): 410.0. HRMS: found (410.1767), calc (410.1776). IR: 3469.9 cm$^{-1}$(bs), 3334.9 cm$^{-1}$(bs), 2920.2 cm$^{-1}$, 2954.9 cm$^{-1}$, 2918.3 cm$^{-1}$, 2875.9 cm$^{-1}$, 1710.8 cm$^{-1}$, 1662.6 cm$^{-1}$, 1626.0 cm$^{-1}$, 1429.3 cm$^{-1}$, 1234.4 cm$^{-1}$. Melting point: 225.0-227.0° C.

3ae $^1$H-NMR (400 MHz DMSO-d$^6$): δ 1.31 (s, 9H), 1.44 (s, 9H), 4.05 (s, 2H), 5.81 (bs, 2H, D$_2$O exchangeable), 6.58 (s, 1H), 7.20-7.55 (m, 8H), 8.99 (s, 1H), 12.15 (bs, 1H, D$_2$O exchangeable), 13.32 (bs, 114, D$_2$O exchangeable). $^{13}$C-NMR (100 MHz, DMSO-d$^6$): δ 168.2, 162.4, 160.5, 159.5, 145.7, 142.7, 141.4, 137.7, 137.5, 134.1, 133.0, 132.8, 131.8, 131.0, 130.6, 123.4, 121.8, 102.9, 40.0, 39.8, 38.9, 36.2, 34.2. Formula: $C_{30}H_{34}N_4O_2$. MS: 482.0. HRMS: found (482.2681), calc (482.2682). IR: 3491.2 cm$^{-1}$(bs), 3375.4 cm$^{-1}$, 2955.08 cm$^{-1}$, 2870.18 cm$^{-1}$, 2821.98 cm$^{-1}$, 1718.68 cm$^{-1}$, 1653.0 cm$^{-1}$, 1626.0 cm$^{-1}$, 1502.6 cm$^{-1}$, 1238.0 cm$^{-1}$. Melting point: 248.0-250.0° C. 3ae $^{15}$N: $^1$H-NMR (400 MHz DMSO-d$^6$): δ 1.31 (s, 9H), 1.44 (s, 9H), 4.04 (s, 2H), 5.81 (bs, 2H, D$_2$O exchangeable), 6.58 (s, 1H), 7.21-7.55 (m, 8H), 8.98 (d, 1H), 12.14 (bs, 1H, 020 exchangeable), 13.32 (bs, 1H, D$_2$O exchangeable).

3af $^1$H-NMR (400 MHz DMSO-d$^6$): δ 1.18 (d, 6H), 1.26 (s, 9H), 1.28 (s, 9H), 4.00 (sept, 1H), 5.67 (bs, 2H), 6.59 (s, 1H), 7.40 (s, 1H), 7.54 (s, 1H), 7.58 (s, 1H), 9.04 (s, 1H), 12.06 (bs, 1H), 13.36 (bs, 1H). $^{13}$C-NMR (100 MHz, DMSO-d$^6$): δ 164.3, 159.6, 157.5, 155.1, 145.2, 140.7, 136.0, 133.0, 132.3, 128.2, 127.4, 124.8, 119.4, 117.6, 97.7, 35.1, 34.4, 31.8, 29.8, 20.8, 14.6. Formula: $C_{26}H_{34}N_4O_2$, MS (M+H): 434. HRMS: found (434.2675), calc (434.2682). IR: 3489.2 cm$^{-1}$(bs), 3387.0 cm$^{-1}$, 2958.88 cm$^{-1}$, 2910.68 cm$^{-1}$, 2870.18 cm$^{-1}$, 2819.98 cm$^{-1}$, 1739.88 cm$^{-1}$, 1651.1 cm$^{-1}$, 1620.2 cm$^{-1}$, 1502.6 cm$^{-1}$, 1240.1 cm$^{-1}$. Melting point: 275.0-276.0° C. (Color changed).

3ag $^1$H-NMR (400 MHz DMSO-d$^6$): δ 0.94 (d, 6H), 1.32 (s, 9H), 144 (s, 9H), 2.20 (m, 1H), 2.59 (d, 2H), 5.76 (bs, 2H), 6.59 (s, 1H), 7.40 (s, 1H), 7.54 (s, 1H), 7.57 (s, 1H), 9.01 (s, 1H), 12.06 (bs, 1H), 13.36 (bs, 1H). $^{13}$C-NMR (100 MHz, DMSO-d$^6$): δ 164.4, 157.5, 155.8, 155.0, 145.3, 140.7, 136.0, 133.0, 132.4, 128.2, 127.5, 125.0, 119.4, 117.6, 97.7, 41.7, 35.1, 34.4, 31.8, 29.8, 26.7, 23.1. Formula: $C_{27}H_{36}N_4O_2$, MS (M+H): 448.0. HRMS: found (448.2839), calc (448.2838). IR: 3489.2 cm$^{-1}$ (bs), 3400.5 cm$^{-1}$(bs), 2955.0 cm$^{-1}$, 2866.2 cm$^{-1}$, 2818.0 cm$^{-1}$, 1653.0 cm$^{-1}$, 1626.0 cm$^{-1}$, 1500.6 cm$^{-1}$, 1234.4 cm$^{-1}$. Melting point: >300.0° C.

3ah $^1$H-NMR (250 MHz DMSO-d$^6$): δ1.31 (s, 9H), 1.44 (s, 9H), 2.11 (s, 2H), 2.83 (t, 2H), 2.96 (t, 2H), 5.80 (bs, 2H), 6.59 (s, 1H), 7.40 (s, 1H), 7.56 (s, 1H), 7.70 (s, 1H), 8.99 (s, 1H), 12.12 (bs, 1H), 13.33 (bs, 1H). $^{13}$C-NMR (62.5 MHz, DMSO-d$^6$): δ 164.5, 157.5, 155.5, 153.8, 145.4, 140.7, 136.1, 133.2, 132.5, 128.2, 127.5, 125.0, 119.4, 117.6, 97.6, 35.1, 34.4, 32.8, 31.8, 30.8, 29.8, 15.2. Formula: $C_{26}H_{34}N_4O_2S$, MS (M+H): 467. HRMS: found (467.2475), calc (467.2480). IR: 3473.8 cm$^{-1}$(bs), 3333.0 cm$^{-1}$(bs), 2956.8 cm$^{-1}$, 2912.5 cm$^{-1}$, 2870.1 cm$^{-1}$, 1711.08 cm$^{-1}$, 1662.6 cm$^{-1}$, 1626.0 cm$^{-1}$, 1500.6 cm$^{-1}$, 1234.5 cm$^{-1}$. Melting point: 239.5-240.5° C.

3ai $^1$H-NMR (400 MHz DMSO-d$^6$): δ 4.04 (s, 2H), 5.87 (bs, 2H, D$_2$O exchangeable), 6.57 (s, 1H), 6.78-7.34 (m, 81-I), 7.49 (s, 1H), 8.94 (s, 1H), 9.26 (bs, 1H, D$_2$O exchangeable), 12.13 (bs, 1H, D$_2$O exchangeable), 12.47 (bs, 1H, D$_2$O exchangeable). $^{13}$C-NMR (100 MHz, DMSO-d$^6$): δ 162.6, 155.5, 154.0, 149.0, 146.0, 145.8, 138.8, 133.4, 132.8, 129.5, 128.7, 126.6, 124.9, 122.9, 120.8, 119.3, 119.2, 117.4, 97.5, 39.0. Formula: $C_{22}H_{18}N_4O_3$, MS (M+H): 387.0. HRMS: found (387.1452), calc (387.1457). IR: 3489.2 cm$^{-1}$ (bs), 3429.4 cm$^{-1}$(bs), 3394.7 cm$^{-1}$(bs), 2941.4 cm$^{-1}$, 2877.8 cm$^{-1}$, 2818.0 cm$^{-1}$, 1656.8 cm$^{-1}$, 1626.0 cm$^{-1}$, 1500.6 cm$^{-1}$, 1465.9 cm$^{-1}$, 1275.0 cm$^{-1}$, 1236.4 cm$^{-1}$. Melting point: 260.0-261.0° C.

3aj-1 $^1$H-NMR (400 MHz CDCl$_3$ and DMSO-d$^6$): δ1.40 (s, 9H), 1.41 (s, 9H), 3.87 (s, 2H), 4.04 (t, 1H), 6.37-7.50 (m, 8H), 8.78 (s, 1H), 8.84 (s, 1H), 10.49 (bs, 1H), 14.09 (bs, 1H), 14.16 (bs, 1H). $^{13}$C-NMR (100 MHz, CDCl$_3$ and DMSO-d$^6$): δ 166.0, 163.8, 161.2, 160.3, 160.0, 137.9, 137.0, 136.9, 135.7, 132.6, 131.6, 131.2, 130.0, 126.7, 119.7, 118.8, 105.5, 103.7, 60.2, 34.9, 29.7. Formula: $C_{30}H_{34}N_4O_3$. MS (M): 498.3. HRMS: found (498.2628), calc (498.2631). IR: 3386.9 cm$^{-1}$(bs), 2955.8 cm$^{-1}$, 2877.8 cm$^{-1}$, 2818.0 cm$^{-1}$, 1680.2 cm$^{-1}$, 1609.6 cm$^{-1}$, 1519.4 cm$^{-1}$, 1430.6 cm$^{-1}$, 1303.4 cm$^{-1}$, 1143.5 cm$^{-1}$. Melting point: 255.0-256.0° C. (Color changed).

3ak-1 $^1$H-NMR (400 MHz CDCl$_3$ and DMSO-d$^6$): δ 1.35 (s, 18H), 1.47 (s, 18H), 4.10 (s, 2H), 4.11 (t, 3H), 6.60 (s, 1H), 6.79 (s, 1H), 7.20-7.47 (m, 4H), 8.63 (s, 1H), 8.67 (s, 1H), 9.38 (bs, 1H), 13.55 (bs, 1H), 13.64 (bs, 1H). $^{13}$C-NMR (100 MHz, CDCl$_3$ and DMSO-d$^6$): δ 169.7, 163.2, 146.4, 145.3, 141.7, 133.1, 132.0, 123.1, 39.8, 38.9, 36.3, 34.2. Formula: $C_{38}H_{50}N_4O_3$. MS (M): 610.4. HRMS: found (610.3883), calc (610.3891). IR: 3489.2 cm$^{-1}$(bs), 3379.4 cm$^{-1}$(bs), 3232.1 cm$^{-1}$(bs), 2957.0 cm$^{-1}$, 2871.0 cm$^{-1}$, 2869.0 cm$^{-1}$, 1709.1 cm$^{-1}$, 1686.0 cm$^{-1}$, 1614.6 cm$^{-1}$, 1515.0 cm$^{-1}$, 1297.5 cm$^{-1}$, 1250.5 cm$^{-1}$. Melting point: 250.0-251.0° C. (Color Changed).

4a $^1$H-NMR (400 MHz DMSO-d$^6$): δ 1.31 (s, 9H), 1.36 (s, 9H), 1.42 (s, 9H), 4.18 (s, 2H) 6.90-7.56 (m, 11H), 7.97 (s, 1H), 8.94 (s, 1H), 9.13 (s, 1H), 13.49 (bs, 1H, D$_2$O exchangeable), 14.01 (bs, 1H, D$_2$O exchangeable) $^{13}$C NMR (100 MHz, DMSO-d$^6$): δ 167.1, 164.9, 160.4, 158.4, 145.0, 140.7, 138.2, 137.8, 137.2, 136.7, 131.7, 130.6, 129.6, 128.6, 128.1, 126.7, 119.6, 118.6, 118.3, 35.1, 34.9, 34.3, 31.7, 29.7, 29.6, 25.7. Formula: $C_{41}H_{46}N_4O_3$. MS (M$^+$): 642.0. HRMS: found (642.3559), calc (642.3570). IR: 3437.2 cm$^{-1}$(bs), 3423.7 cm$^{-1}$(bs), 2955.4 cm$^{-1}$, 2910.6 cm$^{-1}$, 2870.1 cm$^{-1}$, 1658.8 cm$^{-1}$, 1610.6 cm$^{-1}$, 1577.8 cm$^{-1}$, 1431.2.9 cm$^{-1}$, 1392.6.0 cm$^{-1}$, 1195.9 cm$^{-1}$, 1168.9 cm$^{-1}$. Melting point: 251.0-253.0° C.

4b $^1$H-NMR (400 MHz DMSO-d$^6$): δ 1.38 (s, 9H), 4.17 (s, 2H), 6.88-7.88 (m, 13H), 7.96 (s, 1H), 8.90 (s, 1H), 9.11 (s, 1H), 12.12 (bs, 2H), 14.46 (bs, 1H). $^{13}$C-NMR (100 MHz, DMSO-d$^6$): δ 164.7, 164.2, 160.8, 160.5, 155.0, 146.2, 137.9, 137.3, 137.1, 134.4, 132.2, 132.0, 131.7, 131.1, 130.6, 129.7, 128.9, 126.9, 120.5, 119.7, 119.6, 118.7, 118.0, 117.0, 105.7. Formula: $C_{33}H_{30}N_4O_3$. MS (M): 387.0. HRMS: found (530.2320), calc (530.2318). IR: 3425.6 cm$^{-1}$(bs), 3147.8 cm$^{-1}$(bs), 3394.7 cm$^{-1}$(bs), 2920.2 cm$^{-1}$, 2864.3 cm$^{-1}$, 2785.2 cm$^{-1}$, 1660.7 cm$^{-1}$, 1608.6 cm$^{-1}$, 1483.3 cm$^{-1}$, 1384.9 cm$^{-1}$, 1201.7 cm$^{-1}$, 1147.7 cm$^{-1}$. Melting point: 239.0-241.0° C.

4c $^1$H-NMR (400 MHz CDCl$_3$ and DMSO-d$^6$): δ1.30 (s, 9H), 1.37 (s, 9H), 1.40 (s, 9H) 4.17 (s, 2H), 6.89-7.89 (m, 11H), 7.91 (s, 1H), 8.86 (s, 1H), 9.07 (s, 1H), 12.53 (bs, 1H), 13.65 (bs, 1H), 13.68 (bs, 1H). $^{13}$C-NMR (100 MHz, CDCl$_3$ and DMSO-d$^6$): δ 166.8, 166.7, 165.7, 160.7, 160.6, 160.4, 158.1, 154.9, 151.7, 144.6, 140.5, 138.4, 137.7, 137.2, 137.0, 136.3, 132.1, 131.8, 131.5, 131.2, 129.6, 128.7, 128.1, 127.9, 126.7, 119.6, 119.3, 118.9, 118.3, 105.9, 35.0, 34.9, 34.3, 31.9, 31.7, 29.6. Formula: $C_{41}H_{46}N_4O_3$. MS (M$^+$): 642.0. HRMS: found (642.3583), calc (642.3570). IR: 3373.5 cm$^{-1}$ (bs), 2956.9 cm$^{-1}$, 2924.1 cm$^{-1}$, 2866.2 cm$^{-1}$, 1654.9 cm$^{-1}$, 1602.9 cm$^{-1}$, 1275.0 cm$^{-1}$, 1488.8 cm$^{-1}$, 1203.9 cm$^{-1}$, 1174.7 cm$^{-1}$. Melting point: 260.0-262.0° C.

4d $^1$H-NMR (400 MHz CDCl$_3$ and DMSO-d$^6$): δ 1.17 (s, 9H), 1.25 (s, 9H), 1.29 (s, 9H), 2.04 (s, 3H), 2.87 (t, 2H), 3.08 (t, 2H), 6.70-7.54 (m, 7H), 8.52 (s, 1H), 8.61 (s, 1H), 12.13 (bs, 1H), 13.15 (bs, 1H), 13.50 (bs, 1H). $^{13}$C-NMR (100 MHz, CDCl$_3$ and DMSO-d$^6$): δ 165.8, 165.5, 164.2, 160.7, 159.9, 159.8, 158.5, 158.2, 155.3, 144.9, 144.6, 140.5, 140.4, 138.9, 138.6, 137.7, 137.0, 136.9, 131.5, 131.4, 131.2, 130.8, 128.7, 128.1, 127.0, 126.8, 118.8, 118.2, 105.6, 35.0, 34.8, 34.1, 33.1, 30.6, 29.3, 29.2, 15.4. Formula: $C_{37}H_{46}N_4O_3S$. MS (M$^+$): 626.0. HRMS: found (626.3279), calc (626.3291). IR: 3421.7 cm$^{-1}$(bs), 2953.0 cm$^{-1}$(bs), 2914.4 cm$^{-1}$(bs), 2862.4 cm$^{-1}$, 1656.9 cm$^{-1}$, 1610.6 cm$^{-1}$, 1577.8 cm$^{-1}$, 1431.2 cm$^{-1}$, 1313.5 cm$^{-1}$, 1267.2 cm$^{-1}$. Melting point: 244.0-245.0° C. (Color changed).

4e $^1$H-NMR (400 MHz DMSO-d$^6$): δ 1.38 (s, 9H), 2.15 (s, 3H), 2.94 (t, 2H), 3.13 (t, 2H), 6.89-7.99 (m, 9H), 8.92 (s, 1H), 9.13 (s, 1H), 11.99 (bs, 1H), 12.49 (bs, 1H), 14.47 (bs, 1H). $^{13}$C-NMR (100 MHz, DMSO-d$^6$): δ 164.6, 164.1, 160.8, 160.5, 154.8, 146.0, 137.3, 137.1, 134.4, 132.1, 132.0, 131.7, 131.0, 130.6, 120.5, 119.7, 119.6, 118.7, 118.0, 117.0, 105.7, 34.9, 33.2, 30.5, 29.6, 15.2. Formula: $C_{29}H_{30}N_4O_3S$. MS (M$^+$): 514.0. HRMS: found (514.2039), calc (514.2039). IR: 3419.8 cm$^{-1}$(bs), 2914.4 cm$^{-1}$, 2864.3 cm$^{-1}$, 2787.1 cm$^{-1}$, 1658.8 cm$^{-1}$, 1608.6 cm$^{-1}$, 1483.3 cm$^{-1}$, 1392.6 cm$^{-1}$, 1207.4 cm$^{-1}$, 1143.8 cm$^{-1}$. Melting point: 229.0-230.0° C. (Color changed).

4f $^1$H-NMR (400 MHz CDCl$_3$ and DMSO-d$^6$): δ 0.92 (s, 9H), 1.0.1 (s, 9H), 1.04 (s, 9H), 1.80 (s, 3H), 2.62 (t, 2H), 2.82 (t, 2H), 6.46-7.31 (m, 7H), 8.28 (s, 1H), 8.40 (s, 1H). $^{13}$C-NMR (100 MHz, CDCl$_3$ and DMSO-d$^6$): δ 170.4, 170.3, 169.1, 168.6, 165.5, 165.3, 164.9, 163.0, 149.4, 149.3, 145.3, 143.7, 143.4, 142.5, 141.7, 138.9, 136.9, 136.4, 136.2, 135.9, 135.5, 135.3, 133.0, 131.8, 123.9, 123.7, 123.1, 122.7, 39.6, 39.0, 38.0, 37.9, 36.2, 35.4, 34.1, 34.0, 20.2. Formula: C$_{37}$H$_{46}$N$_4$O$_3$S. MS (M$^+$): 626.0. HRMS: found (626.3277), calc (626.3291). IR: 3466.1 cm$^{-1}$(bs), 3329.1 cm$^{-1}$(bs), 2955.0 cm$^{-1}$, 2899.0 cm$^{-1}$, 2873.9 cm$^{-1}$, 1662.6 cm$^{-1}$, 1618.3 cm$^{-1}$, 1492.9.6 cm$^{-1}$, 1427.3 cm$^{-1}$, 1236.4 cm$^{-1}$, 1205.5 cm$^{-1}$, 1172.7 cm$^{-1}$. Melting point: 240.0-241.0 color changed).

4g. $^1$H-NMR (400 MHz CDCl$_3$ and DMSO-d$^6$): δ 0.92 (d, 6H), 1.22 (s, 9H), 1.30 (s, 9H), 1.32 (s, 9H), 2.24 (m, 1H), 2.69 (d, 2H), 6.74-7.58 (m, 7H), 8.58 (s, 1H), 8.66 (s, 1H). 13.23 (bs, 1H), 13.41 (bs, 1H), 13.56 (bs, 1H). $^{13}$C-NMR (100 MHz, CDCl$_3$ and DMSO-d$^6$): δ 165.0, 164.0, 163.0, 160.5, 158.6, 155.7, 144.7, 144.5, 140.5, 138.6, 137.7, 137.6, 137.1, 131.4, 131.1, 130.9, 130.7, 130.5, 128.7, 127.1, 119.1, 118.9, 118.3, 118.1, 117.8, 105.6, 42.1, 35.0, 34.8, 34.1, 31.4, 29.4, 29.3, 26.7, 22.7. Formula: C$_{38}$H$_{48}$N$_4$O$_3$. MS (M$^+$): 608.0. HRMS: found (608.3730), calc (6083726). IR: 3421.7 cm$^{-1}$(bs), 2955.0 cm$^{-1}$(bs), 2910.6 cm$^{-1}$(bs), 2872.0 cm$^{-1}$, 1662.6 cm$^{-1}$, 1606.7 cm$^{-1}$, 1492.9 cm$^{-1}$, 1425.4 cm$^{-1}$, 1317.4 cm$^{-1}$, 1276.9 cm$^{-1}$, 1134.1 cm$^{-1}$, 1089.8 cm$^1$. Melting point: 260.0-261.0° C. (Color changed).

4h $^1$H-NMR (250 MHz DMSO-d$^6$): δ 0.98 (d, 6H), 1.37 (s, 9H), 2.27 (m, 1H), 2.70 (d, 2H), 6.86-7.98 (m, 9H), 8.90 (s, 1H), 9.12 (s, 1H). 12.36 (bs, 1H), 14.01 (bs, 1H), 14.48 (bs, 1H). $^{13}$C-NMR (62.5 MHz, DMSO-d$^6$): δ 164.5, 164.1, 161.9, 161.6, 160.8, 160.5, 155.2, 145.8, 144.5, 137.9, 137.2, 1371, 137.0, 134.3, 132.2, 132.0, 131.6, 131.4, 131.1, 130.7, 130.6, 120.5, 119.7, 119.6, 119.4, 119.1, 118.9, 118.6, 1181, 117.9, 117.0, 105.8, 42.1, 34.9, 29.7, 26.6, 23.1. Formula: C$_{20}$H$_=$N$_4$O$_3$, MS (M$^+$): 496.0. HRMS: found (496.2472), calc (496.2474). IR: 3435.2 cm$^{-1}$(bs), 3423.7 cm$^{-1}$(bs), 2953.0 cm$^{-1}$, 2916.4 cm$^{-1}$, 2868.2 cm$^{-1}$, 1656.9 cm$^{-1}$, 1610.6 cm$^{-1}$, 1473.6 cm$^{-1}$, 1431.2 cm$^{-1}$, 1392.6 cm$^{-1}$, 1276.8 cm$^{-1}$, 1193.9 cm$^{-1}$, 1143.8 cm$^{-1}$. Melting point: 271.0-273.0° C. (Color changed).

4i $^1$H-NMR (400 MHz CDCl$_3$ and DMSO-d$^6$): δ 0.91 (d, 6H), 1.22 (s, 9H), 1.28 (s, 9H), 1.32 (s, 9H), 2.23 (m, 1H), 2.69 (d, 2H), 6.73-7.58 (m, 7H), 8.58 (s, 1H), 8.66 (s, 1H). 13.22 (bs, 1H), 13.41 (bs, 1H), 13.56 (bs, 1H). $^{13}$C-NMR (100 MHz, CDCl$_3$ and DMSO-d$^6$): δ 165.9, 165.2, 163.7, 161.8, 161.6, 160.7, 158.6, 155.7, 144.7, 144.4, 140.5, 138.6, 137.7, 137.6, 137.1, 131.4, 131.1, 131.0, 130.9, 130.7, 130.5, 128.7, 127.1, 119.1, 118.9, 118.3, 118.1, 117.7, 105.5, 42.1, 35.0, 34.8, 34.7, 31.4, 29.3, 29.2, 26.8, 22.7. Formula: C$_{38}$H$_{48}$N$_4$O$_3$. MS (M$^+$): 608.0. HRMS: found (608.3721), calc (608.3726). IR: 3500.0 cm$^{-1}$(bs), 2955.0 cm$^{-1}$(bs), 2912.5 cm$^{-1}$(bs), 2872.0 cm$^{-1}$, 1662.6 cm$^{-1}$, 1604.8 cm$^{-1}$, 1492.9 cm$^{-1}$, 1431.2 cm$^{-1}$, 1356.6 cm$^{-1}$, 1207.4 cm$^{-1}$, 1138.0 cm$^{-1}$. Melting point: 264.0-266.0° C.

4j $^1$H-NMR (400 MHz CDCl$_3$ and DMSO-d$^6$): δ 1.21 (d, 6H), 1.30 (s, 9H), 1.33 (s, 9H), 1.34 (s, 9H), 3.49 (m, 1H), 6.74-7.61 (m, 7H), 8.57 (s, 1H), 8.68 (s, 1H). 12.05 (bs, 1H), 13.22 (bs, 1H), 13.58 (bs, 1H). $^{13}$C-NMR (100 MHz, CDCl$_3$ and DMSO-d$^6$): δ 165.4, 163.5, 160.7, 160.5, 158.6, 158.1, 155.1, 144.7, 144.4, 140.5, 138.5, 137.8, 137.6, 137.1, 131.5, 131.3, 131.0, 130.9, 130.7, 130.4, 128.7, 127.1, 119.1, 118.9, 118.3, 118.2, 118.1, 117.9, 105.4, 35.0, 34.8, 34.1, 31.4, 30.3, 29.4, 29.3, 20.2. Formula: C$_{37}$H$_{46}$N$_4$O$_3$. MS (M$^+$): 594.0. HRMS: found (594.3566), calc (594.3570). IR: 3415.9 cm$^{-1}$(bs), 3138.2 cm$^{-1}$(bs), 2955.0 cm$^{-1}$, 2872.0 cm$^{-1}$, 2792.9 cm$^{-1}$, 1664.6 cm$^{-1}$, 1606.7 cm$^{-1}$, 1489.1 cm$^{-1}$, 1479.4 cm$^{-1}$, 1211.3 cm$^{-1}$, 1184.3 cm$^{-1}$. Melting point: 269.0-271.0° C.

4k $^1$H-NMR (400 MHz CDCl$_3$ and DMSO-d$^6$): δ 1.27 (d, 6H), 1.38 (s, 9H), 3.51 (m, 1H), 6.89-7.99 (m, 9H), 8.91 (s, 1H), 9.16 (s, 1H). 12.06 (bs, 1H), 12.43 (bs, 14.52 (bs, 1H). $^{13}$C-NMR (100 MHz, CDCl$_3$ and DMSO-d): δ 164.6, 164.1, 161.0, 160.9, 160.6, 160.5, 154.6, 145.9, 137.2, 137.1, 134.4, 133.1, 132.0, 131.7, 131.0, 130.6, 120.6, 120.1, 119.7, 119.6, 119.5, 118.7, 118.1, 117.9, 117.2, 117.0, 105.6, 34.9, 30.4, 29.6, 20.6. Formula: C$_{29}$H$_{30}$N$_4$O$_3$, MS (M): 482.0. HRMS: found (482.2313), calc (482.2318). IR: 3448.7 cm$^{-1}$(bs), 3145.9 cm$^{-1}$(bs), 2958.8 cm$^{-1}$, 2870.1 cm$^{-1}$, 2794.9 cm$^{-1}$, 1658.8 cm$^{-1}$, 1610.6 cm$^{-1}$, 1481.3 cm$^{-1}$, 1384.9 cm$^{-1}$, 1207.4 cm$^{-1}$, 1147.7 cm$^1$. Melting point: 265.0-267.0° C.

4l $^1$H-NMR (400 MHz CDCl$_3$ and DMSO-d$^6$): δ 1.19-1.30 (m, 33H), 3.47 (m, 1H), 6.72-7.59 (m, 7H), 8.57 (s, 1H), 8.67 (s, 1H). 12.02 (bs, 1H), 13.35 (bs, 1H), 13.43 (bs, 1H). $^{13}$C-NMR (100 MHz, CDCl$_3$ and DMSO-d$^6$): δ 166.0, 165.4, 164.2, 160.7, 158.3, 155.0, 144.3, 140.4, 138.8, 137.7, 136.9, 131.5, 131.1, 131.0, 130.8, 128.1, 126.9, 118.9, 118.3, 118.2, 117.9, 105.5, 34.9, 34.7, 34.1, 31.3, 30.3, 29.3, 29.2, 20.1. Formula: C$_{37}$H$_{46}$N$_4$O$_3$. MS (M$^+$): 594.0. HRMS: found (594.3572), calc (594.3570). IR: 3417.9 cm$^{-1}$(bs), 3142.0 cm$^{-1}$(bs), 2956.9 cm$^{-1}$, 2877.8 cm$^{-1}$, 2868.2 cm$^{-1}$, 1656.9 cm$^{-1}$, 1606.7 cm$^{-1}$, 1469.8 cm$^{-1}$, 1433.1 cm$^{-1}$, 1209.4 cm$^{-1}$, 1172.7 cm$^{-1}$. Melting point: 258.0-260.0° C.

Example 2

References 1. (a) Jacobsen, E. N.; Kakiuchi, F.; Konsler, R. G.; Larrow, J. F.; Tokunaga, M. *Tetrahedron Lett.* 1997, 38, 773. (b) Wu, M. H.; Jacobsen, E. N. *J. Org. Chem.* 1998, 63, 5252. (c) Wu, M. H.; Hansen, K. B.; Jacobsen, E. N. *Angew. Chem. Int. Ed.* 1999, 38, 2012. (d) Gigante, B.; Corma, A.; Garcia, H.; Sabater, M. J. *Catal. Lett.* 2000, 68, 113.

2. (a) Irk, R.; Noda, K.; Ito, Y.; Matsumoto, N.; Katsuki, T. *Tetrahedron Lett.* 1990, 31, 7345. (b) Zhang, W.; Loebach, J. L.; Wilson, S. R.; Jacobsen, E. N. *J. Am. Chem. Soc.* 1990, 112, 2801. (c) Holbach, M.; Week, M.; *J. Org. Chem.* 2006, 71, 1825.

3. (a) Kumar, P.; Naidu, V.; Gupta, P. *Tetrahedron* 2007, 63(13), 2745. (b) Brandes, B. D.; Jacobsen, E. N. *Tetrahedron: Asymmetry* 1997, 8, 3927. (c) Breinbauer, R.; Jacobsen, E. N. *Angew. Chem. Int. Ed.* 2000, 39, 3604. (d) Annis, D. A.; Jacobsen, E. N. *J. Am. Chem. Soc.* 1999, 121, 4147.

4. (a) Schwas, S. E.; Branalt, J.; Jacobsen, E. N. *J. Org. Chem.* 1998, 63, 403. (b) Chapman, J. J.; Day, C. S.; Welker, M. E. *Eur. J. Org. Chem.* 2001, 12, 2273. (c) Mellah, M.; Ansel, B.; Patureau, F.; Voituriez, A.; Schulz, E; *Journal of Molecular Catalysis A: Chemical.* 2007, 272, 20.

5. (a) Taylor, M. S.; Jacobsen, E. N. *J. Am. Chem. Soc.* 2004, 126, 10558. (b) Jayasree, S.; Majeed, S. A.; Benjamin L. *J. Am. Chem. Soc.* 2006, 128(4), 1086.

6, (a) Sigman, M. S.; Jacobsen, E. N. *J. Am. Chem. Soc.* 1998, 120, 5315. (b) Vachal, P.; Jacobsen, E. N. *Org. Lett.* 2000, 2, 867. (c) Yan, M.; Xu, Q. Y.; Chan, A. S. C. *Tetrahedron: Asymmetry* 2000, 11, 845. (d) Belokon, Y. N.; North, M.; Parsons, T. *Org. Lett.* 2000, 2, 1617. (e) Belokon, Y. N.; Green, B.; Ikonnikov, N. S.; North, M.; Parsons, T.; Tararov, V. I. *Tetrahedron* 2001, 57, 771.

7. (a) Marzano, C.; Pellei, M.; Colavito, D.; Alidori, S.; Lobbia, G. G.; Gandin, V.; Tisato, F.; Santini, C., *J. Med. Chem.* 2006, 49, 7317. (b) Bregman, H.; Williams, D. S.; Atilla, G. E.; Carroll, P. J.; Meggers, E., *J. Am. Chem. Soc.* 2004, 126(24), 13594. (c). Doctrow, S. R.; Huffman, K.; Marcus, C. B.; Tocco, G.; Malfroy, E.; Adinolfi, C. A.; Kruk, H.; Baker, K.; Lazarowych, N.; Mascarenhas, J.; Malfroy, B., *J. Med. Chem.* 2002, 45, 4549.
8. Wu, X. H.; Gorden, A. E. V. *J. Comb. Chem.* 2007, 9, 601.
9. (a) Zhang, L.; Liu, G.; Zhang, S, D.; Yang, H. Z.; Li, L.; Wu, X. H.; Yu, J. L.; Kou, B. B.; Xu, S.; Li, J.; Sun, G. C.; Ji, Y. F.; Cheng, G. F. *J. Comb. Chem.* 2004, 6, 431. (b) Perez, C.; Lopez, de C. A.; Bello, *J. Food Chem. Toxicol.* 2002, 40, 1463. (c) Mensah-Osman, E. J.; AL-Katib, A. M.; Dandashi, M. H.; Mohammad, R. M. Mol. *Cancer. Ther.* 2002, 1, 1315. (d) Seitz, L. E.; Suling, W. J.; Reynolds, R. C. *J. Med. Chem.* 2002, 45, 5604. (e) Burke, J. R.; Pattoli, M. A.; Gregor, K. R.; Brassil, P. J.; MacMaster, J. F.; McIntyre, K. W.; Yang, X.; Iotzova, V. S.; Clarke, W.; Strnad, J.; Qiu, Y.; Zusi, F. C. *J. Biol. Chem.* 2003, 278, 1450.
10. Jaung, J. Y., *Dyes and Pigments* 2006, 71(3), 245.
11. Schaper, W. W.; Lothar, R. C.; Erwin, H.; Eckhard, R.; Dirk, S.; U.S. Pat. Appl. Publ. 2005, US2005256000 A1 20051117 CAN 143:454394 AN 2005:1224419, 97.
12. (a) Pan, S. C.; List, B. *Org. Lett.* 2007, 9, 1149. (b) Pan, S. C.; Zhou, J.; and List, B. *Angew. Chem. Int. Ed.* 2007, 46, 612. (c) Rossi, J. C.; Marull, M.; Boiteau, L.; Taillades, J. *Eur. J. Org. Chem.* 2007, 662. (d) Huguenot, F.; Brigand. T. *J. Org. Chem.* 2006, 71, 7075. (e) Wang, H.; Zhao, X. M.; Li, Y. H.; Lu, L. *Org. Lett.* 2006, 8, 1379. (f) Martnez, R.; Ramon, D. J.; Yus, M. *Tetrahedron Lett.* 2005, 46, 8471.
13. (a) Vilaivan, T.; Bhanthumnavin, W.; Sritana-Anant, Y. *Curr. Org. Chem.* 2005, 9, 1315. (b) Kobayashi, S.; Ishitani, H. *Chem. Rev.* 1999, 99, 1069. (c) Arend, M. *Angew. Chem. Int. Ed.* 1999, 38, 2873. (d) Bloch, R. *Chem. Rev.* 1998, 98, 1407. (e) Enders, D.; Reinhold, U. *Tetrahedron: Asymmetry* 1997, 8, 1895, (f) Alvaro, G.; Savoia, D. *Syn. Lett.* 2002, 651.
14. (a) Jacobsen, E. N.; Kakiuchi, F.; Konsler, R. G.; Larrow, J. F.; Tokunaga, M., *Tetrahedron Lett.* 1997, 38, 773. (b) Wu, M. H.; Jacobsen, E. N. *J. Org. Chem.*, 1998, 63, 5252. (c) Wu, M. H.; Hansen, K. B.; Jacobsen, E. N. *Angew. Chem., Int. Ed.* 1999, 38, 2012.
15. Johann, H.; Martin, K.; PCT Int. Appl. 2007, 57, WO 2007017284 A2 20070215 CAN 146:252109 AN 2007: 174055.
16. Pettersen, E. O.; Larsen, R. O.; Domish, J. M.; Borretzen, B.; Oftebro, R.; Ramdahl, T.; Moen, V. Eur. Pat. Appl. 1994, 26, EP 609032 A1 19940803 CAN 121:179238 AN 1994: 579238.
17. Hudson, M. J.; Knowles, J. P.; Harris, P. J. F.; Jackson, D. B.; Chinn, M. L.; Ward, S. *Microporous and Mesoporous Materials.* 2004, 75, 121.
18. (a) Prugh, J. D.; Birchenough, L. A.; Egbertson, M. S. *Synth. Commun.* 1992, 22, 2357. (b) Look, G. C.; Murphy, M. M.; Campbell, D. A.; Gallop, M. A. *Tetrahedron Lett.* 1995, 36(17) 2937. (c) Mooteoa, D. R.; Fraser-Reid, B. *Tetrahedron Lett.* 1989, 30(18), 2363.
19. (a) Peukert, s.; and Jacobsen, E. N.; *Org. lett,* 1999, 1, 1245.
20. Love, B. E.; Ren, J. H. *J. Org. Chem.* 1993, 58, 5556.
21. Frisch, M. J.; Trucks, G. W.; Schlegel, H. B.; Scuseria, G. E.; Robb, M. A.; Cheeseman, J. R.; Montgomery, J. A., Jr.; Vreven, T.; Kudin, K. N.; Burant, J. C.; Millam, J. M.; Iyengar, S. S.; Tomasi, J.; Barone, V.; Mennucci, B.; Cossi, M.; Scalmani, G.; Rega, N.; Petersson, C. T. A.; Nakatsuji, H.; Hada, M.; Ehara, M.; Toyota, K.; Fukuda, R.; Hasegawa, J.; Ishida, M.; Nakajima, T.; Honda, Y.; Kitao, O.; Nakai, H.; Klene, M.; Li, X.; Knox, J. E.; Hratchian, H. P.; Cross; J. B.; Bakken, V.; Adamo, C.; Jaramillo, j.; Gomperts, R.; Stratmann, R. E.; Yazyev, O.; Austin, A. J.; Cammi, R.; Pomelli, C.; Ochterski, J. W.; Ayala, P. Y.; Morokurna, K.; Voth, G. A.; Salvador, P.; Dannenberg, J. J.; Zakrzewski, V. G.; Dapprich, S.; Daniels, A. D.; Strain, M. C.; Farkas, O.; Malick, D. K.; Rabuck, A. D.; Raghavachari, K.; Foresman, J. B.; Ortiz, J. V.; Cui, Q.; Baboul, A. G.; Clifford, S.; Cioslowski, J.; Stefanov, B. B.; Liu, G.; Liashenko, A.; Piskorz, P.; Komaromi, L; Martin, R. L.; Fox, D. J.; Keith, T.; Al-Laham, M. A.; Peng, C. Y.; Nanayakkartt, A.; Challacombe, M.; Gill, P. M. W.; Johnson, B.; Chen, W.; Wong, M. W.; Gonzalez, C.; Pople, J. A. *Gaussian* 03, reVision D.01; Gaussian, Inc.: Wallingford, Conn., 2004.
22. Cossi, M.; Rega, N.; Scalmani, G.; Barone, V. *J. Comput. Chem.* 2003, 24, 669.
23. Breneman, C. M.; Wiberg, K. B. *J. Comput. Chem.* 1990, 11, 361.

Example 3

Reference is made to Wu e al., "Synthesis and Characterization of 2-Quinoxalinol Schiff-Base Metal Complexes," Inorganica Chimica Acta, Volume 362, Issue 6, 20 Apr. 2009, Pages 1847-1854, the content of which is incorporated herein by reference in its entirety.

Abstract

The reaction of uranyl acetate with (2,2'-(1E,1'E)-(2-benzyl-3-hydroxyquinoxaline-6,7 diyl) bis(azan-1-yl-1-ylidene) bis(methan-1-yl-1-ylidene)diphenol) ($H_2L1$) at room temperature in methanol and chloroform yields the $UO_2L1$ complex. Crystals were grown through solvent diffusion of the ligand-metal complex in dimethyl formamide with diethyl ether to prepare: $UO_2L1 \cdot DMF$ (1). Complexes with 2,2'-(1E,1'E)-(2-benzyl-3-hydroxyquirioxaline-6,7-diyl)bis (azan-1-yl-1-ylidene)bis(methan-1-yl-1-ylidene)dibenzene-1,4-diol, ($H_2L2$) and 2,2'-(1E,1'E)-(2-hydroxy-3-isopropylquinoxaline-6,7-diyl)bis(azan-1-yl-1-ylidene)bis(methan-1-yl-1-ylidene)diphenol ($H_2L3$) were also prepared, and crystals of the uranyl complexes ($UO_2L2 \cdot DMF$ (2) and (3)) grown from DMF/ether. A fourth complex $UO_2L4 \cdot H_2O$ (4) was prepared through layering a solution of the tetra-tert butyl substituted 2-quinoxalinol salen ligand $H_2L4$ in acetone with an aqueous solution containing uranyl acetate. The complexes exhibit a symmetric core featuring a slightly distorted bicapped pentagonal geometry around the uranium center with two oxo-groups and two imine groups from the ligand chelating the ligand and the fifth site in the coordination plane of the ligand occupied by a solvent molecule. These compounds were characterized using solution (NMR and UV-Vis) and solid-state (IR, X-ray crystallography) techniques. Complexes of $H_2L4$ with early transition metals; $Mn^{2+}$, $Co^{2+}$, $Ni^{2+}$, and $Cu^{2+}$ also were prepared and characterized for comparison of solution and spectroscopic characteristics.

Introduction

One proposal to limit greenhouse gases is to increase the use of electrical power production using nuclear fuels; however, this has caused wide spread public concern about the possible health hazards that might result from environmental contamination with the actinides (U, Np, Pu), which are both radioactive and chemically toxic heavy metals. Prolonged exposure or ingestion of quantities of uranium, principally found as uranyl ion ($UO_2^{2+}$) under environmental or aqueous conditions, can lead to damage of kidney and/or liver function, through a mechanism much like other heavy metals. A resurgence of interest in actinide coordination chemistry is founded on improving understanding of environmental transport and long term storage solid forms in order to better address these health and environmental concerns. Here, a new series of ligands incorporating a quinoxaline into a salen backbone were synthesized. These new ligands may be used to facilitate remediation of contaminated sites and for decontamination applications.

Various ligand systems have been proposed for the selective extraction of uranium including organic phosphorus oxides, crown ethers, calixarenes, and Schiff bases. Many of these have also been proposed for use in actinide selective sensors; however, their use in applications might be limited by sensitivity, signal response, and competition from other metals. A good sensor for uranium must be: highly selective, provide a large signal response, and allow for isolation and recovery of the metal. New ligand systems will be required that can both address these limitations in a variety of solvent and pH conditions and that possess the capacity to allow for modifications to tailor selectivity or solubility for incorporation into applications.

While using the inherent radioactivity of the actinides is one way to detect these radioactive heavy metals, the methods to remediate wastes from medical radioactive waste would be very different than cleaning up materials containing actinides from nuclear fuels. Typical handheld radiation detectors could not distinguish between the two. A Geiger counter only detects beta and gamma emissions, not alpha emissions, and while uranium emits both alpha and beta emissions, $Tc^{99}$ (used in medical tracer studies), is a strong beta emitter. This might lead one to not realize the quantities of radioactive material present. Also, some isotopes such as $^{239}Pu$ are entirely alpha-emitters, and would not be detected by a Geiger counter, since these are β and γ-emission detectors. Only the daughter products would be detected. Finally, emissions could be masked by the presence of other metals or in solutions. Uranium has a natural fluorescence, but this is reduced or quenched in some minerals containing other metals. A chemical or fluorescent sensor could be useful in rapid field identification of actinides and in decontaminations and could increase sensitivity of detection by reducing detection limits.

Currently used methods for the determination of heavy metal ion concentration in groundwater and soils are based on atomic absorption spectroscopy (AA), but this technique has a low sensitivity for uranium. Kinetic phosphorimetry (KPA) or ultraviolet-visible spectroscopy (UV-Vis) with a coordinating dye such as Arsenazo III have improved sensitivity, but both techniques are complicated by organic compounds and require that samples be purified prior to measurements. Other ligand systems found to be selective for uranyl ($UO_2^{2+}$) demonstrate a false signal with first row transition metals, in particular $Cu^{2+}$. Thus, detection and quantification of uranium from environmental samples can be quite complicated, and it is dependent on purification of the sample prior to measurement.

In the design of the 2-quinoxolinol salen ligands, the addition of a quinoxaline functionality to the salen imparts the fluorescence of the quinoxaline and alters the flexibility or the coordination site through the addition of the aromatic backbone. This aromatic system will also contribute to the intensity of absorption in the UV-Vis of the complex. Salen or salophen ligands have been used as transition metal complexes in a variety of applications. For example, Cu, Mn, or Ru complexes have been used as catalysts in the catalytic oxidation of secondary amines, in enantioselective catalysts, and as catalysts for ring-opening metathesis. Uranyl metal salophens have been used in molecular recognition studies as anion receptors or in other studies probing chemical reactivity of the metal complex.

Therefore, 2-quinoxalinol ligands were prepared and modified for use in recognizing uranyl. A Schiff-base condensation of a benzaldehyde with the diaminoquinoxaline results in ligands based on the skeleton 2,2'-(1E,1'E)-(quinoxaline-6,7 diylbis (azan-1-yl-1-ylidene)) bis(methan-1-yl-1-ylidene) diphenol. (Scheme 4.) Here, four uranyl metal complexes with 2-quinoxalinol salen ligands are reported and are characterized by X-ray diffraction. (Sec Scheme 5.) All of the metal complexes are characterized by $^1$H-NMR or mass spec, and compared with ultraviolet-visible spectroscopy. Complexes with early transition metals are also described with $Mn^{2+}$, $Co^{2+}$, $Ni^{2+}$, and $Cu^{2+}$ to compare the spectroscopy of the complexes. (See Scheme 6.) The results described here will contribute to the development of actinide selective sensors.

Scheme 4. Scheme depicting the synthesis of the 2-quinoxolinol salen ligands described within the text.

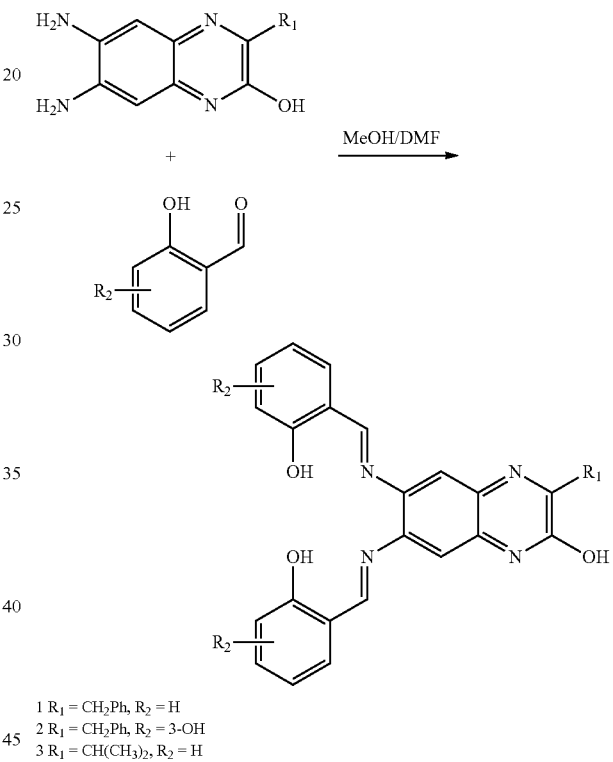

1 $R_1$ = $CH_2Ph$, $R_2$ = H
2 $R_1$ = $CH_2Ph$, $R_2$ = 3-OH
3 $R_1$ = $CH(CH_3)_2$, $R_2$ = H
4 $R_1$ = $CH_2Ph$, $R_2$ = 3,5-Di-tert butyl Scheme 5. Reaction scheme for synthesis of Uranyl ($UO_2^{2+}$) quinoxolinol salen complexes.

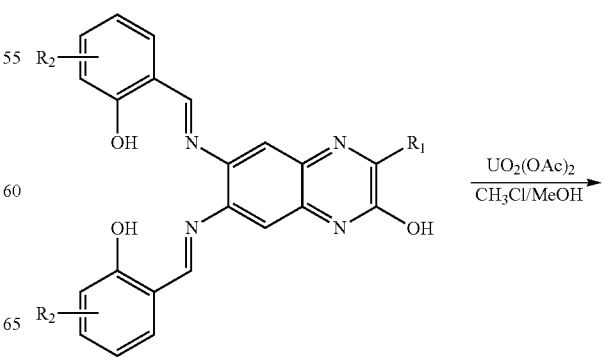

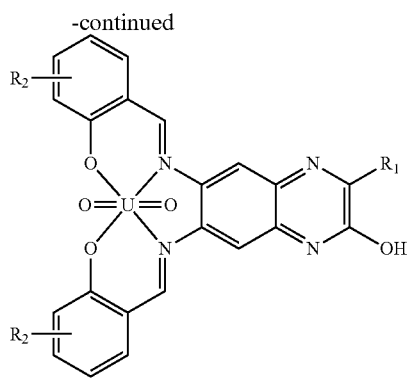

1 R₁ = CH₂Ph, R₂ = H
2 R₁ = CH₂Ph, R₂ = 3-OH
3 R₁ = CH(CH₃)₂, R₂ = H
4 R₁ = CH₂Ph, R₂ = 3,5-Di-tert butyl Scheme 6. Reaction scheme depicting the synthesis and numbering scheme for the 2-quinoxolinol transition metal complexes described

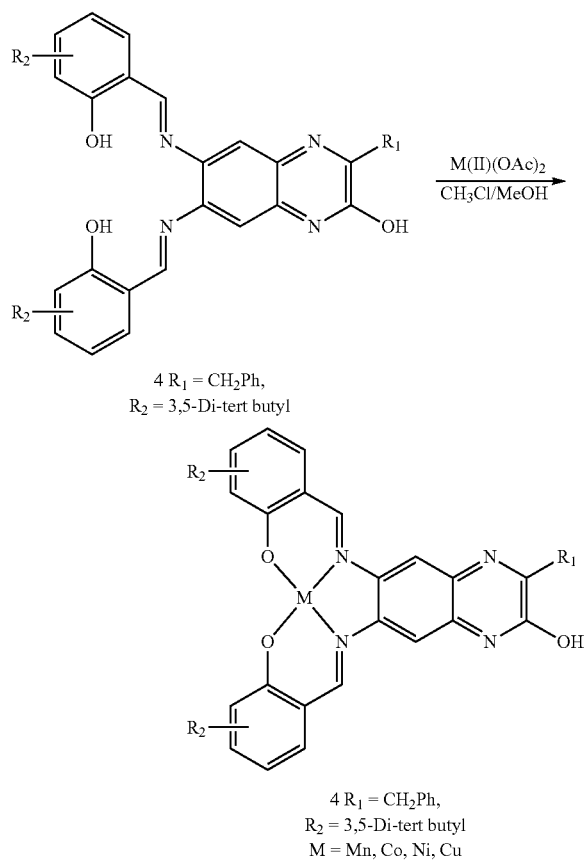

4 R₁ = CH₂Ph,
R₂ = 3,5-Di-tert butyl

4 R₁ = CH₂Ph,
R₂ = 3,5-Di-tert butyl
M = Mn, Co, Ni, Cu

Experimental Section
General Procedure

Aminoacid methyl esters, difluorodinitrobenzene (DFDNB), HCl (37%) and functionalized salicylaldehydes were purchased from Acros Organics Co. Ammonium hydroxide (5.0 N), palladium on carbon (wet, 5%) was purchased from Sigma-Aldrich Co. Copper (II) acetate, Ni (II) acetate, Mn (II) acetate, Co (II) acetate, uranyl ($UO_2^{2+}$) acetate not currently available were purchased from Sigma-Aldrich Co. Starting materials were used as received. All organic solvents were purchased from Thermo Fisher Scientific Co. and were used directly for synthesis.

Reaction progress was monitored by thin-layer chromatography (TLC) using 0.25 mm Whatman Aluminum silica gel 60-F254 precoated plates with visualization by irradiation with a Mineralight UVGL-25 lamp. All melting points were recorded on a MeI-temp II melting point apparatus, and the values were uncorrected. The $^1H$ and $^{13}C$ NMR spectra were recorded on Bruker AV 400 spectrometer with d6-DMSO and d4-MeOH as solvents with tetramethylsilane as the reference (operated at 400 and 100 MHz, respectively). Chemical shifts are reported as δ values (ppm). Electrospray ionization mass spectrometry was performed on a Micromass QTOF mass spectrometer (Waters Corp, Milford Mass.). Direct probe samples were on a VG-70S mass spectrometer (Waters Corp, Milford Mass.). All UV data was collected using a Cary 50 UV-Vis spectrophotometer with a xenon lamp and an equipment range from 200 to 1250 nm. The IR data were recorded as KBr pellets on SHIMADZU Inc. IR, Prestige-21 Fourier Transform Infrared Spectrophotometer in the range 400-4000 cm⁻¹.

Ligand Synthesis

The ligands were prepared using a procedure modified from the literature. To 1.0 equiv (0.1 mmol) of the diamino-2-quinoxalinol intermediate dissolved in 4 mL methanol, a solution of 10.0 equiv (1 mmol) salicylaldehyde in. 6 mL methanol was added. After heating at reflux temperature for 48 hours, a dark yellow product precipitates. The precipitate was filtered and washed with 95% ethanol and cold acetone 5 times to obtain the final product. The yield of final products was close to 80% with the purity 95%. All of the products were identified by $^{13}C$, $^1H$-NMR, IR, HRMS, and UV-Vis.

Synthesis of Metal Complexes

[UO₂(L1).DMF] (1): To a solution of H₂L1 (23.7 mg, 0.25 mmol) in 10 mL MeOH and CHCl₃(1:1) uranyl acetate (UO₂(OAc)₂·2H₂O, 25.5 mg, 0.06 mmol) was added and stirred at room temperature for two hours. The solution was concentrated and washed with 95% EtOH to obtain 1. Yield: 80.7% (30.0 mg); $δ_H$(400 MHz DMSO-d⁶): δ 4.20 (s, 2H), 6.73-6.77 (t, 2H), 7.00-7.04 (t, 2H), 7.24-7.88 (m, 10H), 8.12 (s, 1H), 9.60 (s, 1H), 9.76 (s, 1H), 12.67 (bs, 1H). HRMS: obs: 784.2280, calc: 784.2285 (M+H+ CH₃CN). ν (KBr)/cm⁻¹: 3397, 3337, 2965, 1657, 1620, 1582, 1545, 1491, 1445, 1204, 1144, 1040 cm⁻¹. UV-Vis (DMSO): 290 nm (∈=2.0×10⁴), 370 nm (∈=1.5×10⁴). A portion of the dark red solid (10 mg) was dissolved in 1 mL dimethylformamide (DMF) and put into a vial. Into this, diethyl ether was allowed to diffuse into from an outer vial. After 2 weeks, the formation of red crystals as thin needles was observed.

[UO₂(L2).DMF] (2): To a solution of H₂L2 (25.3 mg, 0.05 mmol) in 6 mL DMF and MeOH (50:50), uranyl acetate (UO₂(OAc)₂·2H₂O, 25.5 mg, 0.06 mmol) was added and the resulting mixture was stirred at room temperature for two hours. The solution was concentrated and washed with 95% EtOH to obtain 2. Yield: 85.9% (33.3 mg); $δ_H$ (400 MHz DMSO-d⁶): δ 4.22 (s, 2H), 6.54-8.67 (m, 13H), 9.55 (s, 1H), 9.71 (s, 1H), 11.77 (bs, 1H), 11.82 (bs, 1H), 12.69 (bs, 1H). HRMS: obs: 816.2178, calc: 816.2183 (M+H+CH₃CN). ν (KBr)/cm⁻¹: 3397, 3337, 2965, 1657, 1620, 1582, 1545, 1491, 1445, 1204, 903 cm⁻¹. UV-Vis (DMF): 365 nm (∈=1.10×10⁴), A portion of the dark red solid (10 mg) was dissolved in 1 mL of dimethylformamide (DMF) in a vial. Into this diethyl ether was allowed to diffuse into from an outer vial. After 2 weeks, the formation of red crystals as thin needles was observed.

[UO$_2$(L3).DMF] (3): To a solution of H$_2$L3 (106.6 mg, 0.25 mmol) in 60 mL MeOH and 100 mL THF, uranyl acetate (UO$_2$(OAc)$_2$.2H$_2$O, 130 mg, 0.30 mmol) was added. The solution turned dark red upon addition of metal salt. After stirring at room temperature for 2 hours, the solution was concentrated and washed with 95% EtOH. Yield: 97.8% (170 mg). $\delta_H$ (400 MHz DMSO-d$^6$): δ 1.28 (d, 6H), 3.56 (m, 1H), 6.74-8.17 (m, 10H), 9.61 (s, 1H), 9.81 (s, 1H), 12.58 (bs, 1H). HRMS: obs: 736.2280, calc: 736.2285 (M+H-1-CH$_3$CN). ν (KBr)/cm$^{-1}$: 3406, 2967, 1655, 1601, 1539, 1464, 1441, 1263, 1146, 899 cm$^{-1}$. UV-Vis (DMF): 287 nm (∈=1.7×10$^4$), 304 nm (∈=1.6×10$^4$), 360 nm (∈=1.3×10$^4$), 385 nm (∈=1.3×10$^4$), 419 nm (c=1.4×10$^4$). A portion of the dark red solid (10 mg) was dissolved in 1 mL dimethylformamide (DMF) and put into a vial. Into this, diethyl ether was allowed to diffuse into from an outer vial. After 2 weeks, the formation of red crystals as thin needles was observed.

[UO$_2$(L4).H$_2$O] (4): To a solution of H$_2$L4 (35.0 mg, 0.05 mmol) in 6 mL MeOH and 6 mL CHCl$_3$, uranyl acetate (UO$_2$(OAc)$_2$.2H$_2$O, 25.5 mg, 0.06 mmol) was added. The solution turned dark red upon addition of metal salt. After stirring at room temperature, for 2 hours, the solution was concentrated. Yield: 77.1% (37.3 mg). In a second preparative method, an aqueous solution of uranium acetate (10 mg in 1 mL) was layered with a saturated acetone solution of ligand H$_2$L4 (10 mg in 1 mL). The acetone solution was seen to turn red at the interface. After one week, crystals as red rods were seen to form at the interface of the two layers, and the crystalline material was collected (Yield: 80%). This was identified as [UO$_2$(L4).H$_2$O] and characterized by XRD. $\delta_H$ (400 MHz CDCl$_3$+DMSO-d$^6$): δ 1.19 (s, 18H), 1.64 (s, 18H), 4.11 (s, 2H), 7.09-7.63 (m, 10H), 7.70 (s, 1H), 9.19 (s, 1H), 9.32 (s, 1H), 12.18 (bs, 1H). HRMS: obs: 967.4514, calc: 967.4524 (M+H). ν (KBr)/cm$^{-1}$: 3433, 2957, 1655, 1620, 1383, 1283, 1229, 1153, 937, 760 cm$^{-1}$. UV-Vis DMSO: 295 nm (∈=2.5×10$^4$), 375 nm (∈=1.6×10$^4$), and 440 nm (∈=1.5×10$^4$).

[Co(L4).MeOH] (5): To a solution of H$_2$L4 (70 mg, 0.10 mmol) in 10 mL MeOH and CHCl$_3$(1:1) an 1.1 molar amount of cobalt II acetate (Co(OAc)$_2$.4 H$_2$O, 27 mg, 0.11 mmol) was added. After heating to reflux temperature for 12 hours, the solution was concentrated and washed with 95% EtOH. A dark black/blue precipitate was obtained by filtering. Yield: 79.4% (60.0 mg); HRMS: obs: 755.3369, calc: 755.3372 (M$^+$)). ν (KBr)/cm$^{-1}$: 3066, 2957, 1665, 1614, 1572, 1524, 1501, 1462, 1410, 1256, 1180, 1128 cm$^{-1}$. UV-Vis (dichloromethane): 322 nm (∈=6.15×10$^4$), 437 nm (∈=7.08×10$^4$).

[Cu(L4).MeOH] (6): To a solution of H$_2$L4 (70 mg, 0.10 mmol) in 10 mL MeOH and CHCl$_3$(1:1), copper II acetate (Cu(OAc)$_2$.1 H$_2$O, 22 mg, 0.11 mmol) was added. After heating to reflux temperature for 12 hours, the solution was concentrated and washed with 95% EtOH. A dark precipitate was obtained by filtering. Yield: 82.8% (63 mg); HRMS: obs: 760.3413, calc: 760.3422 (M$^+$). ν (KBr)/cm$^{-1}$: 3067, 2955, 1661, 1586, 1528, 1491, 1416, 1377, 1260, 1209, 1173, 1130 cm$^{-1}$. UV-Vis (dichloromethane): 286 nm (∈=6.13×10$^4$), 330 nm (∈=7.54×10$^4$), 458 nm (∈=9.14×10$^4$). DMSO: 280 nm (∈=3.4×10$^4$), 32 5 nm (∈=2.8×10$^4$), and 454 nm (∈=1.5×10$^4$).

[Ni(L4).MeOH] (7): To a solution of H$_2$L4 (70.0 mg, 0.10 mmol) in 10 mL MeOH and CHCl$_3$(1:1), nickel 11 acetate (Ni(OAc)$_2$.4 H$_2$O, 27 mg, 0.11 mmol) was added. After heating to reflux temperature for 12 hours, the solution was concentrated and washed with 95% EtOH. A green/brown precipitate was obtained by filtering. Yield: 92.7% (70 mg); HRMS: obs: 755.3461, calc: 755.3471 (M$^+$)). ν (KBr)/cm$^{-1}$: 3067, 2955, 2870, 1665, 1616, 1584, 1533, 1598, 1464, 1414, 1379, 1260, 1182, 1130 cm$^-$. UV-Vis (dichloromethane): 268 nm (∈=4.66×10$^4$), 314 nm (∈=4.81×10$^4$), 388 nm (∈=5.78×10$^4$), 452 nm (∈=9.24×10$^4$).

[Mn(L4).MeOH] (8): To a solution of H$_2$L4 (70.0 mg, 0.10 mmol) in 10 mL MeOH and CHCl$_3$(1:1), manganese II acetate (Mn(OAc)$_2$.4 H$_2$O, 27 mg, 0.11 mmol) was added. After heating to reflux temperature for 12 hours, the solution was concentrated and washed with 95% EtOH. A dark brown precipitate was obtained by filtering. Yield: 96.5% (72.5 mg); HRMS: obs: 751.3420, calc: 751.3429 (M$^+$). ν (KBr)/cm$^{-1}$: 3385, 3248, 3208, 2955, 2911, 1670, 1582, 1532, 1462, 1416, 1317, 1248, 1177, 1130 cm$^{-1}$. UV-Vis (dichloromethane): 372 nm (∈=4.06×10$^4$), 510 nm, (∈=7.13×10$^4$).

Crystal Growth and X-ray Crystallography

Crystals of uranyl metal complexes UO$_2$L1.DMF, UO$_2$L2.DMF, and UO$_2$L3.DMF were obtained in good yield from slow diffusion of diethyl ether into a solution of the metal complex in dimethyl formamide at room temperature. Crystals of the UO$_2$L4.H$_2$O were grown by layering an aqueous solution of uranyl acetate with a solution of ligand H$_2$L4 in acetone. Crystal of complexes with the first row transition metals were found to not, be of a suitable quality for characterization by X-ray diffraction. X-ray diffraction data for UO$_2$L1.DMF, UO$_2$L2.DMF. UO$_2$L3.DMF. and UO$_2$L4.H$_2$O were collected at −80° C. on a Bruker SMART APEX CCD X-ray diffractometer unit using Mo Kα radiation from crystals mounted in Paratone-N oil on glass fibers. SMART (v 5.624) was used for preliminary determination of cell constants and data collection control. Determination of integrated intensities and global cell refinement were performed with the Bruker SAINT Software package using a narrow-frame integration algorithm. The program suite SHELXTL (v 6.12) was used for space group determination, structure solution, and refinement. Refinement was performed against F$^2$ by weighted full-matrix least square, and empirical absorption correction (SADABS Sheldrick, G. M., SADABS—An empirical absorption correction program; Bruker Analytical X-ray Systems Madison, Wis., 1996.) were applied. H atoms were placed at calculated positions using suitable riding models with isotropic displacement parameters derived from their carrier atoms. Crystal data, selected bond distances and angles, are provided in Tables 6 and 7. Crystallography data for structural analysis of uranyl complexes of compounds UO$_2$L1.DMF, UO$_2$L2.DMF. UO$_2$L3.DMF. and UO$_2$L4.H$_2$O have been deposited with the Cambridge Crystallographic Data Center as CCDC nos. 650168, 673941, 673940 and 650169, respectively.

TABLE 6

Crystallographic data for uranyl 2-quinoxolinol complexes
1•(UO$_2$)$^{2+}$, 2•(UO$_2$)$^{2+}$, 3•(UO$_2$)$^{2+}$ and 4•(UO$_2$)$^{2+}$

| Compounds | 1•(UO$_2$)$^{2+}$ | 2•(UO$_2$)$^{2+}$ | 3•(UO$_2$)$^{2+}$ | 4•(UO$_2$)$^{2+}$ |
|---|---|---|---|---|
| Empirical formula | C$_{32}$H$_{27}$N$_5$O$_6$U | C$_{32.75}$H$_{28.75}$N$_{5.25}$O$_{8.25}$U | C$_{28}$H$_{26}$N$_5$O$_6$U | C$_{108}$H$_{146}$N$_8$O$_{19}$U$_2$ |
| Fw (g/mol) | 815.62 | 865.89 | 767.58 | 2336.39 |
| Wavelength (Å) | 0.71073 | 0.71073 | 0.71073 | 0.71073 |

TABLE 6-continued

Crystallographic data for uranyl 2-quinoxolinol complexes
1•(UO₂)²⁺, 2•(UO₂)²⁺, 3•(UO₂)²⁺ and 4•(UO₂)²⁺

| Compounds | 1•(UO₂)²⁺ | 2•(UO₂)²⁺ | 3•(UO₂)²⁺ | 4•(UO₂)²⁺ |
|---|---|---|---|---|
| Crystal system | Monoclinic | Monoclinic | Monoclinic | Monoclinic |
| Space group | C2/c | C2/c | C2/c | P2₁/n |
| Z | 8 | 4 | 8 | 4 |
| a (Å) | 33.449(2) | 16.403(2) | 26.074(2) Å | 21.084(2) |
| b (Å) | 7.404(4) | 7.196(4) | 7.291(5) Å | 23.115(2) |
| c (Å) | 28.564(1) | 28.974(3) | 28.868(2) Å | 23.334(2) |
| a (deg) | 90 | 90 | 90 | 90 |
| β (deg) | 124.200(1) | 93.968(3) | 99.572(1) | 107.461(1) |
| g (deg) | 90 | 90 | 90 | 90 |
| V (Å³) | 5851.0(5) | 3412.0(6) | 5411.7(6) | 10848(1) |
| Density calc'd (g/cm³) | 1.852 | 1.686 | 1.882 | 1.431 |
| Abs coeff (mm⁻¹) | 5.603 | 4.814 | 6.051 | 3.050 |
| F(000) | 3152 | 1680 | 2952 | 4744 |
| Cryst size (mm³) | 0.03 × 0.1 × 0.02 | 0.02 × 0.1 × 0.02 | 0.02 × 0.1 × 0.02 | 0.4 × 0.02 × 0.25 |
| Reflns collected | 28742 | 10978 | 1728] | 94464 |
| Indep reflns | 7246 [R$_{(int)}$ = 0.0603] | 7362 [R$_{(int)}$ = 0.0608] | 6501 [R(int) = 0.0496] | 26956 [R$_{(int)}$ = 0.0513] |
| Refinements method | Full-matrix Least Squares on F² | Full-matrix Least Squares on F² | Full-matrix Least Squares on F² | Full-matrix Least Squares on F² |
| GOF of F² | 1.025 | 1.030 | 0.950 | 0.950 |
| Final R indices [I > 2σ(I)] | R₁ = 0.0435 wR₂ = 0.0968 | R₁ = 0.0746 wR₂ = 0.1967 | R₁ = 0.0388 wR₂ = 0.0863 | R₁ = 0.0333 wR₂ = 0.0789 |
| R indices (all data) | R₁ = 0.0668 wR₂ = 0.1051 | R₁ = 0.0746 wR₂ = 0.1967 | R₁ = 0.0684 wR₂ = 0.1036 | R₁ = 0.0517 wR₂ = 0.0848 |
| Largest diff peak and hole (e/Å³) | 2.561 and −0.561 | 2.845 and −2.384 | 2.074 and −1.089 | 1.766 and −0.876 |

Results and Discussion

A detailed description of a synthesis of the ligands has been reported previously in a combinatorial solution method for their synthesis. Using a method based on this earlier synthesis, the fluorescent yellow 2-quinoxolinol salen ligands were obtained as solids in high yield. The ligands were bright yellow in color, stable in air, and soluble in a range of organic solvents. The uranyl complexes have been obtained by combining the appropriate Schiff base with hexa-hydrated $UO_2(OAc)_2$ in a (50:50) solution of dichloromethane and methanol resulting in reddish brown precipitates. Complexes of the ligand $H_2L4$ with transition metals could be obtained in quantitative yields with longer periods of heat or with the addition of base.

Crystals of the $UO_2L1.DMF$ were grown by solvent diffusion of the metal complex in dimethyl formamide with ether. The crystals formed as dark red acicular prisms, conforming to space group C2/c with Z=4. The general coordination motif of uranyl-Schiff base complexes is similar to that seen in the uranyl ($UO_2^{2+}$) salophen (N,N'-disalicylidene-o-phenylenediaminate) complexes having a pentagonal-bipyramidal geometry with the equatorial plane of the uranyl ion coordinated by the two oxo- and two aza-coordination sites of the ligand and the fifth position in that plane occupied by a DMF solvent molecule. This was typical with what was seen in this series of ligands.

The 2-quinoxalinol salen ligands demonstrate a significant twist upon coordination of a metal. This can be seen in the side view of the metal complex (data not shown) This is more pronounced than the 35° seen in the salophen uranyl complex, close to 45' from the coordination plane of the metal ion indicating a strongly bound complex. The average U—N bond distance in the coordination core is 2.55(3) Å, and the average U—O bond distance is 2.25(5) Å. These bond distances are comparable to the salophen uranyl complexes reported previously (data not shown).

A uranyl complex of ligand $UO_2L4.H_2O$ was prepared to demonstrate a second crystallization method using the ligand with improved organic solubility. Such a system might be more suitable in extraction applications. Crystals of the uranyl complex of ligand $UO_2L4.H_2O$ were grown from a solution of the ligand in acetone layered with an aqueous solution of uranyl acetate. This serves to demonstrate the strong coordination capability of the ligand specific to the uranyl ion. Crystals formed as red needles at the interface of the two layers, conforming to space group P2₁/n with Z=4. The asymmetric unit cell contains two independent, seven-coordinate uranyl complexes that differ in the conformation of the ligand substituents. This results in a noticeable difference in the bond distances despite similar environment around uranium center (Table 7). Each complex has one ligand coordinating the metal ion and the fifth coordination site occupied by a water molecule. The U—O bond distances in the "yl" oxygens are typical for uranyl complexes, averaging 1.78(2) Å. The angles of the O—U—O of the uranyl metal ions are near linear at 177.6(10)° for U1 and 178.51(11)° for U2. The average bite angle of the N—U—O angle is 68.9(3)°. The average U—N and U—O bond distances in the coordination core of the two molecules are very similar to that seen before, 2.56(4) Å and 2.25(2) Å, respectively.

Spectroscopy

In the ¹H NMR spectra of the uranyl ($UO_2^{2+}$) complexes, a significant shift in the imine CH=N proton is observed in the uranyl metal complexes (9.6-9.8 ppm for L1-L3, 9.2-93 ppm for L4) as compared to the free ligands (8.9-9.3 ppm). (This difference in L4 is presumably due to the difference in solvation.) This is indicative of the imine nitrogen lone pairs coordinating to the metal center. In a similar fashion, there are three hydroxyl peaks in the ¹H NMR spectra of the free ligands (12.1-13.3 ppm) while in the uranyl ($UO_2^{2+}$) complexes, only one from the quinoxolinol hydroxyl group remains (12.6-12.7 ppm for L1-L3, 12.2 ppm for L4).

In the IR spectra of $UO_2L1.DMF$, $UO_2L2.DMF$, and $UO_2L4.H_2O$ have strong peaks around 1620 cm⁻¹ (free ligands 1.654-1658 cm⁻¹) indicating coordinated imine nitrogens. The uranyl complex of ligand $UO_2L3.DMF$ has a strong vibration at 1603 cm$^{-1}$ (free ligand 1658 cm$^{-1}$) indicating coordinated imine nitrogens. This slight difference between UO$_2$L1.DMF, UO$_2$L2.DMF and UO$_2$L3.DMF may be the result of the absence of the phenyl group in the quinoxolinol backbone. Coordination through the phenolic hydroxyl unit in the salicylaldehyde coordination site can also be shown by the shift in the C—O band for uranyl complexes of ligands UO$_2$L1.DMF and UO$_2$L2.DMF (1203 cm$^{-1}$) as compared to the free ligands (1276 and 1271 cm$^{-1}$, respectively). This is also seen in UO$_2$L3.DMF and UO$_2$L4.H$_2$O, although it is shifted slightly from the other ligands with bands at 1263 cm$^{-1}$ and 1229 cm$^{-1}$ respectively compared to the free ligands (H$_2$L3, 1278 and H$_2$L4, 1261 cm$^{-1}$). Bands around 900 cm$^{-1}$ seen in the uranyl complexes are due to the asymmetric and symmetric UO$_2$ stretching characteristic of linear uranyl ion in the complex.

Broad peaks in free ligands seen around 3400 cm$^{-1}$ (3392-3448 cm$^{-1}$) are indicative of the presence of the hydroxyl groups. These are seen to be absent in the Cu, Co, Ni, and Mn, metal complexes of ligand H$_2$L4, presumably indicating the formation of metal complex with these oxygens. This coordination can be confirmed using the shift in the C—O band of the hydroxy unit in the salen coordination site for the transition metal complexes of ligand H$_2$L4, Co (1256 cm$^{-1}$), Cu (1260 cm$^{-1}$), Ni (1260 cm$^{-1}$) and Mn (1248 cm$^{-1}$), compared to the free ligand, H$_2$L4 (1261 cm$^{-1}$). This is also seen in bands indicative of binding to the lone pairs of the imine nitrogens in the complexes of H$_2$L4 with Co (1614 cm$^{-1}$) and Ni (1616 cm$^{-1}$) compared to the free ligand (1656 cm$^{-1}$).

nm ($\epsilon$=1.7×10$^4$), 304 nm ($\epsilon$=1.6×10$^4$), 360 nm ($\epsilon$=1.3×10$^4$), 385 nm ($\epsilon$=1.3×10$^4$), and 419 inn ($\epsilon$=1.4×10$^4$). The UO$_2$L4.H$_2$O complex in DMF also demonstrated a shift due to the formation of metal complex with maximum absorbances at 295 nm ($\epsilon$=2.5×10$^4$), 375 nm ($\epsilon$=1.6×10$^4$), and 440 nm ($\epsilon$=1.5×10$^4$). This was found to be significantly different than the copper complex of the same ligand in DMF, CuL4: 280 nm ($\epsilon$=3.4×10$^4$), 325 nm ($\epsilon$=2.8×10$^4$), and 454 nm ($\epsilon$=1.5×10$^4$).

TABLE 8

Extinction Coefficients for metal complexes of ligand 4 in dichloromethane.

| Metal Ion (Max Wavelength) | Extinction Coefficient | Metal Ion (Max Wavelength) | Extinction Coefficient |
|---|---|---|---|
| Free ligand (301 nm) | 44500 | Cobalt (437 nm) | 69000 |
| Free ligand (391 nm) | 44100 | Cobalt (322 nm) | 60000 |
| Manganese (510 nm) | 71000 | Copper (458 nm) | 92000 |
| Manganese (372 nm) | 40000 | Copper (330 nm) | 76000 |
| Nickel (452 nm) | 91000 | Copper (286 nm) | 62000 |
| Nickel (388 nm) | 57000 | Uranyl (250 nm) | 34000 |
| Nickel (314 nm) | 48000 | Uranyl (300 nm) | 29000 |
| Nickel (268 nm) | 46000 | Uranyl (379 nm) | 24000 |
|  |  | Uranyl (456 nm) | 17000 |

Because of spectral changes due to the effects of solvent and from ligand to ligand, in order to have a better comparison between uranyl and other potentially competing metals, the transition metal complexes of ligand 4 were prepared along

TABLE 7

Selected interatomic distances (Å) and angles (°) for uranyl complexes UO$_2$L1•DMF, UO$_2$L2•DMF. UO$_2$L3•DMF. and UO$_2$L4•H$_2$O (*UO$_2$L4•H$_2$O uses molecule 1 of the dimolecular unit cell.)

| (UO$_2$)L1•(DMF) | | | | (UO$_2$)L2•(DMF) | | | |
|---|---|---|---|---|---|---|---|
| U1-O1 | 2.241(4) | O1-U1-N1 | 70.57(2) | U1-O3 | 2.233(8) | O3-U1-N1 | 70.1(3) |
| U1-O2 | 2.250(4) | O2-U1-N2 | 69.38(1) | U1-O4 | 2.239(9) | O4-U1-N2 | 71.3(3) |
| U1-O3 | 2.400(4) | O4-U1-O5 | 176.71(2) | U1-O101 | 2.415(9) | O1-U1-O2 | 176.71(2) |
| U1-N1 | 2.521(4) | N1-U1-N2 | 62.83(1) | U1-N1 | 2.571(10) | N1-U1-N2 | 63.6(3) |
| U1-N2 | 2.582(4) | O1-U1-O4 | 93.03(2) | U1-N2 | 2.528(9) | O2-U1-O3 | 93.0(4) |
| U1-O4 | 1.782(4) | O2-U1-O4 | 92.37(2) | U1-O1 | 1.800(9) | O2-U1-O4 | 92.9(4) |
| U1-O5 | 1.796(4) | | | U1-O2 | 1.786(8) | | |
| (UO$_2$)L3•(DMF) | | | | (UO$_2$)L4•(H$_2$O) | | | |
| U1-O1 | 2.252(4) | O1-U1-N1 | 69.96(2) | U1-O3 | 2.254(2) | O3-U1-N1 | 69.23(9) |
| U1-O2 | 2.259(4) | O2-U1-N2 | 69.75(2) | U1-O4 | 2.255(2) | O4-U1-N2 | 68.71(8) |
| U1-O5 | 2.375(5) | O4-U1-O3 | 176.15(2) | U1-O5 | 2.456(2) | O1-U1-O2 | 177.62(10) |
| U1-N1 | 2.549(5) | N1-U1-N2 | 63.28(2) | U1-N1 | 2.551(3) | N1-U1-N2 | 63.54(8) |
| U1-N2 | 2.571(4) | O1-U1-O3 | 87.57(2) | U1-N2 | 2.577(3) | O1-U1-O4 | 91.67(9) |
| U1-O3 | 1.805(4) | O2-U1-O3 | 86.76(2) | U1-O1 | 1.774(2) | O2-U1-O4 | 87.38(10) |
| U1-O4 | 1.782(4) | | | U1-O2 | 1.779(2) | | |

In DMF, ligand H$_2$L1 features two UV peaks at 305 nm ($\epsilon$=32000) and 390 nm. ($\epsilon$=32000). (Data not shown.) The addition of an aqueous solution of HCl causes (3-fold excess) a slight shift to 300 nm and 390 nm with no change seen in the extinction coefficients. Upon the addition of the uranyl ion (UO$_2$$^{2+}$), as a solution of uranyl acetate, the absorption maximum in the UV-Vis spectra demonstrates a shift to 290 nm ($\epsilon$=20000) and 370 nm ($\epsilon$=15000) with an additional peak at 440 nm ($\epsilon$=15000), indicating the formation of uranyl complex. Similar bands have been reported for multidentate hydroxyl-containing uranyl complexes (390 and 450 nm). A similar shift is seen in the spectra in addition to the formation of additional peaks are seen in the uranyl complex UO$_2$L3.DMF (336 nm, 388 nm). The uranyl complex. UO$_2$L3.DMF features additional peaks with maxima at 287 with the uranyl complex in dichloromethane for UV-Vis spectroscopy. The results are shown in Table 8. (See spectra S2-S7 in Supplementary material.) The different metal complexes can be distinguished by their distinct spectra. The differences between the spectra seen in the coordinating solvent DMF and the non-coordinating DCM, are due to the fact that the fifth coordination site in the plane of the uranyl is not filled by solvent, possibly leading to dimers. The cobalt complex has two intense peaks at 322 nm ($\epsilon$=6.0×10$^4$) and 437 nm ($\epsilon$=6.9×10$^4$). The copper complex demonstrated the most intense peaks with the highest extinction coefficients at 330 nm ($\epsilon$=7.6×10$^4$) and 458 nm ($\epsilon$=9.2×10$^4$) and an additional peak at 286 nm ($\epsilon$=6.2×10$^4$). The manganese complex demonstrated two intense peaks at 372 nm ($\epsilon$=4.0×10$^4$) and 510 nm ($\epsilon$=7.1×10$^4$), and so could be distinguished by the unique peak at 510 nm. The nickel complex had four peaks with one very close to the 458 nm of copper at 452 nm ($\in=9.1\times10^4$), but could be distinguished from copper by the additional peaks at 388 nm ($\in=5.7\times10^4$), 314 nm ($\in=4.8\times10^4$) and 268 nm ($\in=4.6\times10^4$). Finally, the uranyl in dichloromethane is unique with two shoulders at 379 nm ($\in=2.4\times10^4$) and 456 nm ($\in=1.7\times10^4$) resulting from the metal complex and peaks at 250 nm ($\in=3.4\times10^4$) and 300 nm ($\in=2.9\times10^4$).

Lanthanide complexes with salen ligands have been described; however, often it has been found the metal is coordinated only to the oxo-groups of the ligand, resulting in a coordination polymer or a sandwich complex. Complexes that can be formed without protection from air or moisture are particularly useful. Without using inert atmosphere methods of preparing air sensitive complexes, these ligands did not demonstrate complex formation with lanthanides either with heating or with the addition of strong base with lanthanide chloride, acetate, or acetoacetonate salts (as judged by UV-Vis or NMR). This is indicative of a certain amount of selectivity for the actinides, based on the high oxophilicity typical of the lanthanides as compared to the actinides which tend to demonstrate more covalent character in their bonding. This is consistent with the high oxophilicity of the lanthanides. Lanthanides greatly prefer hard interactions and an all oxo-coordinating system while actinides will also bind to the nitrogen heteroatoms. Since at the bottom of the periodic table, there are very small differences in ionic radii between metals, separating the lanthanides produced as daughter products during the nuclear fuel cycles is quite a challenge. This difference in their chemistry has been exploited in the development of sulphur or phosphorus containing ligands—such as CMPO (octyl(phenyl)-N,N-diisobutylcarbamoyl methylphosphine oxide)—for the separation and isolation of the actinides. This will require further investigations to elucidate selectivity and determine the potential utility of these ligands in separations applications.

Conclusions

The 2-quinoxolinol Schiff base ligands and their uranyl-complexes have been synthesized and characterized. Crystal structures demonstrate pentagonal bipyramidal geometry around uranium center with the 2 aza and 2 oxo coordinating sites of the ligand perpendicular to the "-yl" oxygens. The remaining coordination site of the metal is occupied by a solvent molecule. A significant twist of the ligand front planar is seen to occur upon coordination of a metal. This results in a change in the $\pi$-orbital overlap of the ligand backbone and contributes to a dramatic change in the ultraviolet-visible spectrum. The use of non-coordinating solvents results in the formation of ligand dimers. The presence of different substituents on the salicylaldehyde moiety incorporated into the ligand backbone affects the solubility of the ligand greatly and also affects the response seen through spectroscopy.

Combining oxo- and imine aza-coordination sites as used here, has been demonstrated to impart, a degree of selectivity for uranyl in particular over lanthanides. At elevated temperature, the ligand has been found to form stable complexes with Cu, Ni, Co, and Mn. Characterization of the transition metal complexes demonstrates that while the uranyl complex is more easily formed, when other metal complexes are formed their spectroscopic signature is characteristic to discriminate between uranyl and transition metals. While possessing a strong signal upon coordination, solubility complicates the determination of selectivity. The change in the UV-Vis spectra of the uranyl complex as compared to transition metal complexes, in particular $Cu^{2+}$, may be exploited in the development of sensors for actinides on surfaces or in contaminated areas.

Additional experiments to develop these ligands as selective metal coordination systems for use in sensors or extraction applications will continue with experiments to quantify selectivity for uranium or actinides over lanthanides and with experiments probing fluorimetric methods to increase sensitivity. The use of fluorimetry would be another way to rule out competition from transition metals in sensing of actinides. These investigations will broaden an understanding of the chemical behavior of the actinides and enable the development of new sensors and sensing materials for improved detection and isolation of actinides from fuel wastes or contaminated environmental sites.

Example 3

References

1. Gorden, A. E. V.; Xu, J.; Raymond, K. N.; Durbin, P. W. *Chem. Rev.* 2003, 103, 4207.
2. Bruno, J.; Ewing, R. C. *Elements* 2007, 2, 343.
3. Durbin, P. W.; Kullgren, B.; Xu, J.; Raymond, K. N. *Radiat. Prof. Dosim.* 1998, 79, 433.
4. Hayton, T. W.; Boncella, J. M.; Scott, B. L.; Batista, E. R. *J. Am. Chem. S.* 2006, 128, 12622.
5. Bray, T. H; Beitz, J. V.; Bean, A. C.; Yu, Y. Q.; Albrecht-Schmitt, T. E. *Inorg. Chem.* 2006, 45, 8251.
6. Schelter, E. J.; Yang, P.; Scott, B. L.; Thompson, J. D.; Martin, R. L.; Hay, P. J.; Morris, D. E.; Kiplinger, J. L. *Inorg. Chem.* 2007, 46, 7477.
7. Takeo, K.; Ikeda, Y. *Inorg. Chem.* 2007, 46, 1550.
8. Graves, C. R.; Yang, P.; Kozimor, S. A.; Vaughn, A. E.; Clark, D. L.; Conradson, S. D.; Schelter, E. J.; Scott, B. L.; Thompson, J. D.; flay, P. J.; Morris, D. E.; Kiplinger, J. L. *J. Am. Chem. Soc.* 2008, 130, 5272.
9. Charushnikova, I. A.; Krot, N. N.; Starikova, Z. A. *Radiochemistry* 2008, 50, 117.
10. Szigethy, G.; Xu, J.; Gorden, A. E. V.; Teat, S. J.; Shuh, D. K.; Raymond, K. N. *Eur. J. Inorg. Chem.* 2008 in press.
11. Bharara, M. S.; Strawbridge, K.; Vilsek, J. Z.; Bray, T. H.; Gorden, A. E. V. *Inorg. Chem.* 2007, 46, 8309.
12. Bharara, M. S.; Tonics, S. A.; Gorden, A. E. V. *Chem. Commun.* 2007, 4006.
13. Bharara, M. S.; Heflin, K. L.; Tonics, S. A.; Strawbridge, K.; Gorden, A. E. V. *Dalton Trans.* 2008, 10, 2966.
14. Nash, K. L.; Choppin, G. R. *Sep. Sci. and Technol.* 1997, 32, 255.
15. Barboso, S.; Carrera, A. G.; Matthews, S. E.; Arnaud-Neu, F.; Bohmer, V.; Dozol, J.-F.; Rouquette, H.; Schwing-Weill, M.-J. *J. Chem. Soc, Perkin Trans.* 2 1999, 719.
16. Mathur, J. N.; Murali, M. S.; Nash, K. L. *Solv. Extr. Ion Exch* 2001, 19, 357.
17. Rogers, R., D.; Kurihara, L. K.; Benning, M. M. *Inorg. Chem.* 1987, 26, 43 46.
18. Hassaballa, H.; Steed, J. W.; Junk, P. C.; Elsegood, M. R. *J. Inorg. Chem.* 1998, 37, 4666.
19. Shinkai, S.; Koreishi, H.; Ueda, K.; Arimura, T.; Manabe, O. *J. Am. Chem. Soc.* 1987, 109, 6371.
20. Salmon, L.; Thuery, P.; Ephritikhine, M. *Eur. J. Inorg. Chem.* 2006, 4289.
21. Salmon, L.; Thuery, P.; Ephritikhine, M. *Chem. Commun.* 2006, 856.
22. Melfi, P. J.; Kim, S. K.; Lee, J. T.; Bolze, F.; Seidel, D.; Lynch, V. M.; Veauthier, J. M.; Gaunt, A. J.; Neu, M. P.; Ou, Z.; Kadish, K. M.; Fukuzumi, S.; Ohkubo, K.; Sessler, J. L. *Inorg, Chem.* 2007, 46, 5143.
23. Sopo, H.; Goljahanpoor, K.; Sillanpaa, R. *Polyhedron* 2007, 26, 3397.

24. Sawicki, M.; Siaugue, J. M.; Jacopin, C.; Moulin, C.; Badly, T.; Durgada, R.; Meunier, S.; Baret, P.; Pierre, J. L.; Taran, F. *Chem. Eur. J.* 2005, 11, 3689.
25. Choppin, G. R. *Sep. Sci. and Technol.* 2006, 41, 1955.
26. Choppin, G. R. *Sol Extra Res & Devt-Jap* 2005, 12, 1.
27. Sessler, J. L.; Melfi, P. J.; Seidel, D.; Gorden, A. E. V.; Ford, D. K.; Palmer, P. D.; Tait, C. D. *Tetrahedron* 2004, 60, 11089.
28. Sessler, J. L.; Melfi, P. J.; Tomat, E.; Callaway, W.; Huggins, M. T.; Gordon, P. L.; Keogh, D. W.; Date, R. W.; Bruce, D. W.; Donnio, B. *J. Alloys Compounds* 2006, 418, 171.
29. Lutfullah; Alam, M. N.; Rahman, N.; Azmi, S, N. H. *J. Haz. Materials* 2008, 155, 261.
30. Murahashi, S.; Naota, T.; Taki, H. *J. Chem. Soc., Chem. Commun.* 1985, 613.
31. Zhang, W.; Loebach, J. L.; Wilson, S. R.; Jacobsen, E. N. *J. Am. Chem. Soc.* 1990, 112, 2801.
32. Wu, M. H.; Hansen, K. B.; Jacobsen, E. N. *Angew. Chem. Int. Ed. Eng.* 1999, 38, 2012.
33. Rudkevich, D. M.; Stauthamer, W. P. R. V.; Verboom, W.; Engbersen, J. F. J.; Harkema, S.; Reinhoudt, D. N. *J. Am. Chem. Soc* 1992, 114, 9671.
34. Van Doom, A. R.; Verboom, W.; Harkema, S.; Reinhoudt, D. N. *Synthesis* 1992, 119.
35. Rudkevich, D. M.; Verboom, W.; Brzozka, Z.; Palys, M. J.; Stauthamer, W. P. R. V.; van Hummel, G. J.; Franken, S. M.; Harkema, S.; Engbersen, J. F. J.; Reinhoudt, D. N. *J. Am. Chem. Sac* 1994, 116, 4341.
36. Vaughn, A. E.; Basalt, D. B.; Barnes, C. L.; Tucker, S. A.;. Duval, P. B. *J. Am. Chem. Soc* 2006, 128, 10656.
37. Wu, X.; Gorden, A. E. V. *J. Comb. Chem.* 2007, 9, 601.
38. Wu, X.; Gorden, A. E. V.; Tonks, S. A.; Vilseck, 3. *J. Org. Chem.* 2007, 72, 8691.
39. Sheldrick, G. M.; Universität Göttingen, 1997.
40. Sheldrick, G. M.; Siemens Analytical X-ray Instruments, Inc: Madison, Wis., 2001.
41. Sheldrick, G. M., SADABS—An empirical absorption correction program; Bruker Analytical X-ray Systems Madison, Wis., 1996.
42. Kannappan, R.; Tanase, S.; Tooke, D. M.; Spek, A. L.; Mutikainen, I.; Turpeinen, U.; Reedijk, J. *Polyhedron* 2004, 23, 2285.
43. Abu-Hussen, A. A. *J. Coord. Chem.* 2006, 59, 157.
44. Casellato, U.; Tamburini, S.; Tomasin, P.; Vigato, P. A. *Inorg. Chim. Acta* 2002, 341, 118.
45. Rao, P. V.; Rao, C. P.; Sreedhara, A.; Wegelius, E. K.; Rissanen, K.; Kolehmainen, E. *J. Chem. Soc., Dalton Trans.* 2000, 1213.
46. Chen, H.; Cronin, J. A.; Archer, R. A. *Macromolecules* 1994, 27, 2174.
47. Wong, W.-K.; Yang, X.; Jones, R. A.; Rivers, J. H.; Lynch, V.; Lo, W.-K.; Xiao, D.; Oye, M. M.; Holmes, A. L. *Inorg. Chem.* 2006, 45, 4340.
48. Diamond, R. M.; Street Jr., K.; Seaborg, G. T. *J. Am. Chem. Soc.* 1954, 76, 1461.
49. Matloka, K.; Sah, A. K.; Peters, M. W.; Srinivasan, P.; Gelis, A. V.; Regalbuto, M.; Scott, M. J. *Inorg. Chem.* 2007, 46, 10549.

Example 4

Reference is made to Wu et al., "One-Pot Metal Templated Synthesis for the Preparation of 2-Quinoxalinol Salen Metal Complexes," Polyhedron, Volume 28, Issue 2, 3 Feb. 2009, Pages 360-362, the content of which is incorporated herein by reference in its entirety.

Abstract

Metal complexes of 2-quinoxalinol salen (salqu) ligands can be prepared in a one-pot metal templated synthesis resulting in significantly enhanced yields than if the ligand were prepared and isolated prior to introducing the metal for complexation. Using this method, 12 salqu metal complexes have been prepared and characterized from +2 metal ions.

One-pot multicomponent syntheses have received increasing attention of late, because they not only address fundamental principles of synthetic efficiency and reaction design, but they also expand the possibilities for extending one-pot reactions into combinatorial and solid-phase methods. This presents a new way of thinking about "greener" chemistry by allowing for the reduction of synthetic steps, purification solvents, and wastes. A one-pot metal templated strategy for the preparation of metal complexes for use in applications offers the distinct advantages of reduced environmental impacts and easier procedures for workup.

Salen or salph complexes have been used widely in applications for everything from catalysts to molecular recognition. For example, salen Cu, Mn, or Ru complexes have been used as catalysts in the catalytic oxidation of secondary amines, as the basis for enantioselective catalysts, and as catalysts for ring-opening metathesis. Uranyl ($UO_2^{2+}$) salophen complexes have been used in molecular recognition studies. In addition, salen Mn complexes can act as catalytic scavengers of hydrogen peroxide and have been demonstrated to have a degree of cytoprotectivity.

Symmetric and asymmetric 2-quinoxolinol salen ligands (abbreviated salqu, e.g. 3) have been synthesized for use in catalysis using solution phase and combinatorial strategies. A disadvantage of this reaction scheme was an extended reaction time required to obtain the optimal yields. Metal complexes of this series of ligands were then prepared by a standard proton transfer procedure. Because applications in solid phase extraction and catalysts of salqu metal complexes have been discovered, it was thought that it would to be advantageous to find a more efficient, economical method to prepare salqu metal complexes. Here, a one-pot synthetic method based on a metal template synthesis to access salqu metal complexes will be introduced. With this method, 12 salqu metal complexes have been synthesized from diamino-2-quinoxalinol (1, Scheme 7) in significantly higher yields in a shorter time than when the ligand is isolated and purified prior to complexation.

Scheme 7. Method for a one-pot synthesis of salqu metal complexes.

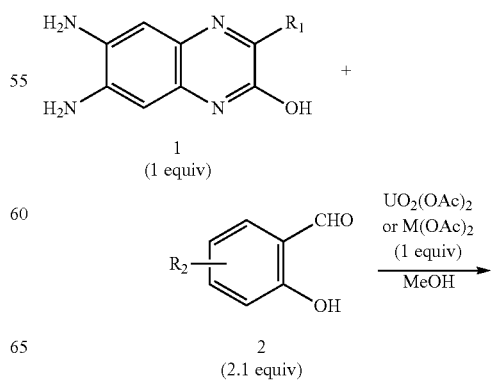

-continued

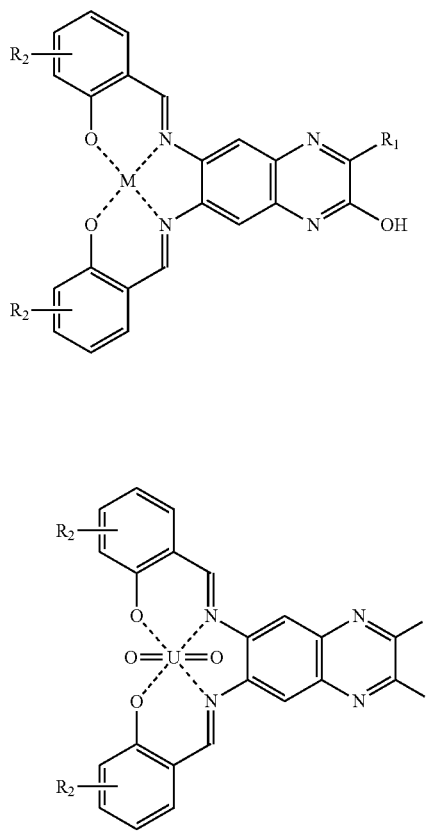

3

Previously, to prepare the salqu metal complexes, two steps were required. The first being the preparation of salqu ligands followed by preparation of the salqu metal complex. In the synthesis of symmetric salqu ligands, the final optimized conditions required that the diamino-2-quinoxalinol intermediate 1 be reacted with 10 equivalents of the desired salicylaldehyde derivatives (2) at reflux temperature in methanol for 48 hours. The ligand must then be isolated prior to the addition of the metal to prepare the metal complex, resulting in yields around 60.0%. Metal complexes are then prepared from a reaction of the salqu ligand (3) with 1.2 equivalents of the desired metal acetate at reflux temperature in either DMF or DCM with MeOH reacted for 2-12 hours. The final yields for this step are around 85.0%, resulting in an overall yield for both reactions close to 50%.

Using a metal templating strategy for a one-pot synthetic method, the diamino-2-quinoxalinol intermediate 1 was reacted with only 2.1 equivalents of the salicylaldehyde derivative (2) and 1.1 equivalents of metal acetate were added directly to the reaction mixture. This also does not require a mixed solvent system, and only methanol was used. The mixture was then heated to reflux temperature and allowed to react for 6 hours. After the reaction was determined to be complete, a large quantity of red or black solid was found to precipitate from solution. The precipitates were filtered and washed with ethanol for 5 times. The solids were dried to obtain salqu metal complexes with purity greater than 95% (Purity was identified by NMR and TLC.) Yields were found to range from 60-85%. The results are listed in Table 9.

TABLE 9

Salqu metal complexes synthesized using a one-pot metal templated method.

| | $[M]^{2+}$ | $R_1$ | $R_2$ | Yield |
|---|---|---|---|---|
| 3a | $Cu^{2+}$ | benzyl | 3,5-di-tert-butyl | 72.8 |
| 3b | $Cu^{2+}$ | benzyl | H | 80.0 |
| 3c | $Mn^{2+}$ | benzyl | 3,5-di-tert-butyl | 76.5 |
| 3d | $Co^{2+}$ | benzyl | 3,5-di-tert-butyl | 69.4 |
| 3e | $Ni^{2+}$ | benzyl | 3,5-di-tert-butyl | 62.7 |
| 3f | $UO_2^{2+}$ | benzyl | 3-OH | 84.5 |
| 3g | $UO_2^{2+}$ | benzyl | 3,5-di-tert-butyl | 62.0 |
| 3h | $UO_2^{2+}$ | benzyl | H | 61.2 |
| 3i | $UO_2^{2+}$ | isopropyl | 3,5-di-tert-butyl | 65.3 |
| 3j | $UO_2^{2+}$ | isopropyl | H | 63.4 |
| 3k | $UO_2^{2+}$ | sec-butyl | H | 67.0 |
| 3l | $UO_2^{2+}$ | -CH2CH2-S-CH3 | H | 69.8 |

The IR spectral results are indicative of metal complexation. Broad peaks in free ligands seen around 3400 cm$^{-1}$ (3400-3448 cm$^{-1}$) are indicative of the presence of the hydroxyl groups on the free ligand. These broad signals are seen to be absent in the Cu, Mn, Co, Ni, and $UO_2$ metal complexes indicating the formation of the metal complex with these oxygens. Coordination through the phenolic hydroxyl unit in the salicylaldehyde coordination site can also be shown a shift in the C—O band for the metal complexes between 1199-1213 cm$^{-1}$ as compared to the sharp peak in the free ligands (1263-1276 cm$^{-1}$). (3j was lower 1146 cm$^{-1}$ although there was not a peak seen as in the range characteristic of the C—O stretch in the starting material.)

The spectra of the free ligands have peaks around 1654-1658 cm$^{-1}$ for the carbon-nitrogen imine stretch. This was seen to shift to 1599-1620 cm$^{-1}$ (3f-3l) for the uranyl complexes and was indicative of coordinated imine nitrogens. This peak was seen at 1616-1614 cm$^{-1}$ in the Ni$^{2+}$ and Co$^{2+}$ complexes, and in the Cu$^{2+}$ complex (3b) but was not as well defined in the Mn$^{2+}$ or in the Cu$^{2+}$ (3a) in which the metal may not be strongly coordinating to the imines. Bands around 900 cm$^{-1}$ (897-903 cm$^{-1}$) seen in the uranyl complexes (3f-3l) are due to the asymmetric and symmetric UO$_2$ stretching characteristic of linear uranyl ion in the complex.

In the $^1$H NMR spectra of the uranyl (UO$_2^{2+}$) complexes, a significant shift in the imine CH=N proton was observed in the uranyl metal complexes (9.5-9.8 ppm for 3f-3l) as compared to the free ligands (8.9-9.3 ppm). This was indicative of the imine nitrogen lone pairs coordinating to the metal center. In a similar fashion, there are three hydroxyl peaks in the $^1$H NMR spectra of the free ligands (12.1-13.3 ppm) while in the uranyl (UO$_2^{2+}$) complexes, only one from the quinoxolinol hydroxyl group remains (12.6-12.7 ppm for 3f, 3h, and 3j-3l, 12.2-12.3 ppm for 3g, 3i).

The advantages of the one-pot synthetic method for preparing salqu metal complexes are the shortened reaction time from more than 2 days to 6 hours and improved final yields from less than 50.0% to over 60-85%. This permits optimization of the procedure in order to conserve the amounts of the salicylaldehyde derivatives (2) used while avoiding using the more troublesome solvent DMF. This method could be incorporated into a combinatorial method for synthesis of these complexes because of its relative simplicity and high yield.

In conclusion, a one-pot methodology based on a metal templating synthesis using +2 metal ions to more easily and rapidly prepare salqu metal complexes is an efficient method to prepare these metal complexes. With this method, several salqu metal complexes have been synthesized and identified. This will be a more convenient synthetic method in exploring the use of such metal complexes. In the future, a new salqu metal complex library will be prepared in this way.

General Procedure and Data

All amino acid methyl esters, DFDNB, HCl (37%) and aldehydes were purchased from Acros Organics Co. Ammonium hydroxide (5.0 N), palladium on carbon (wet, 5%) were purchased from Sigma-Aldrich Co. Starting materials were used as received. All organic solvents were purchased from Thermo Fisher Scientific Co, and were used directly for synthesis. $^1$H and $^{13}$C NMR spectra were recorded on Bruker AC 250 spectrometer (operated at 250 and 62.5 MHz, respectively) or Bruker AV 400 spectrometer (operated at 400 and 100 MHz, respectively). Chemical shifts are reported as δ values (ppm). The solvents used are indicted in the experimental details. Electrospray ionization mass spectrometry was performed on a Micromass QTOF mass spectrometer (Waters Corp, Milford Mass.). Direct probe samples were on a VG-70S mass spectrometer (Waters Corp, Milford Mass.). Reaction progress was monitored by thin-layer chromatography (TLC) using 0.25 mm Whatman Aluminum silica gel 60-F254 precoated plates with visualization by irradiation with a Mineralight UVGL-25 lamp. IR spectroscopic data was collected using a Shimsdzu™ Inc. IR, Prestige-21 Fourier Transform Infrared Spectrophotometer and KBr solid samples.

To a 5 ml methanol solution of intermediate 1 (0.05 mmol), 2.1 equivalents of the desired salicylaldehyde derivatives (e.g., 2 0.105 mmol) and 1.1 equivalent of metal acetate (0.055 mmol) were added. The mixture was heated to reflux temperature with stirring and allowed to react for 6 hours. At this time, a dark red or black solid precipitates out, indicating the completion of the reaction. The precipitates were filtered from the reaction solution. They were then washed with ethanol five times. Finally, the solids were dried under high vacuum.

3a IR: 3067, 2955, 1661, 1586, 1528, 1491, 1416, 1377, 1260, 1209, 1173, 1130 cm$^{-1}$. MS: 760.0 (M+H); HRMS: found (760.3413); calc (760.3422).

3b IR: 3510, 3392, 1655, 1605, 1587, 1560, 1526, 1499, 1442, 1382, 1331, 1200, 1178, 1151. cm$^{-1}$. MS: 536.1 (M+H); HRMS: found (536.0912); calc (536.0909).

3c IR: 3385, 3248, 3208, 2955, 2911, 1670, 1582, 1532, 1462, 1416, 1317, 1248, 1177, 1130 cm$^{-1}$. MS: 751.3 (M+H); HRMS: found (751.3420); calc (751.3429).

3d IR: 3066, 2957, 1665, 1614, 1572, 1524, 1501, 1462, 1410, 1256, 1180, 1128 cm$^{-1}$. MS: 755.3 (M+H); HRMS: found (755.3369); calc (755.3372), 3e IR: 3067, 2955, 2870, 1665, 1616, 1584, 1533, 1598, 1464, 1414, 1379, 1260, 1182, 1130 cm$^{-1}$. MS: 755.3 (M+H); HRMS: found (755.3461); calc 755.3471.

3f $^1$H-NMR (400 MHz DMSO-d$^6$): δ 4.22 (s, 2H), 6.54-8.67 (m, 13H), 9.55 (s, 1H), 9.71 (s, 1H), 11.77 (bs, 1H), 11.82 (bs, 1H), 12.69 (bs, 1H). $^{13}$C-NMR: 160.2, 159.4, 155.0, 137.8, 132.8, 132.0, 129.7, 128.9, 126.9, 126.3, 124.1, 124.0, 123.9, 119.5, 117.1, 106.3, 42.0. IR: 3397, 3337, 2965, 1657, 1620, 1582, 1545, 1491, 1445, 1204, 903 cm$^{-1}$. MS: 816.2 (M+H+CH$_3$CN); HRMS: found (816.2178); cal (816.2183).

3g $^1$H-NMR (400 MHz DMSO-d6): δ 1.19 (s, 18H), 1.64 (s, 18H), 4.11 (s, 2H), 7.09-7.63 (m, 10H), 7.70 (s, 1H), 9.19 (s, 1H), 932 (s, 1H), 12.18 (bs, 1H), $^{13}$C-NMR: 173.3, 173.0, 171.2, 165.1, 153.8, 148.8, 144.6, 144.3, 143.5, 142.0, 137.1, 135.9, 134.2, 133.1, 131.3, 128.9, 123.3, 110.6, 42.0, 40.3, 38.6, 36.3, 35.1. IR: 3433, 2957, 1655, 1620, 1383, 1283, 1229, 1153, 937, 760 cm$^{-1}$. MS: 967.4 (M+H); HRMS found (967.4514); calc (967.4524).

3h $^1$H NMR (400 MHz DMSO-d$^6$): δ4.20 (s, 2H), 6.73-6.77 (t, 2H), 7.00-7.04 (t, 2H), 7.24-7.88 (m, 10H), 8.12 (s, 1H), 9.60 (s, 1H), 9.76 (s, 1H), 12.67 (bs, 1H). $^{13}$C-NMR: 170.8, 170.2, 168.0, 167.3, 161.3, 155.0, 148.9, 143.6, 137.8, 137.3, 136.5, 132.8, 129.7, 128.9, 126.9, 124.8, 121.4, 121.0, 119.5, 117.4, 106.3, 42.3. IR: 3397, 3337, 2965, 1657, 1620, 1582, 1545, 1491, 1445, 1204, 1144, 1040 cm$^{-1}$. MS: 784.0 (M+H+CH3CN); HRMS: found (784.2280); calc (784.2285).

3i $^1$H-NMR (400 MHz DMSO-d$^6$): δ 1.22 (d, 6H), 1.26 (s, 18H), 1.69 (s, 18H), 3.50 (m, 1H), 7.26-7.80 (m, 6H), 9.30 (s, 1H), 9.46 (s, 1H), 12.28 (bs, 1H). $^{13}$C-NMR: 173.3, 172.6, 153.4, 148.6, 144.6, 144.4, 143.3, 136.8, 135.7, 134.4, 128.9, 123.3, 110.4, 40.4, 38.6, 36.4, 35.1, 25.1, IR: 3444, 2958, 1710, 1666, 1587, 1423, 1371 1224, 898 cm$^{-1}$. MS: 919.2 (M+H); HRMS: found (919.4514); calc (919.4524).

3j $^1$H-NMR (400 MHz DMSO-d$^6$): δ 1.28 (d, 6H), 3.56 (m, 1H), 6.74-8.17 (m, 10H), 9.61 (s, 1H), 9.81 (s, 1H), 12.58 (bs, 1H). $^{13}$C-NMR: 170.8, 170.2, 170.0, 167.9, 166.6, 154.6, 148.3, 143.5, 137.2, 136.5, 132.5, 131.9, 124.8, 124.6, 121.4, 121.0, 119.4, 117.4, 106.2, 30.5, 20.6. IR: 3406, 2966, 1654, 1602, 1539, 1463, 1400, 1384, 1145, 898 cm$^{-1}$. MS: 736.2 (M+H); HRMS: found (736.2280); calc (736.2285).

3k $^1$H-NMR (400 MHz DMSO-d$^6$): δ 1.00 (d, 6H), 228 (m, 1H), 2.74 (d, 2H), 6.75 (t, 2H), 7.03 (t, 2H), 7.44 (s, 1H), 7.65 (m, 2H), 7.87 (t, 2H), 8.19 (s, 1H), 9.61 (s, 1H), 9.78 (s, 1H), 12.54 (bs, 1H). $^{13}$C-NMR: 170.8, 1702, 162.3, 155.2, 148.3, 143.4, 137.2, 136.5, 132.6, 132.0, 124.8, 124.6, 121.4, 121.1, 119.3, 117.4, 106.2, 42.1, 26.8, 23.1. IR: 3395, 2927, 1637, 1606, 1539, 1463, 1435, 1383, 1282, 937 cm$^{-1}$. MS: 709.2 (M+H); HRMS: found (709.2167); calc (709.2176).

3l $^1$H-NMR (400 MHz DMSO-d$^6$): δ 2.15 (s, 3H), 2.96 (t, 2H), 3.16 (t, 2H), 6.75 (t, 2H), 7.03 (t, 2H), 7.46 (s, 1H), 7.66 (m, 2H), 7.87 (t, 2H), 8.19 (s, 1H), 9.62 (s, 1H), 9.78 (s, 1H), 12.64 (bs, 1H). $^{13}$C-NMR: 170.8, 170.2, 168.0, 167.2, 161.1, 155.0, 148.5, 143.5, 137.3, 136.5, 132.7, 131.2, 124.7, 121.4, 121.0, 119.4, 117.5, 106.3, 33.3, 30.5, 15.2. IR: 3395, 2927, 1637, 1606, 1539, 1463, 1435, 1383, 1282, 937 cm$^{-1}$. IR: 3408, 1655, 1637, 1601, 1583, 1537, 1464, 1440, 1382, 1300, 1199, 1150, 897, 760 cm$^{-1}$. MS: 768.2 (M+H); HRMS: found (768.2013); calc (768.2006).

Example 4

References

1. Ugi, I.; Domling, A.; Werner, B. *J. Heterocycl. Chem.* 2000, 37, 647.
2. Posner, G. H. *Chem. Rev.* 1986, 86, 831.
3. Weber, L.; Illgen, K.; Almstetter, M. *Synlett* 1999, 366.
4. Kobayashi, S. *Chem. Soc. Rev.* 1999, 28, 1.
5. Murahashi, S.; Naota T.; Taki, H. *J. Chem. Soc., Chem. Commun.,* 1985, 613.
6. Zhang, W.; Loebach, J. L.; Wilson, S. R.; Jacobsen, E. N. *J. Am. Chem. Soc.,* 1990, 112, 2801.
7. Wu, M. H.; Hansen K. B.; Jacobsen, E. N. *Angew. Chem., Int. Ed.* 1999, 38, 2012.
8. Reinoso-Garcia, M. M.; Dijkman, A.; Verboom, W.; Reinhoudt, D. N.; Malinowska, E.; Wojciechowska, D.; Pietrzak M.; Selucky, P. *Eur. J. Org. Chem.* 2005, 2131.
9. Van Axel Castelli, V.; Dalla Cort, A.; Mandolini, L.; Pinto, V.; Reinhoudt, D. N.; Ribaudo, F.; Sanna, C.; Schiaffino, L.; Snellinkruel, B. H. M. *Supramolecular Chem.* 2002, 14, 211.
10. Rudkevich, D. M.; Stauthamer, W. P. R. V.; Verboom, W.; Engbersen, J. F. J.; Harketna, S.; Reinhoudt, D. N. *J. Am. Chem. Sac,* 1992, 114, 9671.
11. Doctrow, S. R.; Huffman, K.; Marcus, C. B.; Tocco, G.; Malfroy, E.; Adinolfi, C. A.; Kruk, H.; Baker, K.; Lazarowych, N.; Mascarenhas, J.; Malfroy, B., *J. Med. Chem.* 2002, 45, 4549
12. Wu, X.; Gorden, A. E. V. *J. Comb. Chem.* 2007, 9, 601.
13. Wu, X.; Gorden, A. E. V.; Tonics, S. A.; Vilseck, J. Z. *J. Org. Chem.* 2007, 72, 8691,
14. Wu, X.; Bray, T. H.; Bharara, M.; Tate, B. K.; Gorden, A. E. V. *Inorg. Chim. Acta.* 2008, in press.
15. Wu, X.; Gorden, A. E. V. *Tetrahedron Lett.* 2008, 49, 5200.
16. Wu, X.; Gorden, A. E. V. *Eur. J. Org. Chem. accepted*
17. Casellato, U.; Tamburini, S.; Tomasin, P.; Vigato, P. A. *Inorg. Chim. Acta.* 2002, 341, 118.
18. Abu-Hussen, A. A. *J. Coord. Chem.* 2006, 59, 157.

Example 5

Wu et al., "2-Quinoxalinol Salen Ligands Incorporated Into Functionalized Resins for Selective Solid-Phase Extraction of Copper (II)," Tetrahedron Letters, Volume 49, Issue 35, 25 Aug. 2008, Pages 5200-5203, the content of which is incorporated herein by reference in its entirety.

Abstract

In exploring selective extraction systems for use in environmental remediation or in metal scavenging agents for use in combinatorial chemistry, a novel reagent for the selective extraction of copper (H) has been developed. 2-Quinoxalinol salen ligands supported on an aminomethyl-polystyrene resin has been shown to efficiently and selectively extract copper (II) ions from organic solvents within 30 minutes under a variety of experimental conditions. Mild reducing conditions allow for metal ion recovery.

Solid-phase extraction (SPE) technologies are being used in a wide number of areas including environmental chemistry, medicinal chemistry, combinatorial chemistry, agriculture, and food science. This technology has been used in environmental applications to monitor or extract toxic heavy metal cations such as $Hg^{2+}$, $Pb^{2+}$, $As^{3+}$, etc. Others have applied solid phase micro-extraction (SPME) techniques to analyze biological fluids in diagnostic medicine. In food science, SPE technologies are used extensively in food analysis and quality control. Currently the most common application of SPE technology currently in use is in the identification of drug components, one promising area of SPE technology not as widely investigated is as a scavenging agent to remove excess catalysts or metal ions used in synthetic methods or combinatorial chemistry.

Copper salts are often applied as catalysts in a variety of organic synthetic procedures. An overabundance of copper in the environment is of concern due to possible harmful effects to agriculture, fish, or wildlife. SPE technology for the selective recovery of copper has not previously been described in the literature. Such technology has considerable potential and would allow many catalytic or coupling reactions commonly used in the synthetic laboratory to be more accessible for use in combinatorial processes or in industrial applications where excess or trace metal ions are likely to complicate subsequent reactions. In addition, because of the high cost of copper reagents, this would create a more efficient and more readily recyclable system thereby limiting the need for costly copper reagents.

In previous research, both symmetric and asymmetric 2-quinoxalinol salen ligands were prepared. (See structure 1 as an example). It has been found that these ligands can coordinate +2 metal cations. Detailed here are methods of preparing solid phase reagents comprising 2-quinoxalinol salen ligands and their application in the selective extraction and recovery of copper cations.

Polystyrene (PS) aminomethyl resin was selected as solid carrier, because this resin can swell in many organic solvents.

Glutaric anhydride was selected as linker between solid carrier and 2-quinoxalinol salen ligand. The isopropyl-2-quinoxalinol salen ligand (1) was selected as the coordination ligand, both because the 5'-hydroxyl group on the outer portion of the salen is a convenient site for incorporating the resin, and because its yield is the highest of the symmetric library. Presented in Scheme 8 is the optimized method for the synthesis of solid reagents PLG1 or PLG2.

Scheme 8. Reaction route for solid reagents PLG1 and PLG2.

a.

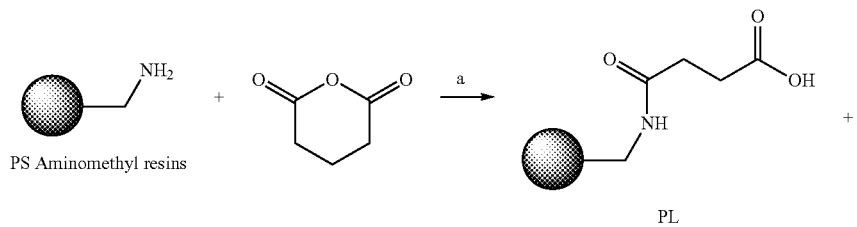

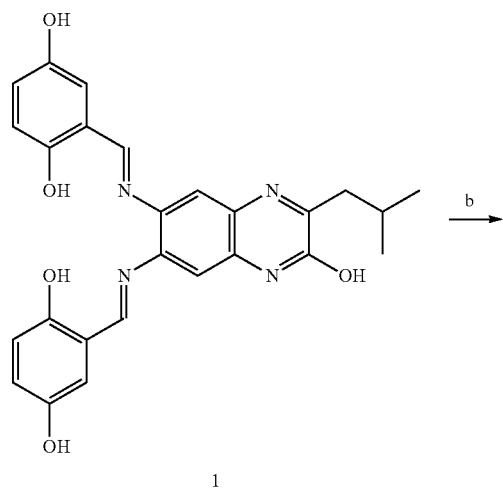

b.

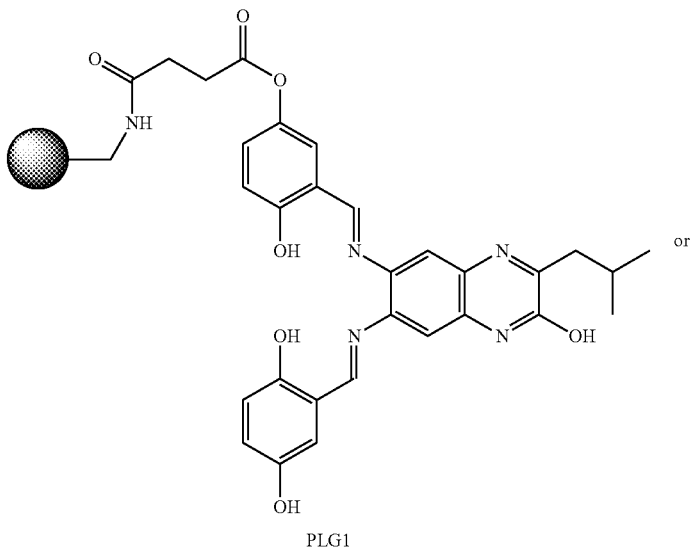

-continued

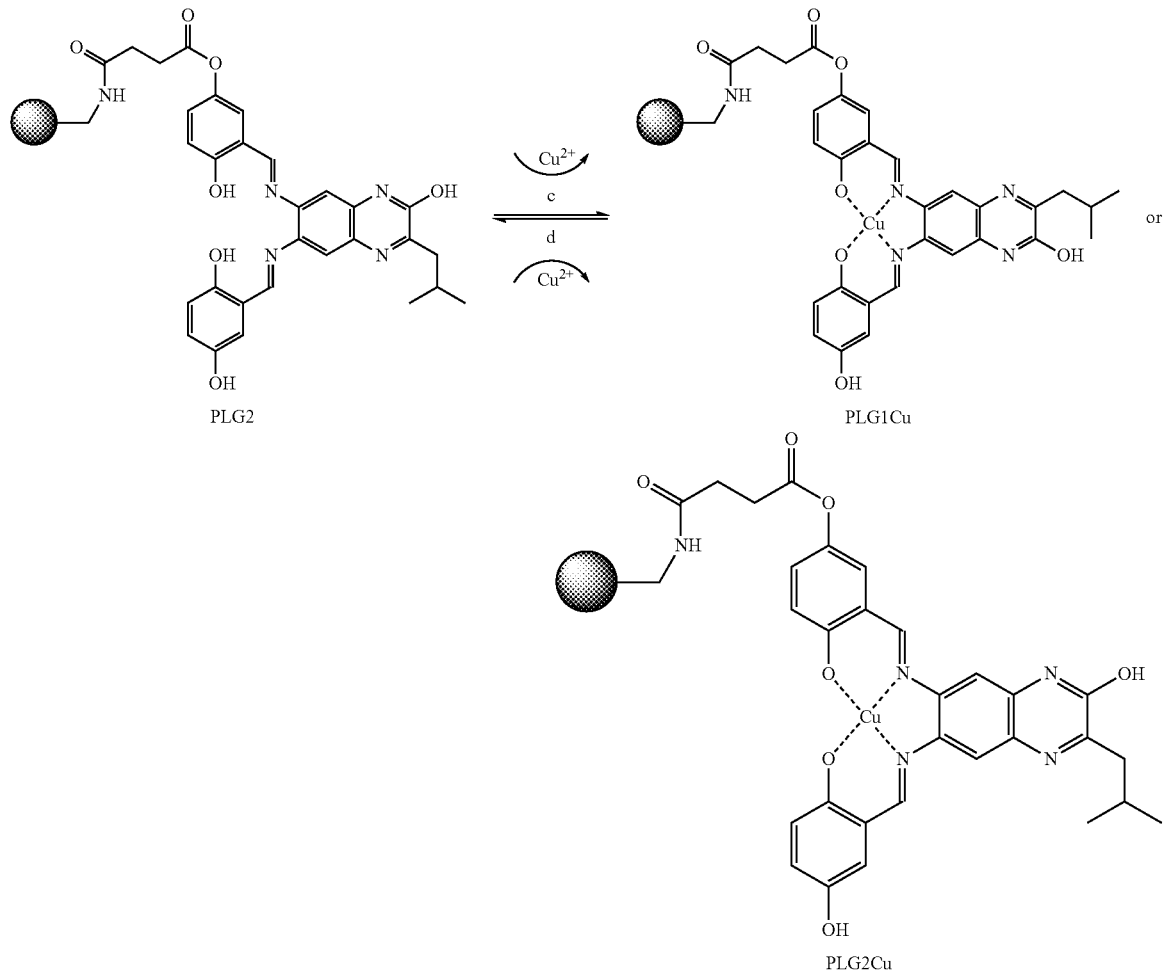

Reactions conditions: a. 5 equiv Glutarcanhydride, DCM, r.t., 24 hr. b. 2.2 equiv DMAP, 2.2 equiv DIC, DMF, r.t., 72 hr. c. $Cu^{2+}$, DCM, MeOH, r.t., 30 min. d. NaBH(OAc)$_3$, DCM, AcOH, r.t., 4 hr.

Different molar ratios and various solvents were investigated to optimize the acylation of the amino group onto the (PS) aminomethyl resin. Finally, a molar ratio of glutaric anhydride to (PS) aminomethyl resin 5:1 using dichloromethane as solvent at room temperature for 24 hours was found to be the optimum conditions for acylation of the amino group. After acylation was completed, the resin was washed with DCM, DMF, and MeOH, three times each. The loaded resin PL can be further acylated with 1.5 equivalent of ligand 1 by using 2.2 equivalents of 4-dimethyl-aminopyridine (DMAP) and 2.2 equivalents of N,N'-diisopropyl-carbodiimide (DIC) in distilled, dry DMF at room temperature for three days. Extending the reaction time does not increase loading. Without DMAP, the loading was very low. If wet DMF was used, the loading capability was decreased, because DIC can be decomposed easily by moisture.

There are three potential binding sites (the 2, 2' and 5' positions) for the carboxylic acid linker to attach to ligand 1. Positions 2 and 2' cannot react with the carboxylic acid moiety due to reactive inertia of 2 position and bonding also limits the reactivity of the hydroxyl group on the 2' position. Reaction with hydroxyl groups in the two 5' positions, results in two possible products (i.e., PLG1 and PLG2). They have the same coordination capability to bind +2 valence metal cations because the mien coordination cavity is not affected by their position. By this procedure, PL was obtained with 100.0% loading by ninhydrin test and PLG1 and PLG2 were obtained with 60.0-65.0% loading, as determined by mass. Identification of resins PLG1 and PLG2 was made by comparing the major peaks of an IR spectra of ligand 1 (3381.2, 1658.8, 1622.3, 1577.8, 1489.1, 1278.8 cm$^{-1}$).

Figure 3:
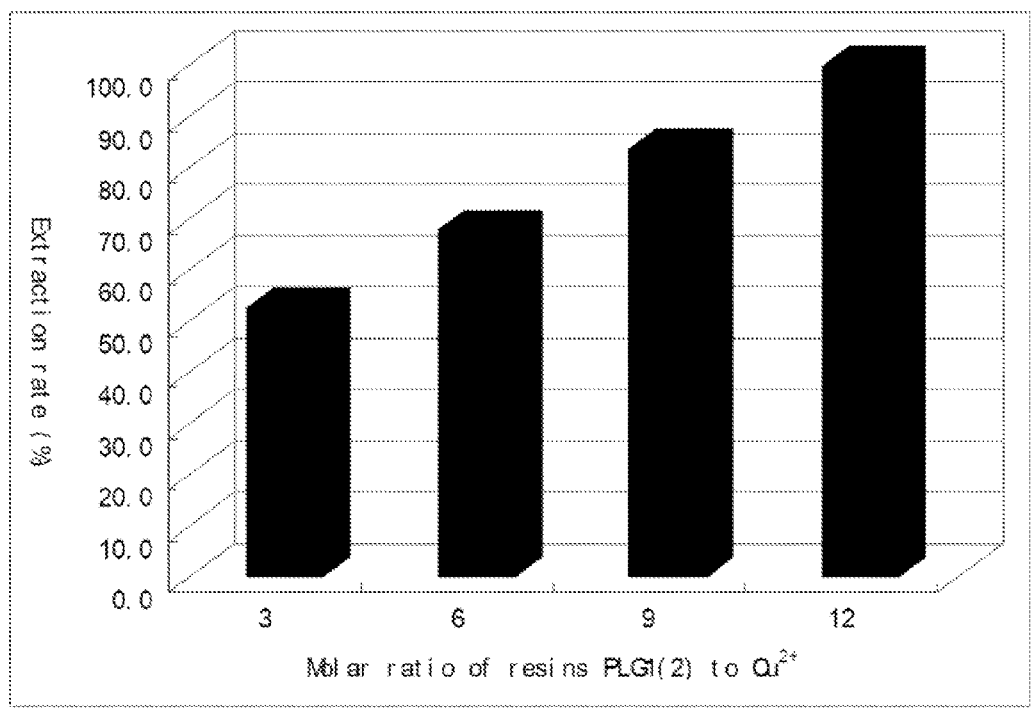
FIG. 3. is a bar graph of $Cu^{2+}$ extraction indicating the different molar ratios of PLG1(2) resin to $Cu^{2+}$ extracted quantified using atomic absorption.
Figure 4:
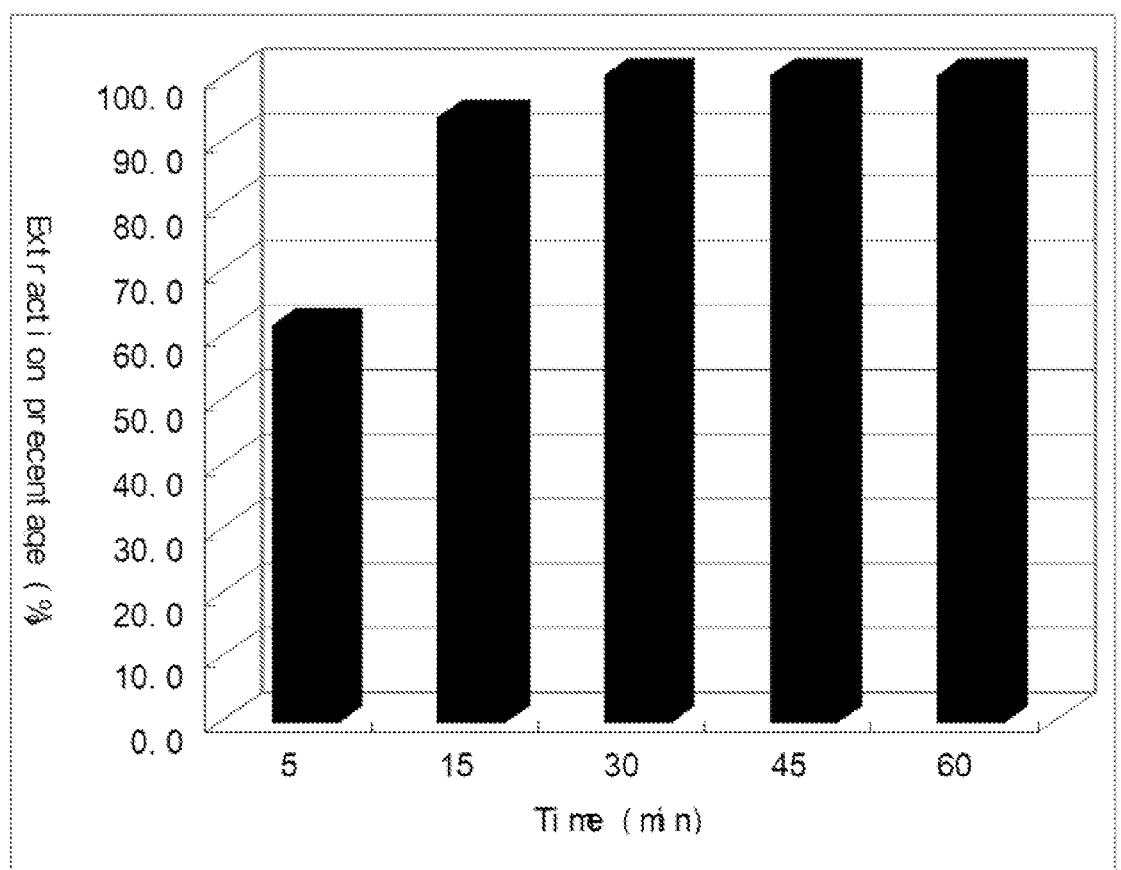
FIG. 4. is a bar graph of $Cu^{2+}$ extraction with PLG1(2) resin with respect to agitation time quantified using atomic absorption.

With this solid ligand functionalized reagent in hand, extraction studies were run in several different solvent combinations: DMF, DMF/MeOH, MeOH, THF/MeOH, steric hindrance of the 2' position. Hydrogen DCM/MeOH and DCM/EtOH. Finally, it was found that DCM/MeOH was the best combination for extraction, because the DCM can best swell the PS resins while MeOH still readily dissolves the metal salts. Metal salts of $Cu^{2+}$, $Mn^{2+}$, and $Ni^{2+}$ were used in extraction studies. Solutions containing these metal cations were prepared using copper acetate, manganese acetate, and nickel nitrate salts in a 50:50 solution of DCM/MeOH. To determine extraction capability, 3 ml of a prepared solution of $2\times10^{-4}$ mol/L $Cu^{2+}$ was mixed with 5 mg, 10 mg, 15 mg, 20 mg prepared PLG1(2) (The molar ratio of $Cu^{2+}$ to PLG1(2) was 1:3, 1:6, 1:9, 1:12.) respectively at room temperature with stirring for 40 min. The extraction results for $Cu^{2+}$ metal are shown in FIG. 3. It was found that 20 mg PLG1 and PLG2 resins may completely extract 3 ml $Cu^{2+}$ $2\times10^{-4}$ mol/L solution at 40 min. Further optimization of extracting time using 20 mg PLG1 and PLG2 resins with 3 ml $2\times10^{-4}$ mol/L concentration copper cations solution at room temperature (FIG. 4) showed that the shortest time for 100% extraction was 30 min. Complexed resin can be directly filtered off to separate from the organic solvent.

For nickel, 20 mg of prepared PLG1 or PLG2 was mixed with 3 ml of the nickel ($2\times10^{-4}$ mol/L) salt solution at room temperature. After 24 hours, only 30% of nickel was extracted, and after 72 hours, only 45.7% of the nickel was extracted. (The final metal ion concentrations were determined using atomic absorption.) For Mn, the Mn salt solution must be prepared as a $1\times10^{-4}$ mol/L solution, because the detection limit for Mn by atomic absorption using a hollow cathode lamp is limited. A 3 ml $1\times10^{-4}$ mol/L manganese salt solution was extracted at room temperature by 10 mg PLG1 and PLG2 resins for 24 hours. It was found that 63.0% of the manganese was removed by the resin, This lead to a surprising conclusion. The PLG1 and PLG2 resins might selectively extract $Cu^{2+}$ within a short time (30 min). To confirm this, 3 ml $2\times10^{-4}$ mol/L $Cu^{2+}$ and 3 ml $2\times10^{-4}$ mol/L $Ni^{2+}$ solution were combined to prepare a 6 ml $1\times10^{-4}$ mol/L $Cu^{2+}$ and $Ni^{2+}$ mixed solution; 3 ml $2\times10^{-4}$ mol/L $Cu^{2+}$ solution and 3 ml $1\times10^{-4}$ mol/L $Mn^{2+}$ solution were combined to obtain a 6 ml $1\times10^{-4}$ mol/L $Cu^{2+}$ and $5\times10^{-5}$ mol/L $Mn^{2+}$ solution. To these mixed solutions, 20 mg of the prepared PLG1 and PLG2 resin was added at room temperature and allowed to extract for 45 min. After filtering off the PLG1 and PLG2 resins, the extraction solution were analyzed by atomic absorption. It was found that 80.0% of the $Cu^{2+}$ was removed, but only 7.8% $Ni^{2+}$ in the $Cu^{2+}/Ni^{2+}$ solution, and only 22.0% $Mn^{2+}$ was extracted in the $Cu^{2+}/Mn^{2+}$ mixed solutions.

For the recovery of copper from the PLG1Cu and PLG2Cu resins, several different conditions were tried (Scheme 8). Routine cleavage or recovery conditions, DCM with different organic acids including trifluoroacetic acid were not found to release copper ions, nor were strong bases.

Figure 5:
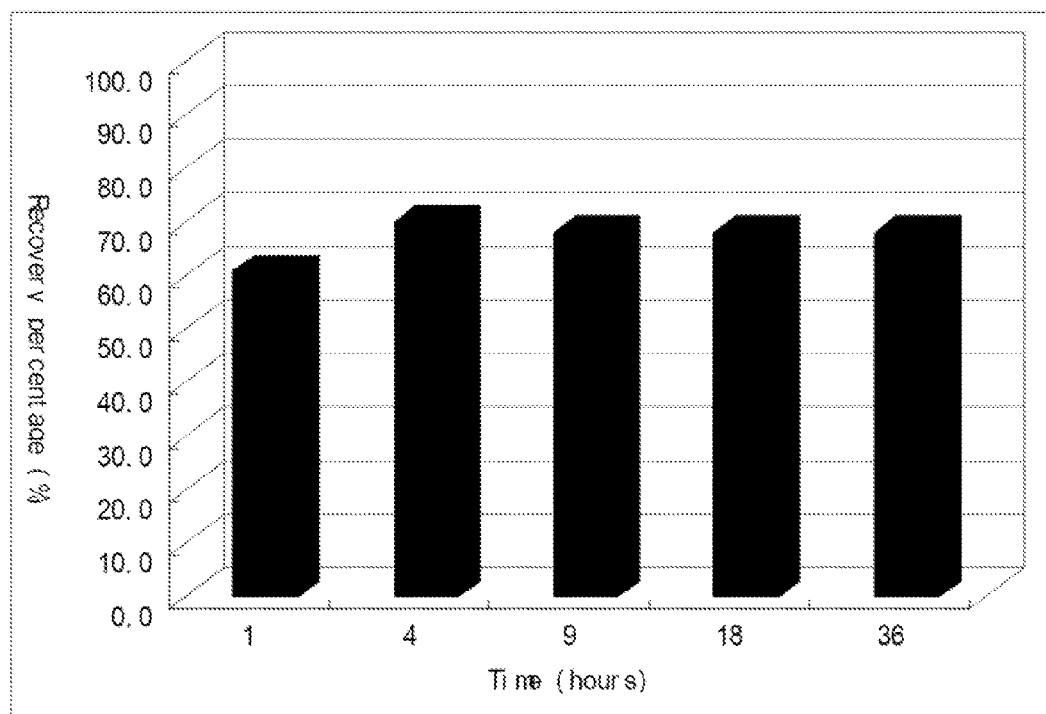
FIG. 5. is a bar graph of $Cu^{2+}$ recovery with PLG1(2) resin versus time quantified using atomic absorption.

Because sodium triacetoxyborohydride can efficiently reduce the imine group (C=N) to amino group (C—N) which coordinates only weakly with the metal, the 20 mg PLG1Cu and PLG2Cu resins were mixed with 3 ml DCM/$CH_3COOH$ (2:1). To this, 10 mg sodium triacetoxyborohydride was added, and the reaction progress was measured over time (FIG. 5). The results show that after 4 hours the maximum amount of $Cu^{2+}$ can be recovered (70.0%). Extending the reaction time or increasing the amount of sodium triacetoxyborohydride does not increase this recovery rate.

To conclude, an optimized synthetic route for resins PLG1 and PLG2 was obtained. This kind of resin can selectively extract copper (II) cation within short time. The copper can then be recovered using reducing conditions from the resin. This has the potential to enable the selective extraction of copper even from a mixture containing other metals. PLG1 and PLG2 resins could also be applied in environmental or materials chemistry to remove copper or in combinatorial chemistry as a metal scavenging agent to remove excess copper. In the future, design new solid reagents to selectively extract other metals or improve on the selectivity or application of this system.

Experimental

All organic solvents were from Sigma-Aldrich Co. and were used directly for synthesis. Metal salts and other reagent for synthesis were from Acros Organics Co. Polystyrene (PS) aminomethyl resin (1% DVB, 0.59 mol/g loading and 100-200 mesh.) was from ChemPep Inc. IR, Prestige-21 Fourier transform infrared spectrophotometer and KBr solid samples. Atomic absorption spectrum (Varian AA240), its software (AA240FS) and hollow cathode lamp (HLC; Ni 232.0 nm, optimum working range: 0.1-20 mg/L; Mn 279.5 nm, optimum working range: 0.02-5 mg/L; Cu 324.8 nm, optimum working range: 0.03-10 mg/L) from Varian, Inc.

Example 5

References

1. Zhao, J.; Han, B.; Dian, Y.; Wang, D. *Anal. Chim. Acta* 2007, 603, 87.
2. Jeanneau, L.; Faure, P.; Jarde, E. *J. Chromatography A.* 2007, 1173, 1.
3. Tokuyama, H.; Iwama, T.; *Langmuir*, ASAP.
4. Vanloot, P.; Branger, C.; Margaillan, A.; Brach-Papa, C.; Boudenne, J. L.; Coulomb, B. *Anal. Bioanal. Chem.* 2007, 389, 1595,
5. Divrikli, U.; Akdogan, A.; Soylak, M.; Elci, L. *J. Haz. Materials* 2007, 149, 331.
6. Cui, Y.; Chang, X.; Zhu, X.; Luo, H.; Hu, Z.; Zou, X.; He, Q. *Microchemical Journal* 2007, 87, 20.
7. Duran, C.; Gundogdu, A.; Bulut, V. N.; Soylak, M.; Elci, L.; Senturk, H. B.; Tufekci, M. *J. Haz. Mat.* 2007, 146, 347.
8. Musteata, M. L.; Musteata, F. M.; Pawliszyn, J. *Anal. Chem.* 2007, 79, 6903.
9. Grigoriadou, D.; Androulaki, A.; Psomiadou, E.; Tsimidou, M. Z. *Food Chem.* 2007, 105, 675.
10. Rodrigues, C. I.; Marta, L.; Maia, R.; Miranda, M.; Ribeirinho, M.; Maguas, C. *J. Food Comp. Anal.* 2007, 20, 440.
11. Pohl, P.; Prusisz, B. *Food Chem.* 2007, 102, 1415.
12. Sanvicens, N.; Moore, E. J.; Guilbault, G. G.; Marco, M. P.; *J. Agric. Food Chem.* 2006, 54, 9176.
13. Basheer, C.; Chong, H. G.; Hii, T. M.; Lee, H. K. *Anal. Chem.* 2007, 79, 6845.
14. I. Wilson, D. *Anal. Chem.* 1987, 59, 2830.
15. Zhang, W.; Lu, Y.; *J. Comb. Chem.* 2007, 9, 836.
16. Curran, D. P.; Luo, Z.; *J. Am. Chem. Soc.* 1999, 121, 9069.
17. Matsugi, M.; Curran, D. P. *Org. Lett.* 2004, 6, 2717.
18. Yang, P.; Cao, Y.; Hu, J. C.; Dai, W. L.; Fan, K. N. *Applied Catalysis A: General* 2003, 241, 363
19. Arai, T.; Watanabe, M.; Yanagisawa, A. *Org. Lett.* 2007, 9, 3595.
20. Hird, A. W.; Hoveyda, A. H. *J. Am. Chem. Soc.* 2005, 127, 14988.
21. Lee, D.; Yun, J. *Tetrahedron Lett.* 2005, 46, 2037-2039.
22. Biffis, A.; Filippi, F.; Palma, G.; Lora, S.; Macca, C.; Corain. B. *J. Ma Cat. A: Chemical* 2003, 203, 213-220.
24. Wu, X. H.; Gorden, A. E. V. *J. Comb. Chem.* 2007, 9, 601.
25. Wu, X. H.; Gorden, A. E. V.; Tonks, S. A.; Vilseck, J. Z. *J. Org. Chem.* 2007, 72, 8691.
26. Holbach, M.; Week, M. *J. Org. Chem.* 2006, 71, 1825.
27. Abdel-Magid, A. F.; Carson, K. G.; Harris, B. D.;. Maryanoff, C. A.; Shah, R. D. *J. Org. Chem.* 1996, 61, 3849.

Example 6

Wu et al., "2-Quirtoxalinol Salen Copper Complexes for Oxidation of Aryl Methylenes," Eur. J. Org. Chem., Volume 2009 Issue 4, Pages 451-454, 13 Jan. 2009, the content of which is incorporated herein by reference in its entirety.

Abstract

A copper (II) complex of the 2-quinoxalinol salen ligand (salquCu) 1 has been tested for use in catalysis. Here, an optimized method for oxidation of aryl methylenes and its potential applications are described. In organic solvents, the yields obtained are higher than other commonly used catalytic methods. Because this methods does not require high heat or increased pressure, this presents an opportunity for more environmentally friendly or "green" chemistry in a single phase system. Using this method, a key fragment of natural products Vitamin $K_1$ and $K_2$, 1,4-naphthoquinone, can be synthesized from 1,2,3,4-tetra-hydronaphtinalene in increased yield (65%) as compared to established methods (30-40% yield) that require higher temperatures and increased pressure.

Introduction

The development of new metal catalysts has been of wide interest in synthetic methodology; however, the application of these in the pharmaceutical industry has been limited for many reasons. Developing less-expensive, easier to use, or more environmentally friendly metal catalysts is a promising trend for new synthetic methods. The oxidation of C—H bonds offers benefits in commercial organic synthesis in the form of "greener" chemistry by energy efficiency, and operational simplicity, while at the same time reducing wastes.

Salen metal (Mn, Ru, Co, Cu, etc.) complexes have been used in the development of catalysts for numerous reactions, among these the oxidation of activated C—H bonds; however, this reaction is limited by low solubility of salen ligands in organic solvents resulting in low yields. For these reasons, a modified salen system that can be used for oxidation of activated C—H bonds is useful.

Previously, several methods of oxidation of aryl methylenes to form aryl carbonyls or aryl α-hydroxyl groups have been described. The utility of these systems has often been limited by the need for selectivity. In the 1970's, researchers used $Se_2O$ as the oxidant for reactions like this; however, the mechanism was determined to proceed with the formation of β-ketoseleninic acids leading to numerous byproducts. Oxidations with manganese salts or nitropyridinium salts were found to have a hydrogen transfer and radical mechanism, but these resulted in low yields (less than 60%). Singlet oxygen has also been investigated for use as an oxidant, but because this reaction also involves radical mechanism, the products are a mixture of the α-keto and α-hydroxyl group products. More recently, methods of oxidation using hypervalent iodine, tert-butylhydroperoxide, Jones reagent, DDQ, or peroxyacid have been reported. Yields of these methods are still less than 80%, and these methods require rigorous controlled conditions.

For this kind of oxidation, catalysts are required for acceleration of the reaction and improvement of yields. Metal catalysts used in this way have included copper, cobalt or ruthenium salts. For this purpose, salen ligands have been used as manganese or copper catalyst supports. One promising method developed recently is the Gif system, in which an iron catalyst is combined with a suitable carboxylic acid, pyridine, zinc dust (as a reductant) with oxygen as the oxidant, to acylate methylene; however, less than 40% yields were obtained. Many articles have reported high conversion rates of this oxidation as determined by GC or HPLC; however, this is not a good reflection of isolable yields, due to the different absorptions between starting materials and products. This is especially true in the oxidation of an aryl methylene group into an aryl carbonyl group which should exhibit a stronger UV absorption. For this particular oxidation, it is difficult to identify a metal catalyst possessing both good solubility in organic polar aprotic solvents (for example, $CH_3CN$) and non polar solvents (for example, hexane), a bottleneck to the oxidation of non polar compounds like steroids.

Figure 7:
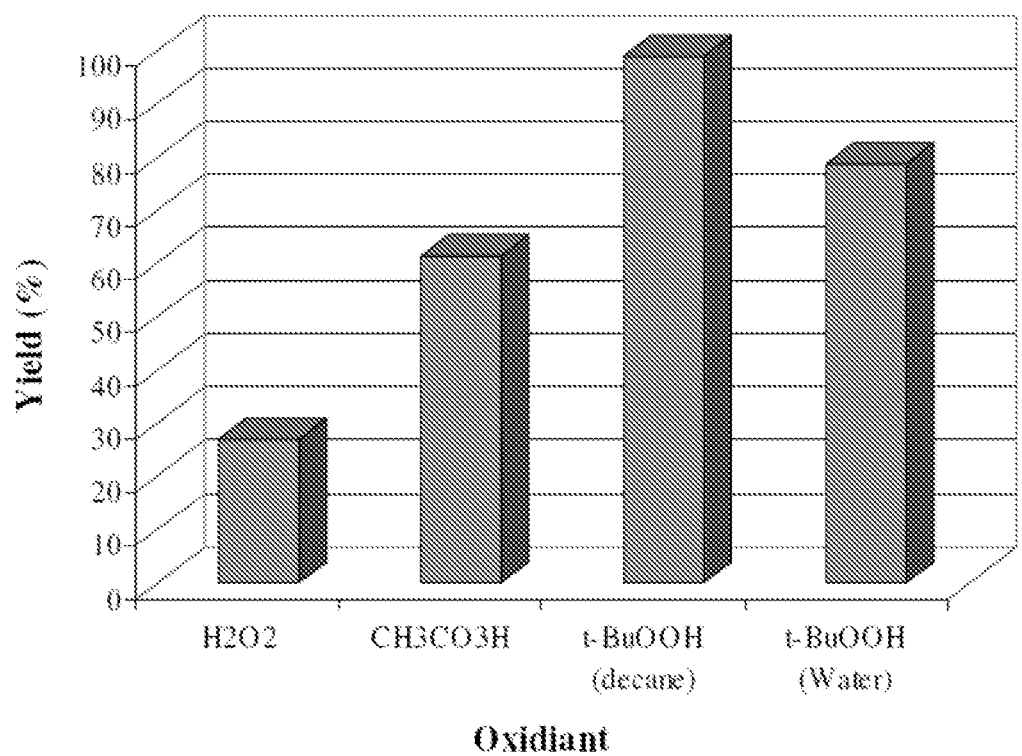
FIG. 7. illustrates the yield for oxidation of diphenylmethane into benzophenone in acetonitrile for several oxidants. Yields are based on purification by flash column chromatography.
Figure 8:
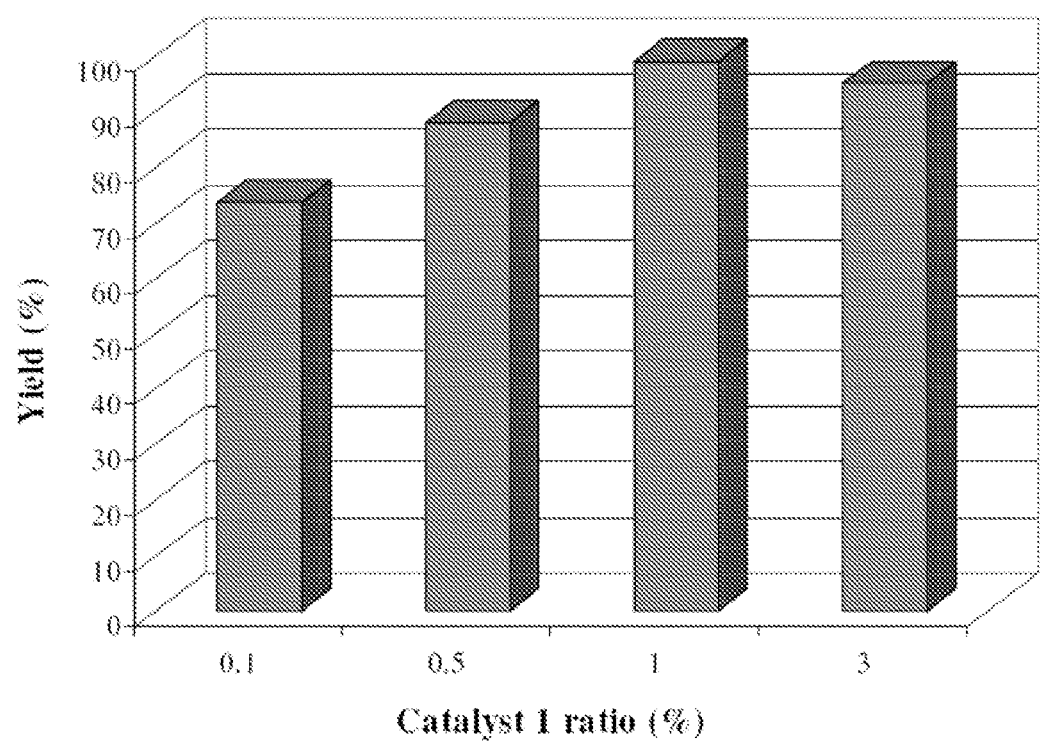
FIG. 8. illustrates the yield for oxidation of diphenylmethane into benzophenone in acetonitrile for various ratios of catalyst. Yields are based on purification by flash column chromatography.
Figure 9:
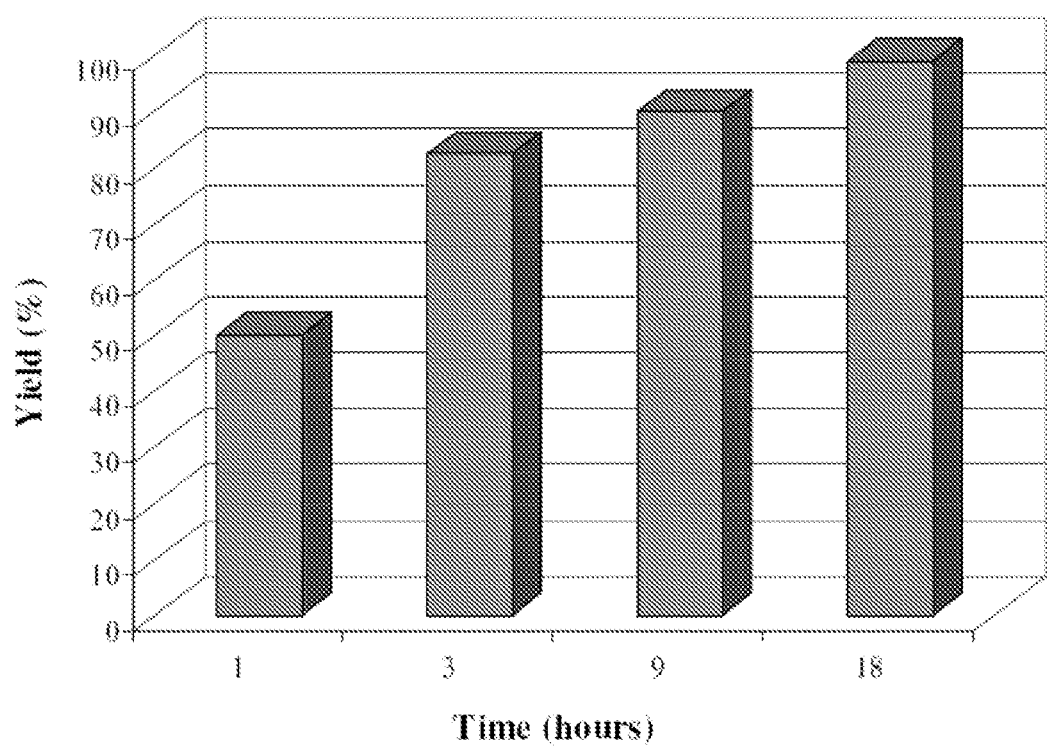
FIG. 9. illustrates the yield for oxidation of diphenylmethane into benzophenone in acetonitrile versus time. Yields are based on purification by flash column chromatography.
Figure 10:
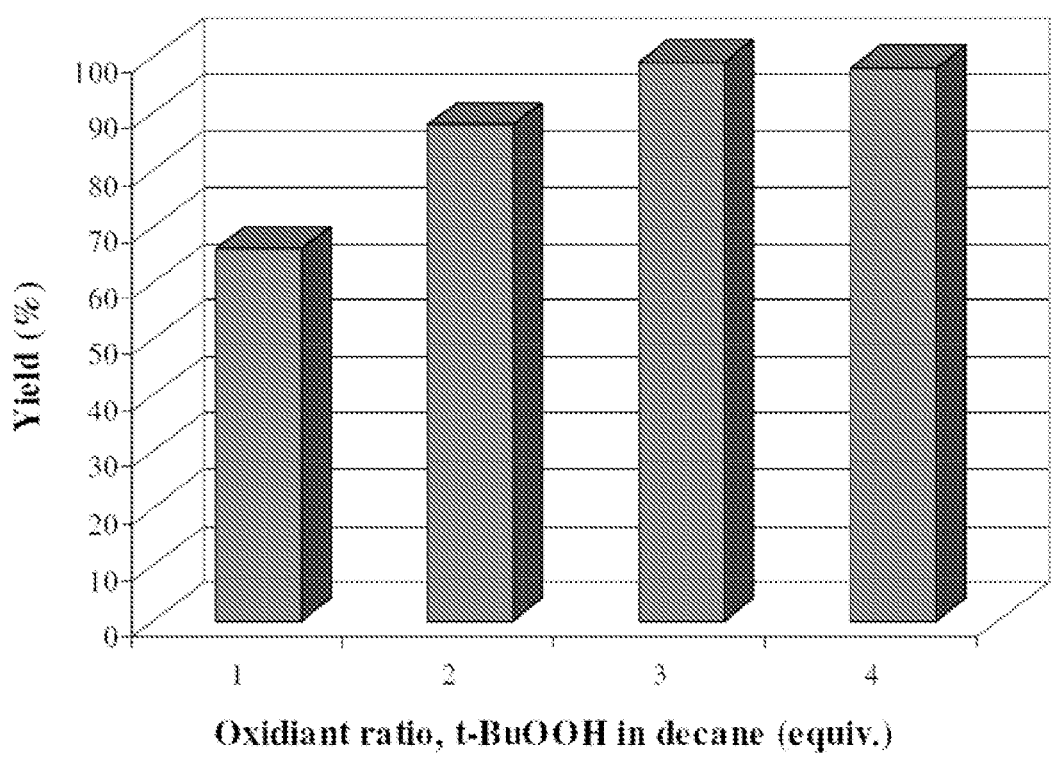
FIG. 10. illustrates the yield for oxidation of diphenylmethane into benzophenone in acetonitrile for various ratios of oxidant. Yields are based on purification by flash column chromatography.
Figure 11:
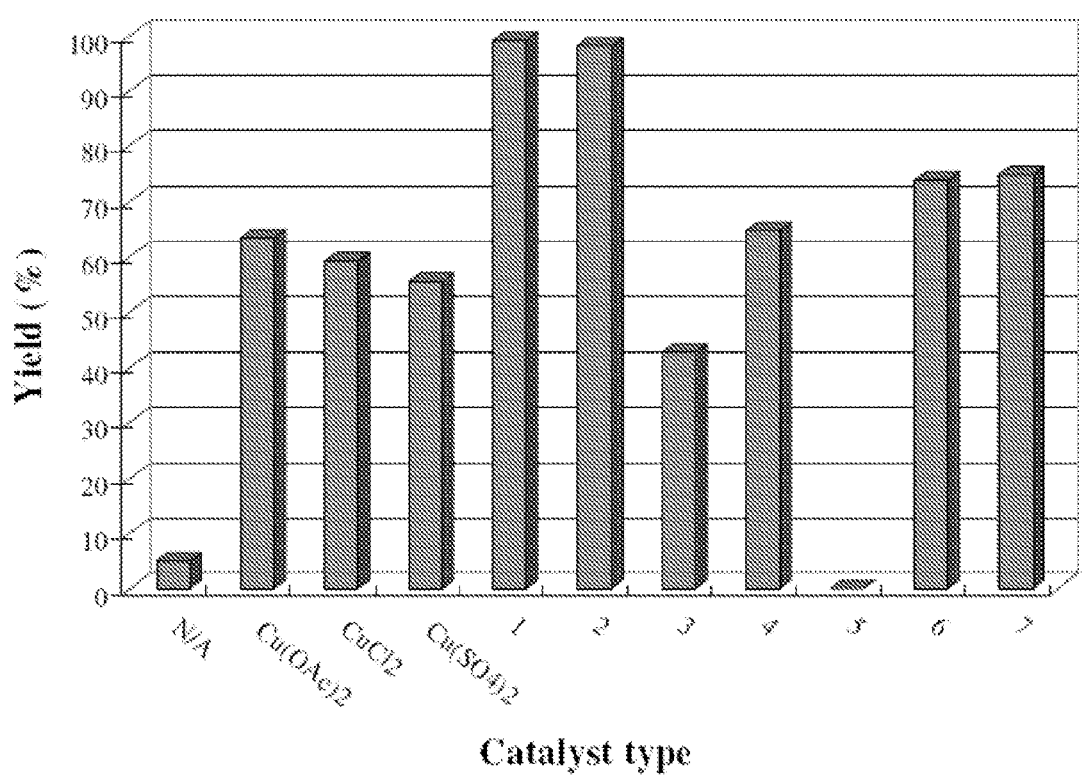
FIG. 11. illustrates reaction yields using copper salts or ligand supported metal catalysts (salen, salph, and salqu ligands). Yields are based on separation by flash column chromatography.

Based on the 2-quinoxalinol salen ligands (salqu), a new copper catalyst, salquCu 1 (FIG. 6) was developed. This metal complex can be used as a catalyst in the conversion of aryl methylene groups into aryl carbonyl groups. Described here is a method of using this catalyst, and its selectivity is characterized. Potential applications of the salquCu catalyst 1 are proposed Results and Discussion The conversion of diphenylmethane into benzophenone was selected to test the activity of catalyst salquCu 1 and to develop optimized conditions, Based on previous reports with salphCu, three equivalents of $H_2O_2$ in $CH_3CN$ as solvent with 1% by molar of the catalyst salquCu 1 was heated to reflux temperature for 18 hours. Under these conditions, the isolated yield of benzophenone was only 27%. Six experimental factors were considered to optimizing this reaction: oxidant (FIG. 7), catalyst ratio (FIG. 8), reaction time (FIG. 9), oxidant ratio (FIG. 10), solvent, and types of catalyst (FIG. 11 and Table 10).

First, four oxidants were tested using $CH_3CN$ as solvent in each case, with 1% of catalyst 1 at reflux temperature for 18 hours. (FIG. 7) It was found that tert-butylhydroperoxide in decane was the best oxidant, quantitatively converting diphenylmethane into benzophenone. When tert-butylhydroperoxide in water was used as the oxidant, the yield of product, benzophenone, was around 80%. (FIG. 7) The use of tert-butylhydroperoxide in decane allows for a uniform or monophasic organic soluble catalyst system, and thus further improves the optimal yield.

With tert-butylhydroperoxide in decane as oxidant, the catalyst ratio was increased from 0.1% to 3% (Their turnover numbers are 736, 176, 99 and 32 respectively.) It was found that 1% of catalyst 1 was best for this oxidation. (FIG. 8) Although 0.1% catalyst 1 leads to the highest turnover number, using 1% catalyst 1 results in the optimal yields within 18 hours. Increasing the amount of catalyst beyond this point did not decrease the reaction time required to achieve the optimal yield of benzophenone. Using less than 1% catalyst resulted in reduced yields. (FIG. 8) Decreasing the reaction time or oxidant ratio also results in lower yields. (FIGS. 9 and 10) The addition of more of the tell-butylhydroperoxide oxidant also does not serve to decrease the reaction time. (FIG. 10)

Finally, several polar and non polar solvents were tested. With acetonitrile, chloroform, toluene and hexane as solvents, the yields of the desired product, benzophenone, were very high (over 95%), but using THF as solvent, the yields were very low, because of the degradation of THF under oxidative conditions. When toluene was used as solvent, there were not any byproducts generated by reaction of the toluene obtained. Therefore, the optimal reaction conditions require acetonitrile (toluene, hexane or chloroform) as solvent, the addition of 3 equivalents of tert-butylhydroperoxide in decane as oxidant, with 1% of the catalyst salquCu 1. The reaction mixture heated to reflux temperature and found to be complete after 18 hours.

Figure 6:
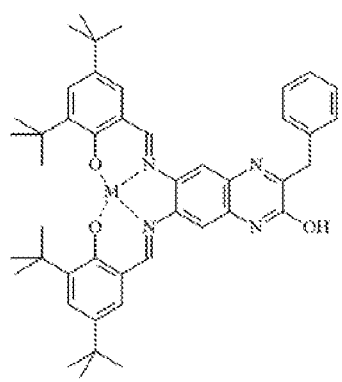
FIG. 6. illustrates the structures of salen, salph, and salqu copper complex catalysts (1-7)
Figure 6:
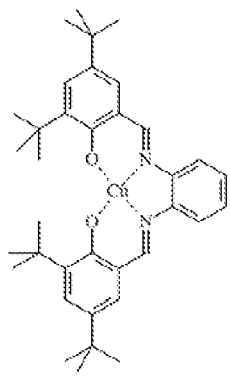
Figure 6:
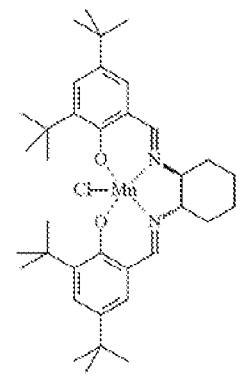

Previously, a library of salqu ligands has been prepared using combinatorial methods. These have been used to prepare stable metal complexes of broad solubility with $Ni^{2+}$, $Co^{2+}$, $Cu^{2+}$, $Mn^{2+}$ or $UO_2^{2+}$. Different metal complexes were tested as catalysts. (FIG. 6)

Without the addition of catalyst, oxidation using 3 equivalents of tem-butylhydroperoxide in decane as oxidant in acetonitrile heated to reflux temperature for 18 hours, resulted in a very modest yield. Only about 5-10% of the desired product, benzophenone, was obtained. With the addition of copper salts to the reaction mixture, 50-60% benzophenone can be obtained. The addition of the salph Cu complex 6 increased the yield of benzophenone obtained to 74%. Using the salen Mn complex 7, produced a similar result, 75%.

Why using the catalysts 6 and 7 results in lower yields than catalyst salquCu I remains unclear, but two possibilities come to mind. Judging from the uranyl ($UO_2^{2+}$) crystal structure, the salqu metal complexes (1-5) have a slightly different metal coordination geometry than the salph (6) and salen complexes (7). The salqu ligand in the uranyl ($UO_2^{2+}$) metal complex is puckered and has the metal lifted above the plane of the ligand while the salen and salph (6) and salen complexes (7) are planar. The salqu complexes also have improved solubility in numerous organic solvents. Either characteristic of these complexes could affect the catalytic reaction mechanism and lead to the observed improved yields. The improved solubility of catalyst salquCu 1 also eliminates the need for a biphasic system, which would be useful in applying this system to larger scale applications.

As a demonstration of the importance of solubility toward the efficacy of this reaction, different salqu copper complexes were examined in catalytic studies. The results of these experiments are depicted in Table 1.0.

TABLE 10

Optimized conditions with different salquCu catalysts (1x).

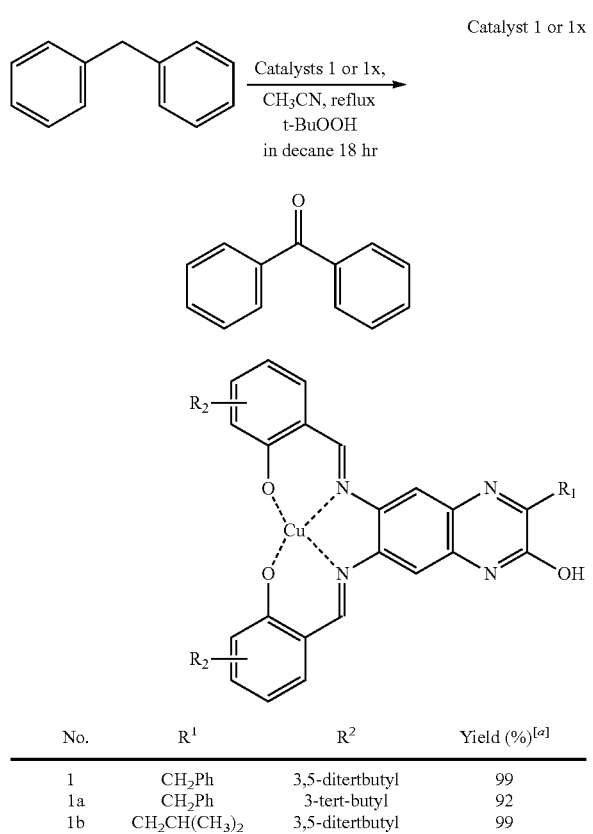

| No. | R$^1$ | R$^2$ | Yield (%)[a] |
|---|---|---|---|
| 1 | CH$_2$Ph | 3,5-ditertbutyl | 99 |
| 1a | CH$_2$Ph | 3-tert-butyl | 92 |
| 1b | CH$_2$CH(CH$_3$)$_2$ | 3,5-ditertbutyl | 99 |

TABLE 10-continued

| 1c | CH$_2$CH(CH$_3$)$_2$ | H | 90 |
| 1d | CH$_2$CH(CH$_3$)$_2$ | 5-OH | 80 |
| 1e | CH(CH$_3$)$_2$ | H | 90 |
| 1f | CH(CH$_3$)$_2$ | 5-OH | 65 |
| 1g | CH$_2$CH$_2$SCH$_3$ | 3-OH | 77 |

[a]Yields are based on separation by flash column chromatography and mass calculation.

Besides catalyst 1, tert-butyl functionalized copper complexes 1a and 1b show good catalytic effect, whereas hydroxyl functionalized complexes 1f and 1g lead to yields comparable with regular the manganese salen and copper salph complexes 6 and 7. It is also possible that the hydroxyl group impairs the catalytic function of Cu or Mn, leading to the lower yields. Complexes 1c and 1e gave a lower yield than catalysts 1, 1a and 1b, probably because of reduced solubility.

Catalyst (1) is stable to air and moisture and can be reused at least twice. Catalysts that are found to be stable both to air and moisture are much more convenient for their application. Stable capability was tested using the reaction conditions to oxidize diphenylmethane.

Diphenylmethane was reacted with 1% catalyst 1 and 3 equivalents Lent-butylhydroperoxide in refluxing acetonitrile for 18 hours. After 18 hours, an additional equivalent of diphenylmethane, and 3 equivalents oxidant were added into reaction system. The reaction mixture was allowed to continue refluxing for another 18 hours. After this period of time, the addition was repeated. Filially, the pure benzophenone product was obtained by flash column chromatography. The total yield was over 95% of the combined amounts of starting material. While the addition of additional material in the initial reaction (lowering the % catalyst present) reduces the yield produced in 18 hours, the addition of additional materials in increments indicates that the catalytic species is regenerated during the course of the reaction and that the catalyst 1 was reused at least twice. This increases the overall lifetime of the usable catalyst and could be of benefit to reduce volumes of solvents required in larger scale reactions.

Once the optimal conditions were determined, these were used in reactions with several compounds containing aryl methylene group to be oxidized (Table 11).

TABLE 11

Tested Aryl methylene compound using catalyst 1.

| Entry [a] | Starting material | Final product | Yield (%)[J] |
|---|---|---|---|
| 1 | (diphenylmethane) | (benzophenone) | 99[c] |
| 2 | (benzylamine) | (benzaldehyde) | 88[c]; [e] |

TABLE 11-continued

Tested Aryl methylene compound using catalyst 1.

| Entry [a] | Starting material | Final product | Yield (%)[f] |
|---|---|---|---|
| 3 | PhCH₂OCH₃ | methyl benzoate | 93[c] |
| 4 | 4-O₂N-C₆H₄-CH₂CH₃ | 4-O₂N-C₆H₄-C(O)CH₃ | 50[c]; 90[d] |
| 5 | PhCH₂COOEt | PhC(O)COOEt | 14[c]; 82[d] |
| 6 | PhCH₂CH₂CH₂CH₃ | PhC(O)CH₂CH₂CH₃ | 80[c] |
| 7 | Ph₂CHCH₂CH₃ | Ph₂C=O | 81[c] |
| 8 | PhCH₂CH₃ | PhC(O)CH₃ | 80[c] |
| 9 | PhCH₂OH | PhCHO | 47[c] |
| 10 | tetralin | α-tetralone + 1,4-naphthoquinone | 26[d]; 66[d] |

TABLE 11-continued

Tested Aryl methylene compound using catalyst 1.

| Entry [a] | Starting material | Final product | Yield (%)[f] |
|---|---|---|---|
| 11 | 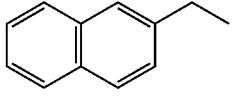 | 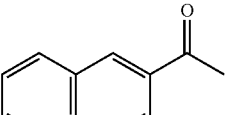 | 60[c]; 91[d] |
| 12 | 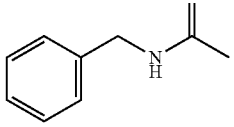 | 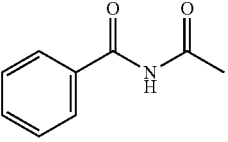 | —[b] |
| 13 | 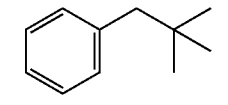 | 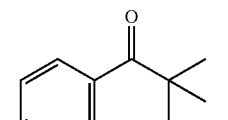 | —[b] |
| 14 | 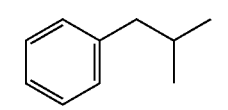 | 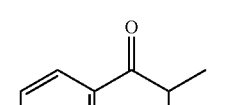 | —[b] |
| 15 | 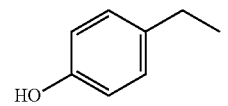 | 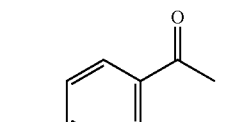 | —[b] |
| 16 | 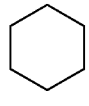 | 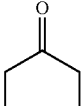 | —[b] |
| 17 | 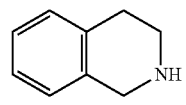 | 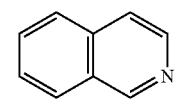 | 56[c] |
| 18 | 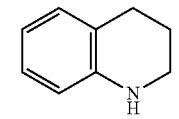 | 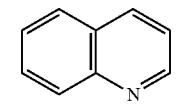 | 66[c] |

[a]All of products were characterized by $^1$H and $^{13}$C NMR and found to be in agreement with their standard NMR spectrum.
[b]None of the expected final product was obtained.
[c]Method 1: 1% catalyst 1, CH$_3$CN, 3 equivalents t-BuOOH (in decane), reflux for 18 hours.
[d]Method 2: (1) 1% catalyst 1, CH$_3$CN, 3 equivalents t-BuOOH (in decane), reflux for 18 hours. (2) 3 equivalents t-BuOOH (in decane), CH$_3$CN, reflux for 18 hours.
[e]After 40 minutes the Schiff base product, N-benzylidenebenzylamine was formed. 89% of benzaldehyde was determined by adding the reacted benzaldehyde with pure isolated benzaldehyde.
[f]Yields are based on separation by flash column chromatography and mass calculation.

It was found that if there is an electron donor group neighbouring to the methylene group to be oxidized, the yield is increased (Entry 1, 2 and 3), whereas if there is a neighbouring electron withdrawing group the yield will decrease (Entry 4, 5). Aryl methylene compounds with neighbouring electron withdrawing groups can be oxidized again to enhance the final yields (Table 11, Method 2). Aryl methylene groups can be selectively oxidized, while other methylene groups were not affected (Entry 6). If an amino or hydroxyl group is present neighbouring to the methylene group, the final product produced is an aldehyde (Entry 2 and Entry 9). By this method, not only may the aryl methylenes be oxidized to the corresponding carbonyl groups, but an ether group can be converted to an ester in good yields (Entry 3).

If there is no aryl group neighbouring the methylene group, the expected product is not obtained (Entry 16). This could also be due to steric limitations on the configurational geometry of the metal complex to the catalytic mechanism. For example, when there is a bulky tert-butyl group on the methylene, none of the expected product found (Entry 13, 14). Compounds containing a hydroxyl group were found to have no reaction (Entry 15) or lower yields (Entry 9), presumably because the oxygen atom could coordinate with the catalyst metal centre, (in this case copper), and this may block the catalyst mechanism. Remarkably, tetra-hydroisoquinoline and tetra-hydroquinoline were special cases. Oxidation of tetra-hydroisoquinoline and tetra-hydroquinoline using this method leads to isoquinoline and quinoline (Entry 17 and 18 respectively), but not α-ketoisoquinoline or α-ketoquinoline analogs. For some of the oxidation reactions found to have poor yields, the yield can be improved using a modified reaction scheme, method 2. (Entry 4, 5, 10 and 11).

The oxidation of benzylamine directly into benzaldehyde by the catalyst I mimics the important biological process of oxidation of amine substrates to aldehydes as catalyzed by the naturally occurring metalloenzymes that contain copper, namely amine and lysyl oxidases (Entry 2). Once the benzaldehyde is generated, this can react directly with any remaining unreacted benzylamine to form N-benzylidenebenzylamine. N-benzylidenebenzylamine is a useful, costly but commercially available, indicator reagent used for organolithium assays and as an intermediate of amino acid syntheses, and this is a potentially useful as an inexpensive method to prepare N-benzylidenebenzylamine directly from benzylamine.

In another example of the potential utility of this catalyst, 1,4-naphthoquinone is typically prepared on an industrial scale from naphthalene using oxygen gas with a vanadium catalyst at high temperature while under pressure. This reaction typically yields no more than 40%. This is an important compound as it is a key intermediate of several natural products including phylloquinone and menaquinone (vitamin $K_1$ and $K_2$), the derivatives of which have been found to have broad bioactivity ranging from anticancer to antifungal. Several new methods for preparing 1,4-naphthoquinone derivatives have been developed, but all of them involve more expensive metal catalysts. Disclosed here is a new method for preparing 1,4-naphthoquinone by using inexpensive commercial available starting material 1,2,3,4-tetrahydronaphthalene and salquCu catalysts 1 with 63% yield. (Entry 10) This conversion also mimics another crucial biological oxidization process catalyzed by galactose oxidase.

This is a promising new result, but it remains to determine the specific oxidation mechanism, although the mechanism of oxidation by copper salt and THBP has been investigated. This can be difficult, because if the mechanism involves a carbon cation intermediate, the methoxyl group should be better leaving group than hydrogen (Entry 3) in conversion of phenyl methyl ether to methyl benzoate. In contrast, in the reactions characterized here the hydrogen acts as the leaving group. Secondly, if the mechanism involves a radical intermediate, the conversion of 1,1-diphenylpropane to benzophenone can not be explained and the expected products 1,1-diphenylpropanol should be obtained as a final reasonable product. (Entry 7) In addition, conversion of tetra-hydroquinoline to quinoline, expected α-ketoquinolines have not been obtained, indicating an unexpected mechanism occurs. (Entry 17 and 1.8) Another question that arises is in the case of benzylamine. (Entry 2) The expected product would be benzoic amide; however, the major product found is benzaldehyde in very good yield (>88%).

Conclusions

The unusual salquCu metal complex 1 was developed for use in oxidation of aryl methylenes with good yields. Results of the optimization process indicate that the configuration and solubility of salqu copper complex catalyst (e.g., 1) are key factors during the oxidation. Besides the salqu copper complex 1, the salqu manganese complex was also found to demonstrate catalytic ability.

Using the copper catalyst 1., an important fragment of natural compound, 1,4-naphthoquinone, can be obtained in high yields, and the oxidations of the metalloenzymes amine oxidase and galactose oxidase, can be mimicked. These types of catalysts present a new option for use in industry or organic syntheses because of their relative ease of preparation, low sensitivity to moisture and air, and the use of more environmentally friendly and less costly metals. They are also soluble in many common organic solvents. They possess high catalytic efficiency and can be reused at least twice. The salqu metal complexes disclosed here (e.g., 1) may be particularly useful after incorporation into polymers for use in solid phase catalysts based on the developed solid phase extraction (SPE) technology.

Experimental Section

All of starting materials were purchased from Acros Organics Co., TCI or Alfa Aesar Inc and were used as received. The tert-butylhydroperoxide in decane (6M) and salen Mn complex 7 used were purchased from Sigma-Aldrich Co. Salqu ligands were synthesized by previous procedure published. Solvents were purchased from Thermo Fisher Scientific Co. and were used directly. $^1H$ and $^{13}C$ NMR spectra were recorded on Bruker AC 250 spectrometer (operated at 250 and 62.5 MHz, respectively) or Bruker AV 400 spectrometer (operated at 400 and 100 MHz, respectively). The final synthesized products (Entry 1 to 19) were identified by TLC, $^1H$ and $^{13}CNMR$ and compared with TLC, $^1H$ and $^{13}CNMR$ of commercially available compounds. The known $^1H$ and $^{13}C$-NMR of commercial available compounds are available from spectral database for organic compounds (SDBS), National Institute of Advanced Industrial Science and Technology (AIST), Japan. Chemical shifts are reported as δ values (ppm), NMR data were collected by using $CDCl_3$ or DMSO-$d^6$. The solvents used are indicted in the experimental details. Reaction prowess was monitored by thin-layer chromatography (TLC) using 0.25 mm Whatman Aluminum silica gel 60-F254 precoated plates with visualization by irradiation with a Mineralight UVGL-25 lamp. The products yields are based on separation by flash column chromatography.

Method 1

The synthesis of the products depicted in Table 11 began with the combination of catalyst 1 (0.02 mmol, 15.2 mg) and 2.0 mmol of starting material (aryl methylene compound) dissolved in 2.0 mL acetonitrile with 1.0 mL tert-butylhydroperoxide decane solution (6.0 mmol). The reaction mixture was allowed to stir for 18 hours at 70° C. and monitored by TLC. Once the starting material can no longer be seen by TLC, the reaction was considered complete. Pure products were obtained using flash column chromatography with a solution of hexane:ethyl acetate, 10-20:1 as the eluent. The yields of final pure products were from 45.99%. (See notation in Table 11.)

Method 2

For reactions found to result in low yields (see Table 11), a modified procedure was employed. The procedure began with of the addition of catalyst 1 (0.02 mmol, 15.2 mg) and 2.0 mmol of starting materials (aryl methylene compounds) dissolved in 2.0 mL acetonitrile and 1.0 mL tert-butylhydroperoxide decane solution (6.0 mmol). The reaction mixture was allowed to stir for 18 hours at 70T. After 18 hours, an additional 1.0 mL tert-butylhydroperoxide decane solution (6.0 mmol) was added and the solution was heated at reflux temperature for an additional 18 hours. The reaction was monitored by TLC. Once the starting material can no longer be seen by TLC, the reaction was considered complete. Pure products were obtained by purification using flash column chromatography with a solution of hexane ethyl acetate, 10-20:1 as eluent. The yields of final pure products were from 65-92%. (See notation in Table 11.)

Data Section

Entry 1—$^1$H-NMR (400 MHz, CDCl$_3$): δ 7.49 (t, 4H), 7.62 (t, 2H), 7.84 (d, 4H). $^{13}$C-NMR (100 MHz, CDCl$_3$): δ 196.8, 137.6, 132.5, 130.1, 1283.

Entry 2—N-benzylidenebenzylamine: $^1$H-NMR (400 MHz, CDCl$_3$): δ 4.87 (s, 2H), 728-7.93 (m, 10H), 8.43 (s, 1H). $^{13}$C-NMR (100 MHz, CDCl$_3$): δ 162.5, 139.0, 136.4, 134.5, 130.9, 130.6, 64.9. Benzaldehyde: $^1$H-NMR (400 MHz, CDCl$_3$): δ 7.50 (t, 2H), 7.60 (t, 1H), 7.86 (d, 2H), 10.01 (s, 1H). $^{13}$C-NMR (100 MHz, CDCl$_3$): δ 191.9, 136.0, 134.0, 129.3, 128.6.

Entry 3—$^1$H-NMR (400 MHz, CDCl$_3$): δ 3.91 (s, 3H), 7.43 (t, 2H), 7.53 (t, 1H), 8.05 (d, 2H). $^{13}$C-NMR (100 MHz, CDCl$_3$): δ 167.1, 132.9, 130.2, 129.6, 128.4, 128.2, 126.9, 52.0.

Entry 4—$^1$H-NMR (250 MHz, CDCl$_3$): δ 2.71 (s, 3H), 8.15 (d, 2H), 8.35 (d, 2H). $^{13}$C-NMR (62.5 MHz, CDCl$_3$): δ 196.3, 141.4, 129.3, 123.9, 27.0.

Entry 5—$^1$H-NMR (400 MHz, CDCl$_3$): δ 1.43 (t, 3H), 4.60 (q, 2H), 7.53 (t, 2H), 7.67 (t, 1H), 8.01 (d, 2H). $^{13}$C-NMR 000 MHz, CDCl$_3$): δ 186.5, 163.9, 134.9, 132.4, 130.0, 128.9, 62.4, 14.1.

Entry 6—$^1$H-NMR (400 MHz, CDCl$_3$): δ 1.02 (t, 3H), 1.97 (m, 2H), 2.96 (t, 2H), 7.46 (t, 2H), 7.53 (t, 1H), 7.96 (d, 2H). $^{13}$C-NMR (100 MHz, CDCl$_3$): δ 200.4, 137.1, 132.9, 128.4, 128.2, 128.0, 40.5, 27.2, 13.9.

Entry 7—$^1$H-NMR (400 MHz, CDCl$_3$): δ 7.50 (t, 4H), 7.62 (t, 2H), 7.85 (d, 41-1). $^{13}$C-NMR (100 MHz, CDCl$_3$): δ 196.8, 137.6, 132.4, 130.1, 128.3.

Entry 8—$^1$H-NMR (400 MHz, CDCl$_3$): δ 2.57 (s, 3H), 7.49 (t, 2H), 7.60 (t, 1H), 7.94 (d, 2H). $^{13}$C-NMR (100 MHz, CDCl$_3$): δ 198.4, 1373, 133.6, 129.1, 128.6, 27.2.

Entry 9—$^1$H-NMR (400 MHz CDCl$_3$): δ 7.50 (t, 2H), 7.60 (t, 11.1), 7.86 (d, 2H), 10.01 (s, 1H). $^{13}$C-NMR (100 MHz, CDCl$_3$): δ 191.9, 136.0, 134.0, 129.3, 128.6.

Entry 10—$^1$H-NMR (400 MHz, DMSO-d$^6$): δ 7.02 (s, 2H), 7.80 (dd, 2H), 8.13 (dd, 2H). $^{13}$C-NMR (100 MHz, DMSO-d$^6$): δ 185.1, 138.7, 134.0, 131.9, 126.5.

Entry 11—$^1$H-NMR (250 MHz, CDCl$_3$): δ 2.71 (s, 3H), 7.56 (m, 2H), 7.62 (m, 4H), 8.05 (s, 1H). $^{13}$C-NMR (62.5 MHz, CDCl$_3$): δ 198.1, 135.6, 134.4, 132.5, 130.2, 129.6, 128.5, 128.4, 127.8, 126.8, 123.9.

Entry 17—$^1$H-NMR (400 MHz, CDCl$_3$): δ 7.57-7.96 (m, 5H), 8.54 (d, 1H), 9.27 (s, 2H). $^{13}$C-NMR (100 MHz, CDCl$_3$): δ 152.5, 142.9, 135.8, 130.4, 127.6, 127.3, 126.5, 120.5.

Entry 18—$^1$H-NMR (400 MHz, CDCl$_3$): δ 7.29(m, 1H), 7.47 (t, 1H), 7.63 (t, 1H), 7.73 (d, 1H), 8.06 (m, 2H), 8.60 (m, 1H). $^{13}$C-NMR (100 MHz, CDCl$_3$): δ 150.3, 148.2, 136.0, 129.4, 128.2, 127.8, 126.5, 121.0.

Example 6

References

[1] (a) R. D. Smiley, G. G. Hammes, *Chem. Rev.* 2006, 106, 3080. (b) S. T. Connon, S. Blechert, *Angew. Chem. Int. Ed.* 2003, 42, 1900. (c) K. C. Nicolaou, D. Vourloumis, N. Winssinger, P. S. Baran, *Angew. Chem. Int. Ed,* 2000, 39, 44. (d) S. Caron, R. W. Dugger, S. G. Ruggeri, J. A. Ragan, D. H. B. Ripin, *Chem. Rev.* 2006, 106, 2943. (e) R. H. Grubbs, *Angew. Chem. Int. Ed.* 2006, 45, 3760. (f). R. R. Schrock, *Angew. Chem. Int. Ed.* 2006, 45, 3748. (g) Y. Chauvin, *Angew. Chem. Int. Ed.* 2006, 45, 3741.

[2] (a) P. J. Walsh, H. Li, C. A. Parrodi, *Chem. Rev.* 2007, 107, 2503. (b) B. Notari, *Catal. Today* 1993, 18, 163. (b) A. Butler, M. J. Clague, G. E. Meister, *Chem. Rev.* 1994, 94, 625. (c) J. M. Aubry, S. J. Bouttemy, *J. Am. Chem. Soc.* 1997, 119, 5286. (d) D. H. Dickman, *Chem. Rev.* 1994, 94, 569.

[3] (a) G. Dyker, *Angew. Chem., Int. Ed.* 1999, 38, 1698. (b) T. Naota, H. Takaya, S.-I. Murahashi, *Chem. Rev.* 1998, 98, 2599. (c) V. Ritleng, C. Sirli, M. Pfeffer, *Chem. Rev.* 2002, 102, 1731. (d) H. Chen, S. Schlecht, T. C. Semple, J. F. Hartwig, *Science* 2000, 287, 1995. (e) A. S. Goldman, *Nature* 1993, 366, 514.

[4] (a) A. Erkkila, I, Majander, P. M. Pihko, *Chem. Rev.* 2007, 107, 5416. (b) D. Darensbourg, *Chem. Rev.* 2007, 107, 2388. (c) N. E. Borisova, M. D. Reshetova, Y. A. Ustynyuk, *Chem. Rev.* 2007, 107, 49. (d) S. E. Denmark, E. N. Jacobsen, *Acc. Chem. Res.* 2000, 33, 324. (e) S. Dey, D. R. Powell, C. Hu, a B. Berkowitz, *Angew. Chem., Int. Ed.* 2007, 46, 7010. (f) A. Pui, J-P. Mahy, *Polyhedron* 2007, 26, 3143. (g) Z. Lue, M. Yuan, F. Pan, S. Gao, D. Zhang, D. Zhu, *Inorg, Chem.* 2006, 45, 3538.

[5] S. Velusamy, T. Punniyamurthy, *Tetrahedron Lett.* 2003, 44, 8955.

[6] (a) H. B. Henbest, B. Nicholls, *J. Chem. Soc.* 1959, 221. (b) S. Harrison, *Chem. Commun.* 1966, 752. (c) A. J. Catino, R. E. Forslund, M. P. Doyle, *J. Am. Chem. Soc.* 2004, 126, 13622. (d) H. M. C. Ferraz, Jr. L. S. Longo, *Org. Lett.* 2003, 5, 1337. (e) R. Breslow, P. C. Scholl, *J. Am. Chem. Soc.* 1971, 93, 2331. (f) J. Q. Yu, E. I. Coery, *J. Am. Chem. Soc.* 2003, 125, 3232. (g) S. Tsunoi, 1. Ryu, N. Sonoda, *J. Am. Chem. Soc.* 1994, 116, 5473.

[7] (a) A. Krief, L. Hevesi, *Organoselenium Chemistry I*, Springer, N.Y., 1998, 115. (b) E. S. Krongauz, *Russ. Chem. Rev,* 1977, 46, 59. (c) N. Rabjohn, *Org. React.* 1976, 24, 261. (c) E. J. Coery, J. P. Schaefer, *J. Am. Chem. Soc.* 1960, 82, 918. (d) K. B. Sharpless, K. M. Gordon, *J. Am. Chem. Soc.* 1976, 98, 300.

[8] (a) J. H. Markgraf, B. Y. Choi, *Synth. Commun.* 1999, 29, 2405. (b) J. H. Markgraf, C. A. Stickney, *J. Heterocyclic Chem.* 2000, 37, 109. (c) S. Negele, K. Wieser, T. Severin, *J. Org. Chem.* 1998, 63, 1138. (d) H. X. Wei, R. L. Jasoni, H. Shao, J. Hu, P. W. Pare, *Tetrahedron* 2004, 60, 11829.

[9] (a) Wasserman, H. H.; Ives, J. L. *J. Org. Chem.* 1978, 43, 3238. (b) Wasserman, H. H.; Ives, J. L. *J. Org. Chem.* 1985, 50, 3573. (c) Rao, D. V.; Stuber, F. A.; Ulrich, H. *J. Org. Chem.* 1979, 44, 456. (d) L1, P.; Fong, W. M.; Chao, L. C. F.; Fung, S. H. C.; Williams, I. D. *J. Org. Chem.* 2001, 66, 4087.

[10] (a) J. C. Lee, H. J. Park, J. Y. Park, *Tetrahedron Lett.* 2002, 43, 5661. (b) Z. L1, C. G. Xiu, C. Z. Xu, *Tetrahedron Lett.* 2003, 44, 9229. (c) N. K. Sharma, K. N. Ganesh, *Tetrahedron Lett,* 2004, 45, 1403. (d) X. Zhang, A. C. Schmitt, W. Jiang, *Tetrahedron Lett.* 2001, 42, 5335.

[11] (a) S. I. Murahashi, N. Komiya, Y. O. Kuwabara.; T. Naota, *J. Org. Chem.* 2000, 65, 9186. (b) Jr. A. R. Doumaux, D. J. Trecker, *J. Org. Chem.* 1970, 35, 2121. (c) A. J. Catino, J. M. Nichols, H. Choi, S. Gottipamula, M. P. Doyle, *Org Lett,* 2005, 7, 5167. (d) Y. Bonvin, E. Callens, I.

Larrosa, D. A. Henderson, J. Oldham., A. 3. Burton, A. G. M. Barrett, *Org Lett,* 2005, 7, 4549 (d) J. Mazurt, *Chem Rev,* 1992, 92, 113.

[12] (a) R. Rangarajan, E. J. Eisenbraun, *J. Org. Chem.* 1985, 50, 2435. (b) H. Lee, R. G. Harvey, *J. Org. Chem.* 1988, 53, 4587. (c) D. Ma, C. Xia, H. Tian, *Tetrahedron Lett.* 1999, 40, 8915.

[13] (a) A. Shaabani, D. G., Lee, *Tetrahedron Len.* 2001, 42, 5833. (b) F. Minisci, C. Punta, F. Recupero, F. Fontana, G. F. Pedulli, *J. Org. Chem.* 2002, 67, 2671. (c) S. Minakata, E. Imai, Y. Ohshima, K. Inaki, I. Ryu, M. Komatsu, Y. Ohshiro, *Chem. Len.* 1996, 19. (d) M. Miyamoto, Y. Minami, Y. Ukaji, H. Kinoshita, K. Inomata, *Chem. Len.* 1994, 1149.

[14] (a) K. Kamata, J. Kasai, K. Yamaguchi, N. Mizuno, *Org. Len.* 2004, 6, 3577. (b) P. H. J. Crlsen, T. Katsuki, V. S. Martin, K. B. Sharpless, *J. Org. Chem.* 1981, 46, 3936. (c) T. C. Lau, C. K. Mak, *J. Chem. Soc. Chem. Commun.* 1993, 766.

[15] (a) N. Komiya, S. Noji, S. I. Murahashi, *Tetrahedron Lett.* 1998, 39, 7921. (b) N. H. Lee, C. S. Lee, D. S. Jung, *Tetrahedron Lett.* 1998, 39, 1385.

[16] (a) U. Schuchardt, M. J. D. M. Jannini, D. T. Richens, M. C. Guerreiro, E. V. Spinace, *Tetrahedron* 2001, 57, 2685. (b) D. H. R. Barton, E. Csuhai, N. Ozbalik, *Tetrahedron Lett.* 1990, 31, 1657.

[17] D. H. R. Barton, *Chem. Soc. Rev.* 1996, 25, 237.

[18] (a) X. Wu, A. E. V. Gorden, *J. Comb. Chem.* 2007, 9, 601. (b) X. Wu, A. E. V. Gorden, S. A. Tonks, J. Z. Vilseck, *J. Org. Chem.* 2007, 72, 8691.

[19] X. Wu, T. H. Bray, M. S. Bharara, B. K. Tate, A. E. V. Gorden, *Inorg. Chem. Acta* 2008, in press.

[20] R. F. Moreira, E. Y. Tshuva, S. J. Lippard, *Inorg. Chem.* 2004, 43, 4427.

[21] (a) S. Nara, B. Gomes, K. T. Yosunobu, *J. Bio. Chem.* 1966, 241(12), 2774. (b) T. Koyanagi, K. Matsumura, S. Kuroda, K. Tanizawa, *Plant Cell Physiol* 2000, 41(11), 1259.

[22] R. G. Gillis, *J. Org. Chem.* 1956, 21, 805.

[23] L. Duhamel, J. C. Plaquevent, *J. Org. Chem.* 1979, 44, 3404.

[24] U. M. Azizov, L. I. Leonteva, *Pharma. Chem. J.* 1989, 23(12), 1017.

[25] (a) S. J. Elder, D. B. Haytowitz, J. Howe, J. W. Peterson, S. L. Booth, *J. Agric. Food Chem.* 2006, 54 (2), 463. (b) Y. Naruta, *J. Org. Chem.* 1980, 45, 4097.

[26] (a) I. Dai, I. Masami, Y. Yukinori, *J. Nat. Prod.* 2003, 66, 1611. (b) T. Kazuhito, Y. Hisatsugu, N. Sei-lchi, *J. Am. Chem. Soc.* 2007, 129, 12585. (c) K. Barbara, Z. Wieslawa, *Bioorg. Med. Chem.* 2007, 15(12), 4144. (d) E. Giaccomo, L. M. Grazia, L. Catarina. W. Vierle, S. M. Elisabeth, B. Roland, *Eur. J. Med. Chem.* 2006, 41(6), 773. (e) K. Barbara, Z. Wieslawa, *Bioorg. Med. Chem.* 2007, 15(12), 4144. (f) V. Claudia, M. Rui, C. G. Rita, L. Jim, J. Mohammed, T. D. Kenneth, *Bioorg. Med. Chem.* 2007, 15(15), 5340.

[27] (a) C. C. Huang, N. H. Chang, *Org. Lett.* 2008, 10(4), 673. (b) P. Chatchawan, Boonsong, K. Ngampong, *Synth. Commun.* 2007, 37(9), 1463. (c) X. L. Wang, X. F. Zheng, 3. Reiner, *Synlett.* 2006, 6, 942,

[28] (a), A. J. Baron, C. Stevens, C. Wilmot, K. D. Seneviratne, V. Blakeley, D. M. Dooley, S. E. V. Phillips, P. F. Knowles, M. J. Mcpherson, *J. Bio. Chem.* 1994, 269(40), 25095. (b) Y. Wang, T. D. P. Stack, *J. Am. Chem. Soc.* 1996, 118, 13097.

[29] G. Rothenberg, L. Feldberg, H. Wiener; Y. Sasson, *J Chem Soc, Perkin Trans* 2 1998, 2429.

[30] X. Wu, A. E. V. Gorden, *Tetrahedron Lett.* 2008, 49(30), 5200.

[31] (a) L. Zhang, G. Liu, S. D. Zhang, H. Z. Yang, L. L1, X. Wu, J. L. Yu, B. B. Kou, S. Xu, J. Li, G. C. Sun, Y. F. Ji, G. F. Cheng, *J. Comb. Chem.* 2004, 6, 431. (b) X. Wu, G. Liu, J. Zhang, Z. G. Wang, S. Xu, S. D. Zhang, L. Zhang, L. Wang, *Mol. Diver.* 2004, 8, 165. (c) G. Liu, Y. M. Fan, J. R. Calson, K. S. Lam, *J. Comb. Chem.,* 2000, 2, 467.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

The invention claimed is:
1. A compound having a formula:

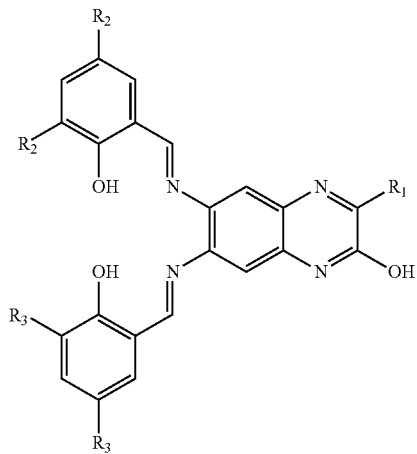

or salts, or complexes thereof, wherein:
$R_1$ is an amino acid side chain moiety of a naturally occurring amino acid, or $R_1$ is an amino acid side chain moiety of a non-naturally occurring amino acid that increases a UV-Visible extinction coefficient of the compound or that increases fluorescence of the compound;

$R_2$ and $R_3$ each independently are hydrogen, hydroxyl, $C_{1-6}$ alkyl which may be straight chain or branched, $C_{1-6}$ alkoxy which may be straight chain or branched, ether, or amine; and $R_2$ and $R_3$ are the same or different.

2. The compound of claim 1, wherein $R_1$ is selected from:

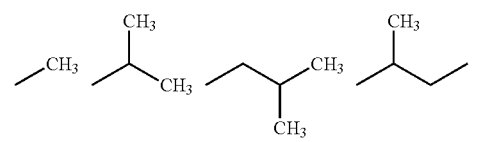

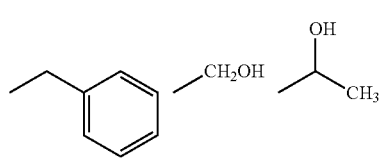

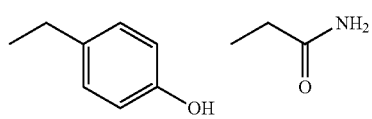

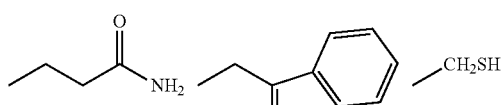

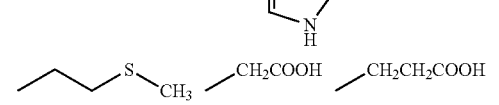

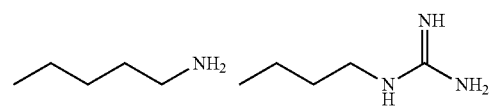

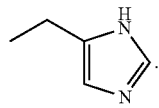

3. The compound of claim 1, wherein $R_1$ is selected from:

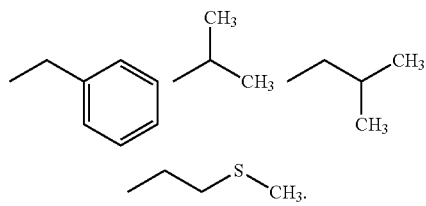

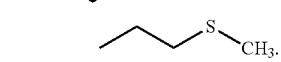

4. The compound of claim 1, wherein $R_1$ is an aromatic amino acid side chain moiety.

5. The compound of claim 1, wherein the compound has a formula selected from a group consisting of:

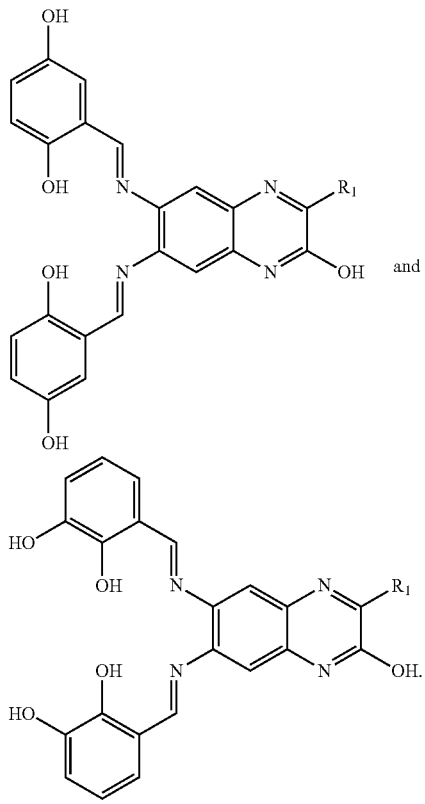

6. The compound of claim 1, wherein the compound has a formula selected from a group consisting of:

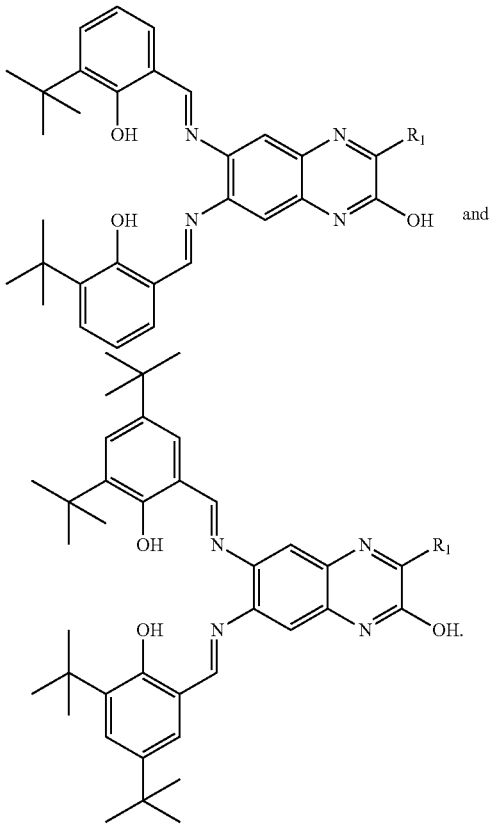

7. The compound of claim 1 complexed to a divalent cation.

8. The compound of claim 7, wherein the divalent cation is selected from a group consisting of $Cu^{2+}$, $Mn^{2+}$, $Co^{2+}$, $Ni^{2+}$, and $UO_2^{2+}$.

9. The compound of claim 1, conjugated to a solid support.

10. The compound of claim 1, conjugated to a fluorophore.

11. The compound of claim 1, wherein the amino acid side chain moiety of the naturally occurring amino acid is a phenylalanine side chain moiety.

12. The compound of claim 1, wherein $R_1$ comprises a 5- or 6-membered carbocylic or heterocylic ring substituted with N, S, or O.

13. The compound of claim 1, wherein the amino acid side chain moiety of the non-naturally occurring amino acid comprises naphthalene, anthracene, quinoline, quinoxaline, acridine, pyrimidine, pyridine, quinazoline, pyridazine, imidazole, indazole, indole, acenaphthylene, fluorine, phenanthrene, chrysene, pyrene, quinine, or anthraquinone.

14. The compound of claim 13, wherein the fluorophore is fluorescein.

* * * * *